US010155959B2

(12) United States Patent
Avisar et al.

(10) Patent No.: US 10,155,959 B2
(45) Date of Patent: Dec. 18, 2018

(54) BRONZE BUG CONTROL AGENTS

(71) Applicant: Futuragene Israel Ltd., Rehovot (IL)

(72) Inventors: Dror Avisar, Kochav Yair (IL); Daniel Siegel, Rehovot (IL); Ziv Shani, Mazkeret Batia (IL)

(73) Assignee: Futuragene Israel Ltd., Rehovot (IL)

( * ) Notice: Subject to any disclaimer, the term of this patent is extended or adjusted under 35 U.S.C. 154(b) by 0 days.

(21) Appl. No.: 14/395,595

(22) PCT Filed: Apr. 19, 2013

(86) PCT No.: PCT/US2013/037323
§ 371 (c)(1),
(2) Date: Oct. 20, 2014

(87) PCT Pub. No.: WO2013/158966
PCT Pub. Date: Oct. 24, 2013

(65) Prior Publication Data
US 2015/0082482 A1     Mar. 19, 2015

Related U.S. Application Data

(60) Provisional application No. 61/636,494, filed on Apr. 20, 2012, provisional application No. 61/787,234, filed on Mar. 15, 2013.

(51) Int. Cl.
*C12N 15/82* (2006.01)
*C12N 15/113* (2010.01)

(52) U.S. Cl.
CPC ........ *C12N 15/8286* (2013.01); *C12N 15/113* (2013.01); *C12N 15/8218* (2013.01); *C12N 2310/14* (2013.01); *C12N 2330/50* (2013.01); *Y02A 40/162* (2018.01); *Y02A 90/40* (2018.01)

(58) Field of Classification Search
CPC ................................................. C12N 15/8286
USPC ......................................................... 800/279
See application file for complete search history.

(56) References Cited

U.S. PATENT DOCUMENTS

| | | | |
|---|---|---|---|
| 2004/0265849 A1* | 12/2004 | Cargill | C07H 21/04 435/6.11 |
| 2006/0021087 A1 | 1/2006 | Baum et al. | |
| 2009/0285784 A1 | 11/2009 | Raemaekers et al. | |
| 2011/0271398 A1* | 11/2011 | Udvardi | C07K 14/415 800/278 |

FOREIGN PATENT DOCUMENTS

| | | |
|---|---|---|
| WO | 2007/035650 | 3/2007 |
| WO | 2007/080126 | 7/2007 |
| WO | 2010/141294 | 12/2010 |

OTHER PUBLICATIONS

Atkinson et al. 2009, Genbank Accession XM_001861358.*
Fourgoux-Nicol et al 1999, Plant Molecular Biology 40 :857-872.*
Thomas et al. 2001, The Plant Journal 25(4):417-425.*
Yibrah et al. 1993 Hereditas 118:273-280.*
Colliver et al. 1997 Plant Molecular Biology 35:509-522.*
Baum, J A et al.: "Control of coleopteran insect pests through RNA interference", Nature Biotechnology, Nature Publishing Group, New York, NY, US, vol. 25, No. 11, (Nov. 4, 2007), pp. 1322-1326.
Chen, J et al.: "Feeding-based RNA interference of a trehalose phosphate synthase gene in the brown planthopper, *Nilaparvata lugens*", Insect Molecular Biology, Blackwell Scientific, Oxford, GB, vol. 19, No. 6, (Aug. 19, 2010), pp. 777-786.
Everton Pires Soliman et al.: "Biology of Thaumastocoris peregrinus in different *Eucalyptus* species and hybrids", Phytoparasitica, vol. 40, No. 3, (Mar. 21, 2012) , pp. 223-230.
Huvenne, H et al.: "Mechanisms of dsRNA uptake in insects and potential of RNAi for pest control: A review", Journal of Insect Physiology, Pergamon Press, Oxford, GB, vol. 56, No. 3, Oct. 27, 2009 (Oct. 27, 2009), pp. 227-235.
Pitino, et al.: "Silencing of Aphid Genes by dsRNA Feeding from Plants", PLOS ONE, vol. 6, No. 10, (Oct. 5, 2011), p. e25709.
Nadel R L et al.: "DNA bar-coding reveals source and patterns of Thaumastocoris peregrinus invasions in South Africa and South America", Biological Invasions, Kluwer Academic Publishers, DO, vol. 12, No. 5, (Jul. 16, 2009), pp. 1067-1077.
Noack, Ann E. et al.: "Efficacy of Imidacloprid in the Control of Thoumostocoris peregrinus on Eucolyptus scoparia in Sydney, Australia", Arboriculture & Urban Forestry, vol. 35, No. 4, Jul. 2009 (Jul. 2009), pp. 192-196.
Price, D R G et al.: "RNAi-medi ated crop protection against insects", Trends in Biotechnology, Elsevier Publications, Cambridge, GB, vol. 26, No. 7, (May 22, 2008), pp. 393-400.
International Search Report for PCT/US2013/037323 dated Oct. 1, 2013.
English translation of office action dated Feb. 17, 2016 in corresponding Chinese application No. 201280027060.1.
Apis mellifera isotig 17402; Amelembr mRNA sequence, Oct. 19, 2010, retrieved online Aug. 14, 2012.
English translation of office action dated Apr. 12, 2016 in corresponding Chinese application No. 201380032751.5.
Gabriel Moura Mascarin, et al., Natural Occurrence of Zoophthora Radicans (Entomophthorales: Entomophthoraceae) on Thaumastocoris peregrinus (Heteroptera: Thaumastocoridae), an invasive pest recetnly found in Brazil; Journal of Invertebrate Pathology 110 (2012), pp. 401-404.

* cited by examiner

*Primary Examiner* — Li Zheng
(74) *Attorney, Agent, or Firm* — Fish & Richardson P.C.

(57) ABSTRACT

The present invention relates to the field of RNA-mediated gene silencing in insect species. The present invention is based, in part, on the inventors' sequencing of genes from *eucalyptus* invasive species Bronze bug pest, *Thaumastocoris peregrinus*. In certain aspects, the invention provides Bronze bug nucleic acids, derivatives thereof and the use of such nucleic acids and derivatives as Bronze bug control agents.

23 Claims, 6 Drawing Sheets
Specification includes a Sequence Listing.

P1 - 35S
P2 - sgFiMV
T1 - AtActin7
T2 - Nos

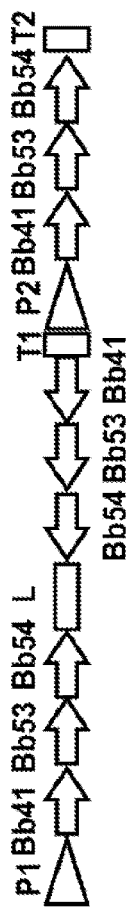
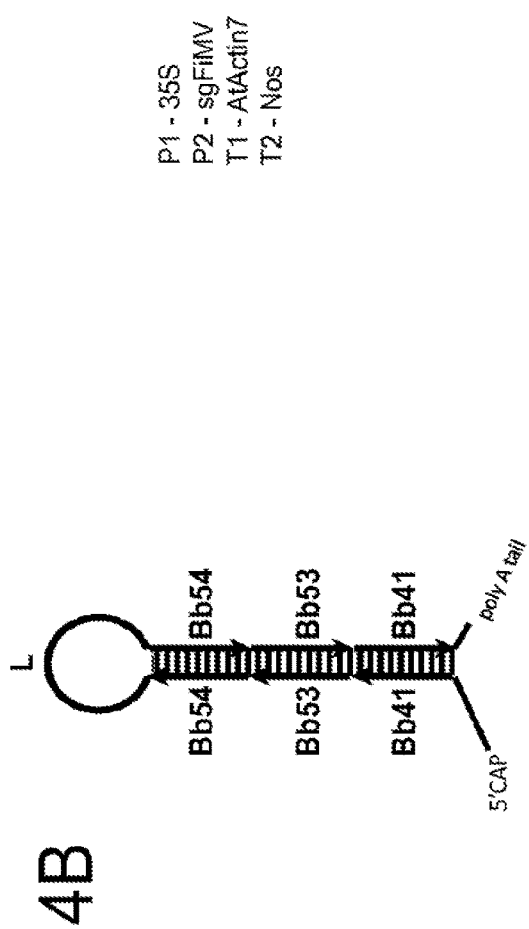
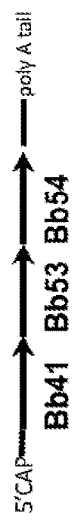
FIG. 4A
FIG. 4B
FIG. 4C

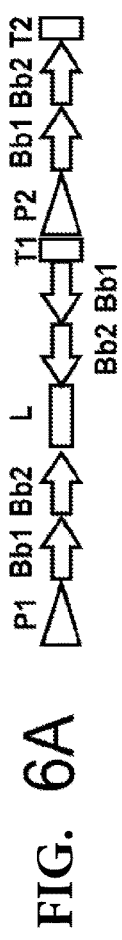
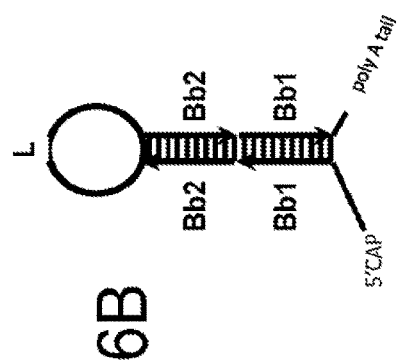
FIG. 6A
FIG. 6B
FIG. 6C

BRONZE BUG CONTROL AGENTS

SEQUENCE LISTING

The instant application contains a Sequence Listing which has been submitted in ASCII format via electronic filing and is hereby incorporated by reference in its entirety. Said ASCII copy, created on Apr. 18, 2013, is named 30407-0003WO1_SL.txt and is 54,868 bytes in size.

FIELD OF THE INVENTION

The present invention relates to the field of double stranded RNA (dsRNA)-mediated gene silencing in insect species.

BACKGROUND

*Thaumastocoris peregrinus* (Bronze bug) is a sap-sucking pest (Order Hemiptera: Thaumastocoridae) exclusively found on *eucalyptus* trees. Bronze bug infestations have occurred in the Southern hemisphere and pose a threat to commercial *eucalyptus* farming in Australia, Africa, and South America. Infestations have been observed, for example, in the species *E. camaldulensis, E. tereticornis* and *E. smithii* and the hybrids *E. grandis×E. camaldulensis* and *E. grandis×E. urophylla*. Bronze bug infestation reduces the photosynthetic ability of the tree, resulting in stunted growth. Severe infestation may cause death of trees. Efforts to control Bronze bug infection of *eucalyptus* have included attempts to isolate naturally resistant plants and natural predators. Such efforts, however, have met with limited or no success.

Certain characteristics of Bronze bug infestations lead to difficulties in controlling infestations with chemical pesticides. Bronze bug infestations tend to spread rapidly. Control of infestation would thus necessitate repeated spraying. Bronze bug, moreover, tend to aggregate in the mid-canopy, which is difficult to penetrate with insecticides. Even if feasible, chemical pesticide control has disadvantages. Chemical pesticides are potentially detrimental to the environment, are not selective and are potentially harmful to non-target crops and fauna. Chemical pesticides persist in the environment and generally are metabolized slowly, or not at all. Chemical pesticides accumulate in the food chain, particularly in the higher predator species where they can act as mutagens and/or carcinogens to cause irreversible and deleterious genetic modifications. Crop pests, moreover, may develop resistance against chemical insecticides because of repetitive usage of the same insecticide or of insecticides having the same mode of action.

RNA interference or "RNAi" is a process of sequence-specific down-regulation of gene expression (also referred to as "gene silencing" or "RNA-mediated gene silencing") initiated by double-stranded RNA (dsRNA) that is complementary in sequence to a region of the target gene to be down-regulated. Down-regulation of target genes in multi-cellular organisms by means of RNA interference (RNAi) has become a well-established technique. U.S. patent application publications US 2009/0285784 A1 and US 2009/0298787 relate to dsRNA as an insect control agent and are hereby incorporated herein by reference in their respective entireties. U.S. Pat. No. 6,506,559, U.S. patent application publication 2003/00150017 A1, International Publications WO 00/01846, WO 01/37654, WO 2005/019408, WO 2005/049841, WO 05/047300 relate to the use of RNAi to protect plants against insects. International application, PCT/US12/31423, filed Mar. 30, 2012, relates to RNA-mediated control of *eucalyptus* pests in the Gall Wasp family. Each of the foregoing patents and published applications is hereby incorporated by reference in its entirety.

SUMMARY

The present invention is based, in part, on the inventors' sequencing of genes from the *eucalyptus* Bronze bug invasive species, *Thaumastocoris peregrinus* (hereinafter "Tp" or "Bronze bug"). In certain aspects, the invention thus provides Bronze bug nucleic acids, derivatives thereof and the use of such nucleic acids and derivatives as Bronze bug control agents.

In certain aspects the invention provides isolated nucleic acids that hybridize selectively under high stringency hybridization conditions to a sequence set out in SEQ ID NO: 1-59 and 74-87 and complementary sequences thereof.

In certain aspects the invention provides isolated nucleic acids that are 90-99.99 percent identical to sequences set out in SEQ ID NO: 1-59 and 74-87 and complementary sequences thereof.

In certain aspects the invention provides isolated nucleic acids that include at least 17 contiguous nucleotides of the sequences set out in SEQ ID NO: 1-59 and 74-87 and complementary sequences thereof.

In certain aspects the invention provides nucleic acids from Bronze bug, including the nucleic acids set out above, that are about 80% or less identical to the honey bee ortholog of said nucleic acid.

In certain aspects the invention provides vectors that include nucleic acids from Bronze bug, or reverse compliments of such sequences, operably linked to an expression control sequence.

In certain aspects the invention provides host cells transformed with and/or harboring vectors that include nucleic acids from Bronze bug, or reverse compliments of such sequences, operably linked to an expression control sequence.

In certain aspects the invention provides plant tissues, for example, leaf tissue and seeds, transformed with and/or harboring vectors that include nucleic acids from Bronze bug operably linked to an expression control sequence.

In certain aspects the invention provides isolated small inhibitory ribonucleic acid (siRNA) molecules that inhibit expression of Bronze bug nucleic acids.

In certain aspects the invention provides isolated double stranded ribonucleic acid (dsRNA) molecules that include a first strand of nucleotides that is substantially identical to at least 17 contiguous nucleotides of SEQ ID NO: 1-59 and 74-87 and a second strand of nucleotides that is substantially complementary to the first strand of nucleotides.

In certain aspects the invention provides double stranded ribonucleic acid (dsRNA) molecules with a high level of homology (greater than 80%) to mRNA from Bronze bug (Bronze bug targeting dsRNAs), including the dsRNA molecules set out above, that are about 80% or less identical to the honey bee ortholog of the dsRNA.

In certain aspects the invention provides vectors that include an expression control sequence operatively linked to a nucleotide sequence that is a template for one or both strands of a dsRNA from Bronze bug.

In certain aspects the invention provides host cells transformed with and/or harboring vectors that include an expression control sequence operatively linked to a nucleotide sequence that is a template for one or both strands of a dsRNA from Bronze bug.

In certain aspects the invention provides plant tissue transformed with and/or harboring vectors that include an expression control sequence operatively linked to a nucleotide sequence that is a template for one or both strands of a dsRNA from Bronze bug.

In certain aspects the invention provides isolated small inhibitory ribonucleic acid (siRNA) molecules that inhibit expression of an essential gene of Bronze bug.

In certain aspects the invention provides methods of producing a pest resistant plant by expressing a Bronze bug dsRNA in the plant or in propagative or reproductive material of the plant.

In certain aspects the invention provides methods of producing pest resistant *eucalyptus* by expressing a Bronze bug dsRNA in the *eucalyptus* or in propagative or reproductive material of the *eucalyptus*.

In certain aspects the invention provides methods of producing *eucalyptus* resistant to Bronze bug infection and/or infestation by expressing a Bronze bug targeting dsRNA in the *eucalyptus* or in propagative or reproductive material of the *eucalyptus*.

In certain aspects the invention provides methods of producing a plant resistant to a plant pathogenic pest by transforming a plant cell with a recombinant DNA construct or combination of constructs that express a dsRNA; regenerating a plant from the transformed plant cell; and growing the transformed plant cell under conditions suitable for the expression of the recombinant DNA construct.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 schematically depicts certain, non-limiting nucleic acids according to the invention. (A) Schematic of silencing construct #3, constructed from sequences from three Bronze bug genes in accordance with the general scheme depicted in FIG. 1 (B) Schematic of hpRNA molecule produced by transcription of transgene P1 to T1. (C) Schematic of mRNA produced by transcription of transgene P2 to T2. Definitions: P1—CaMV 35S Promoter (SEQ ID NO: 60); P2—sgFIMV Promoter (SEQ ID NO: 61); T1—AtActin7 Terminator (SEQ ID NO: 62); T2—Nos Terminator (SEQ ID NO: 63); Bb41—SEQ ID NO: 46; Bb53-SEQ ID NO: 52; Bb54—SEQ ID NO: 54 L—loop sequence site (SEQ ID NO: 64).

FIG. 6 schematically depicts certain, non-limiting nucleic acids according to the invention. (A) Schematic of silencing construct constructed using sequences from two Bronze bug genes. Transgene P1 to T1 encodes a hairpin RNA (hpRNA) for silencing Bronze bug, constructed by fusing 100 bp from each of two different Bronze bug genes, by, synthesizing the resulting sequence as an inverted repeat, and inserting a loop sequence between the respective sense and inverted repeat sequences. Transgene P2 to T2 encodes an mRNA with the respective fused 100 bp sequences from the two Bronze bug genes. mRNA transcribed from transgene P2 to T2 is the template for cytoplasmic enhancement of the silencing signal. (B) Schematic of hpRNA molecule produced by transcription of transgene P1 to T1. (C) Schematic of mRNA produced by transcription of transgene P2 to T2.

Like reference symbols in the various drawings indicate like elements.

DETAILED DESCRIPTION

Figure 1A:
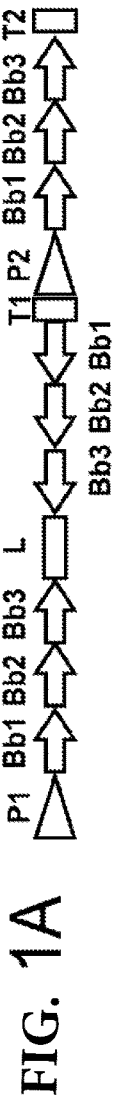
FIG. 1 schematically depicts certain, non-limiting nucleic acids according to the invention. (A) Schematic of silencing construct constructed using sequences from three Bronze bug genes. Transgene P1 (Promoter 1) to T1 (Termination sequence 1) encodes a hairpin RNA (hpRNA), constructed by fusing 100 bp from each of three different Bronze bug genes (Bb1, Bb2 and Bb3), by synthesizing the resulting sequence as an inverted repeat, and inserting a loop sequence between the respective sense and inverted repeat sequences. Transgene P2 (Promoter 2) to T2 (termination sequence 2) encodes an mRNA with the respective fused 100 bp sequences from the three Bronze bug genes. mRNA transcribed from transgene P2 to T2 is the template for cytoplasmic enhancement of the silencing signal. (B) Schematic of hpRNA molecule produced by transcription of transgene P1 to T1. (C) Schematic of mRNA produced by transcription of transgene P2 to T2.

The inventors have conducted transcriptome sequencing of the natural *eucalyptus* pest, Bronze bug *Thaumastocoris peregrinus* (Tp) and mined the respective transcriptomes to identify open reading frames Bronze bug genes that correspond to Bronze bug mRNAs. The identification of Bronze bug RNAs allows for the design of siRNA and dsRNA that mediate downregulation (silencing) of Bronze bug genes. Such siRNA and dsRNAs are thus useful as biological control agents to kill or inhibit the development of Bronze bug and inhibit Bronze bug infection of plants.

Accordingly, the present invention describes a nucleic acid based approach for the control of Bronze bug pests. Such nucleic acid based approaches include, without limitation, approaches based on expression of Bronze bug double-stranded (dsRNA), antisense RNA, and mRNA.

The methods of the invention find practical application in any area of technology where it is desirable to inhibit viability, growth, development or reproduction of Bronze bugs, or to decrease pathogenicity or infectivity of the insect. The methods of the invention further find practical application where it is desirable to specifically down-regulate expression of one or more target genes in a Bronze bug insect. Particularly useful practical applications include, but are not limited to, protecting plants against Bronze bug pest infestation.

In certain aspects, an active ingredient for controlling Bronze bug infestation is a double-stranded RNA (dsRNA) or a nucleic acid that can promote or lead to production of a dsRNA, which can be used as an insecticidal formulation. dsRNA can be expressed in a host plant, plant part, plant cell or seed to protect the plant against Bronze bugs. The sequence of the dsRNA corresponds to part or whole of an essential Bronze bug gene and causes downregulation of the insect target gene via RNA interference (RNAi). As a result of the downregulation of mRNA, the dsRNA prevents expression of the target insect protein and causes death, growth arrest or sterility of the insect. In this aspect, siRNA control of insect growth, for preventing insect infestation of a cell or a plant susceptible to insect infection, is effected by contacting insects with a dsRNA produced by annealed complementary strands, one of which has a nucleotide sequence which is complementary to at least part of the nucleotide sequence of an insect target gene. dsRNA is expressed in plant tissue that is ingested by the insect and then taken up by the insect through the gut, and thereby controls growth or prevents infestation. See Huvenne et al., 2010, *J Insect Physiol* 56: 227-35.

Bronze bug target genes for siRNA-mediated intervention include are preferably non-redundant, vital genes. Vital target genes may be any gene that when inhibited interferes with growth or survival or pathogenicity or infectivity of the insect. Such vital target genes are essential for viability, growth, development or reproduction of the insect, or any gene that is involved with pathogenicity or infectivity of the insect, such that specific inhibition of the target gene leads to a lethal phenotype or decreases or stops insect infestation. Down regulation of such vital target genes, whose activity cannot be complemented by other related genes, results in significant damage to the pest larvae and provides an efficient pest control system for sessile Bronze bug pests. The target gene may be any of the target genes herein described, for instance a target gene that is essential for the viability, growth, development or reproduction of the pest. Examples of target genes include, for example, genes that are involved in protein synthesis and/or metabolism and/or RNA synthesis and metabolism and/or cellular processes. A slight knockdown of these target genes will have an effect on many other genes and processes ultimately leading to a lethal effect on the target pest. Such a down-regulated target gene will result in the death of the insect, or the reproduction or growth of the insect being stopped or delayed. Such target genes are vital for the viability of the insect and are referred to as vital genes.

Potential target genes may be identified based on homologies to genes in other insect species. Published genome-wide RNAi mediated gene interference libraries (15, 16) may be used to identify genes that are lethal to other organisms when RNAi based on these genes is expressed and incorporated into target pest organisms by ingestion or any other means. Thus genes identified as being RNAi-lethal in *Drosophila* may be used to screen for orthologs in hymenoptera species. Such hymenoptera orthologs may further be used to screen Bronze bug species for potential targets.

Adult Bronze bug insects live for approximately 40 days. Females can produce at least 60 eggs during that time period (2 per day for 30 days). Eggs may be deposited singly or in clusters and may be deposited anywhere on a tree, but are typically deposited in clusters on leaves. The laying of virgin eggs is reported for this genus. At 17-22° C. the eggs hatch in approximately six days. Bronze bug development progresses through five stadia, taking approximately 4.6, 3.5, 3.3, 3.7 and 5.3 days, respectively. Bronze bug may be induced, e.g., by agitation, to lay eggs on unnatural surfaces, for example, the side of a vial.

Nucleotide sequences of Bronze bug target genes include, for example, the sequences set out in SEQ ID NO: 1-59 and 74-87 the complements of such sequences, the reverse complements of such sequences, and sequences that selectively hybridize to such sequences and complements under high stringency hybridization conditions. Examples of target genes include, without limitation, AMP, WD40, TEF, ETI, RNA_HEL, UBIQ_LIG, Mor and TIF.

Nucleotide sequences useful for dsRNA-mediated down-regulation of Bronze bug target genes include, for example, (i) a sequences set out in SEQ ID NO: 1-59 and 74-87 and the complements of such sequences; (ii) sequences which are at least 70%, 75%, 80%, 85%, 90%, 95%, 96%, 97%, 98%, 99% or 99.9% identical to a sequence set out in SEQ ID NO: 1-59 and 74-87 and the complements of such sequences; (iii) sequences comprising at least 17 contiguous nucleotides of SEQ ID NO: 1-59 and 74-87 and the complements of such sequences; and (iv) sequences that selectively hybridize to such sequences and complements under high stringency hybridization conditions.

An "isolated" nucleic acid as used herein is a nucleic that has been identified and separated and/or recovered from a component of its natural environment.

"Controlling pests" as used herein means killing pests, or preventing pests to develop, or to grow or preventing pests to infect or infest. Controlling pests as used herein also encompasses controlling pest progeny (development of eggs). Controlling pests as used herein also encompasses inhibiting viability, growth, development or reproduction of the pest, or to decrease pathogenicity or infectivity of the pest. The compounds and/or compositions described herein, may be used to keep an organism healthy and may be used curatively, preventively or systematically to control pests or to avoid pest growth or development or infection or infestation.

Particular pests envisaged for control by methods described herein are plant pathogenic insect pests. "Controlling insects" as used herein thus encompasses controlling insect progeny (such as development of eggs). Controlling insects as used herein also encompasses inhibiting viability, growth, development or reproduction of the insect, or decreasing pathogenicity or infectivity of the insect. As used herein, controlling insects may refer to inhibiting a biological activity in an insect, resulting in one or more of the following attributes: reduction in feeding by the insect, reduction in viability of the insect, death of the insect, inhibition of differentiation and development of the insect, absence of or reduced capacity for sexual reproduction by the insect.

The compounds and/or compositions described herein, may be used to keep an organism healthy and may be used curatively, preventively or systematically to control an insect or to avoid insect growth or development or infection or infestation. Thus, the invention may allow previously susceptible organisms to develop resistance against infestation by the insect organism.

The term "complementary to at least part of" refers to a nucleotide sequence that is fully complementary to the nucleotide sequence of the target over more than ten nucleotides, for instance over at least 15, 16, 17, 18, 19, 20, 21, 22, 23, 24 or more contiguous nucleotides. Notwithstanding the above, "complementary to at least part" of may also include complementary sequences that are greater than 80% complementary to a nucleotide sequence of a target sequence over a length of more than 20 nucleotides, for instance over at least 20, 21, 22, 23, 24 or more contiguous nucleotides [13, 14].

In certain aspects, the invention provides a method for down-regulating expression of a target gene in an insect, comprising contacting the insect with a dsRNA, wherein the dsRNA comprises annealed complementary strands, one of which has a nucleotide sequence that is complementary to at least part of the nucleotide sequence of the insect target gene to be down-regulated, whereby the dsRNA is taken up into the insect and thereby down-regulates expression of the insect target gene.

The term "insect" encompasses insects of all types and at all stages of development, including egg, larval or nymphal, pupal and adult stages.

As used herein, the term "plant" encompasses any plant material that it is desired to treat to prevent or reduce insect growth and/or insect infestation. This includes, inter alia, whole plants, seedlings, propagation or reproductive material such as seeds, cuttings, grafts, explants, etc., and also plant cell and tissue cultures. The plant material should express, or have the capability to express, the RNA molecule comprising at least one nucleotide sequence that is the RNA complement of or that represents the RNA equivalent of at least part of the nucleotide sequence of the sense strand of at least one target gene of the pest organism, such that the RNA molecule is taken up by a pest upon plant-pest interaction, said RNA molecule being capable of inhibiting the target gene or down-regulating expression of the target gene by RNA interference.

The terms "down-regulation of gene expression" and "inhibition of gene expression" are used interchangeably and refer to a measurable or observable reduction in gene expression or a complete abolition of detectable gene expression, at the level of protein product and/or mRNA product from the target gene. The down-regulation effect of the dsRNA on gene expression may be calculated as being at least 30%, 40%, 50%, 60%, preferably 70%, 80% or even more preferably 90% or 95% when compared with normal gene expression. Depending on the nature of the target gene, down-regulation or inhibition of gene expression in cells of an insect can be confirmed by phenotypic analysis of the cell or the whole insect or by measurement of mRNA or protein expression using molecular techniques such as RNA solution hybridization, PCR, nuclease protection, Northern hybridization, reverse transcription, gene expression monitoring with a microarray, antibody binding, enzyme-linked immunosorbent assay (ELISA), Western blotting, radioimmunoassay (RIA), other immunoassays, or fluorescence-activated cell analysis (FACS).

Down-regulation of an essential gene leads to growth inhibition. Depending on the assay used, the growth inhibition can be quantified as being greater than about 5%, 10%, more preferably about 20%, 25%, 33%, 50%, 60%, 75%, 80%, most preferably about 90%, 95%, or about 99% as compared to a pest organism that has been treated with control dsRNA.

The "target gene" may be essentially any gene that is desirable to be inhibited because it interferes with growth or pathogenicity or infectivity of the insect. For instance, if the method of the invention is to be used to prevent insect growth and/or infestation then it is preferred to select a target gene which is essential for viability, growth, development or reproduction of the insect, or any gene that is involved with pathogenicity or infectivity of the insect, such that specific inhibition of the target gene leads to a lethal phenotype or decreases or stops insect infestation.

According to one non-limiting embodiment, the target gene is such that when its expression is down-regulated or inhibited using the method of the invention, the insect is killed, or the reproduction or growth of the insect is stopped or retarded. This type of target gene is considered to be essential for the viability of the insect and is referred to as essential genes. Therefore, the present invention encompasses a method as described herein, wherein the target gene is an essential gene.

Without being bound by theory, the target gene is such that when it is down-regulated the infestation or infection by the insect, the damage caused by the insect, and/or the ability of the insect to infest or infect host organisms and/or cause such damage, is reduced. The terms "infest" and "infect" or "infestation" and "infection" are generally used interchangeably throughout. This type of target genes is considered to be involved in the pathogenicity or infectivity of the insect. Therefore, the present invention extends to methods as described herein, wherein the target gene is involved in the pathogenicity or infectivity of the insect. The advantage of choosing the latter type of target gene is that the insect is blocked to infect further plants or plant parts and is inhibited to form further generations.

In dsRNA-mediated methods of controlling growth or infestation of a specific insect in or on a host cell or host organism, it is preferred that the dsRNA does not share any significant homology with any host gene, or at least not with any essential gene of the host. In this context, it is preferred that the dsRNA shows less than 30%, more preferably less that 20%, more preferably less than 10%, and even more preferably less than 5% nucleic acid sequence identity with any gene of the host cell. Percent sequence identity should be calculated across the full length of the dsRNA region. If genomic sequence data is available for the host organism one may cross-check sequence identity with the dsRNA using standard bioinformatics tools. In one embodiment, there is no sequence identity between the dsRNA and a host sequences over 21 contiguous nucleotides, meaning that in this context, it is preferred that 21 contiguous base pairs of the dsRNA do not occur in the coding sequences (CDS) of the host organism. In another embodiment, there is less than about 10% or less than about 12.5% sequence identity over 24 contiguous nucleotides of the dsRNA with any nucleotide sequence from a host species.

dsRNA comprises annealed complementary strands, one of which has a nucleotide sequence which corresponds to a target nucleotide sequence of the target gene to be down-regulated. The other strand of the dsRNA is able to base-pair with the first strand.

The expression "target region" or "target nucleotide sequence" of the target insect gene may be any suitable region or nucleotide sequence of the gene. The target region should comprise at least 17, at least 18 or at least 19 consecutive nucleotides of the target gene, more preferably at least 20 or at least 21 nucleotide and still more preferably at least 22, 23 or 24 nucleotides of the target gene.

It is preferred that (at least part of) the dsRNA will share 100% sequence identity with the target region of the insect target gene. However, it will be appreciated that 100% sequence identity over the whole length of the double stranded region is not essential for functional RNA inhibition. RNA sequences with insertions, deletions, and single point mutations relative to the target sequence have also been found to be effective for RNA inhibition.

The terms "corresponding to" or "complementary to" are used herein interchangeably, and when these terms are used to refer to sequence correspondence between the dsRNA and the target region of the target gene, they are to be interpreted accordingly, i.e., as not absolutely requiring 100% sequence identity. However, the percent sequence identity between the dsRNA and the target region will generally be at least 80% or 85% identical, preferably at least 90%, 95%, 96%, or more preferably at least 97%, 98% and still more preferably at least 99%. Two nucleic acid strands are "substantially complementary" when at least 85% of their bases pair.

The term "complementary" as used herein relates to all of DNA-DNA complementarity, RNA-RNA complementarity and to DNA-RNA complementarity. In analogy herewith, the term "RNA equivalent" substantially means that in the DNA sequence(s), the base "T" may be replaced by the corresponding base "U" normally present in ribonucleic acids.

Although dsRNA contains a sequence which corresponds to the target region of the target gene, it is not essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

The dsRNA may contain one or more substitute bases in order to optimize performance in RNAi. It will be apparent to one of ordinary skill in the art how to vary each of the bases of the dsRNA in turn and test the activity of the resulting dsRNAs (e.g., in a suitable in vitro test system) in order to optimize the performance of a given dsRNA.

The dsRNA may further contain DNA bases, non-natural bases or non-natural backbone linkages or modifications of the sugar-phosphate backbone, for example to enhance stability during storage or enhance resistance to degradation by nucleases.

Interfering RNAs (siRNAs) of about 21 bp are useful for effective gene silencing. Increasing the length of dsRNA preferably to at least about 80-100 bp may increase the efficiency by which dsRNA is taken up by pest organisms. Such longer fragments may be more effective in gene silencing, possibly due to a more efficient uptake of these long dsRNA by the invertebrate.

RNA duplexes consisting of either 27-mer blunt or short hairpin (sh) RNAs with 29 bp stems and 2-nt 3' overhangs may also be used as siRNAs. Thus, molecules based upon the targets identified above and being either 27-mer blunt or short hairpin (sh) RNA's with 29-bp stems and 2-nt 3' overhangs are also included within the scope of the invention.

Therefore, in one embodiment, the dsRNA fragment (or region) will itself preferably be at least 17 bp in length, preferably 18 or 19 bp in length, more preferably at least 20 bp, more preferably at least 21 bp, or at least 22 bp, or at least 23 bp, or at least 24 bp, 25 bp, 26 bp or at least 27 bp in length. The expressions "double-stranded RNA fragment" or "double-stranded RNA region" refer to a small entity of the dsRNA corresponding with (part of) the target gene.

More generally, the double stranded RNA is preferably between about 17-1500 bp, even more preferably between about 80-1000 bp and most preferably between about 17-27 bp or between about 80-250 bp; such as double stranded RNA regions of about 17 bp, 18 bp, 19 bp, 20 bp, 21 bp, 22 bp, 23 bp, 24 bp, 25 bp, 27 bp, 50 bp, 80 bp, 100 bp, 150 bp, 200 bp, 250 bp, 300 bp, 350 bp, 400 bp, 450 bp, 500 bp, 550 bp, 600 bp, 650 bp, 700 bp, 900 bp, 100 bp, 1100 bp, 1200 bp, 1300 bp, 1400 bp or 1500 bp.

The upper limit on the length of the dsRNA may be dependent on i) the requirement for the dsRNA to be taken up by the insect and ii) the requirement for the dsRNA to be processed within the cell into fragments that direct RNAi. The chosen length may also be influenced by the method of synthesis of the RNA and the mode of delivery of the RNA to the cell. Preferably the dsRNA to be used in the methods of the invention will be less than 10,000 bp in length, more preferably 1000 bp or less, more preferably 500 bp or less, more preferably 300 bp or less, more preferably 100 bp or less. For any given target gene and insect, the optimum length of the dsRNA for effective inhibition may be determined by experiment.

The dsRNA may be fully or partially double-stranded. Partially dsRNAs may include short single-stranded overhangs at one or both ends of the double-stranded portion, provided that the RNA is still capable of being taken up by insects and directing RNAi. The dsRNA may also contain internal non-complementary regions.

The methods of the invention encompass the simultaneous or sequential provision of two or more different dsRNAs or RNA constructs to the same insect, so as to achieve down-regulation or inhibition of multiple target genes or to achieve a more potent inhibition of a single target gene.

Alternatively, multiple targets are hit by the provision of one dsRNA that hits multiple target sequences, and a single target is more efficiently inhibited by the presence of more than one copy of the double stranded RNA fragment corresponding to the target gene. Thus, in certain aspects, a dsRNA construct comprises multiple dsRNA regions, at least one strand of each dsRNA region comprising a nucleotide sequence that is complementary to at least part of a target nucleotide sequence of an insect target gene. The dsRNA regions in the RNA construct may be complementary to the same or to different target genes and/or the dsRNA regions may be complementary to targets from the same or from different insect species.

The terms "hit", "hits" and "hitting" are alternative wordings to indicate that at least one of the strands of the dsRNA is complementary to, and as such may bind to, the target gene or nucleotide sequence.

In one embodiment, the double stranded RNA region comprises multiple copies of the nucleotide sequence that is complementary to the target gene. Alternatively, the dsRNA hits more than one target sequence of the same target gene. The invention thus encompasses isolated double stranded RNA constructs comprising at least two copies of said nucleotide sequence complementary to at least part of a nucleotide sequence of an insect target.

The term "multiple" as used herein means at least two, at least three, at least four, at least five, at least six, etc.

The expressions "a further target gene" or "at least one other target gene" mean for instance a second, a third or a fourth, etc. target gene.

dsRNA that hits more than one of the above-mentioned targets, or a combination of different dsRNA against different of the above mentioned targets are developed and used in the methods of the present invention.

dsRNA regions (or fragments) in the double stranded RNA may be combined as follows: a) when multiple dsRNA regions targeting a single target gene are combined, they may be combined in the original order (i.e., the order in which the regions appear in the target gene) in the RNA construct; b) alternatively, the original order of the fragments may be ignored so that they are scrambled and combined randomly or deliberately in any order into the double stranded RNA construct; c) alternatively, one single fragment may be repeated several times, for example from 1 to 10 times, e.g., 1, 2, 3, 4, 5, 6, 7, 8, 9 or 10 times, in the ds RNA construct, or d) the dsRNA regions (targeting a single or different target genes) may be combined in the sense or antisense orientation.

Multiple dsRNA regions targeting a single or different weak gene(s) may be combined to obtain a stronger RNAi effect. "Insect specific" genes or sequences, e.g., Bronze bug specific, particularly Bronze bug specific genes and sequences, encompass genes that have no substantial homologous counterpart in non-insect organisms as can be determined by bioinformatics homology searches, for example by BLAST searches. The choice of a specific target gene results in a species specific RNAi effect, with no effect or no substantial (adverse) effect in non-target organisms. "Conserved genes" encompass genes that are conserved (at the amino acid level) between the target organism and non-target organism(s). To reduce possible effects on non-target species, such effective but conserved genes are analyzed and target sequences from the variable regions of these conserved genes are chosen to be targeted by the dsRNA regions in the RNA construct. Conservation is assessed at the level of the nucleic acid sequence. Such variable regions thus encompass the least conserved sections, at the level of the nucleic acid sequence, of the conserved target gene(s). The RNA constructs according to the present invention target multiple genes from different biological pathways, resulting in a broad cellular RNAi effect and more efficient insect control. In certain embodiments dsRNAs are constructed from sequences, e.g., Bronze bug transcriptome sequences, that are equal to or less than 80% identical to the sequence of a honey bee ortholog.

In certain aspects, dsRNA constructs are constructed with gene sequences that affect different classes of cellular functions. Examples of such classes of cellular function include, without limitation, (i) protein synthesis and metabolism, (ii) RNA synthesis and metabolism, and (iii) cellular processes. In certain embodiments, dsRNA constructs comprise sequences from each of the aforementioned claims, i.e., three classes. In certain embodiments, dsRNA constructs comprise sequences from two of the aforementioned classes, e.g., protein synthesis and metabolism and RNA synthesis and metabolism; protein synthesis and cellular processes; or RNA synthesis and metabolism and cellular processes.

dsRNA regions comprise at least one strand that is complementary to at least part or a portion of the nucleotide sequence of any of the target genes herein described. However, provided one of the double stranded RNA regions comprises at least one strand that is complementary to a portion of the nucleotide sequence of any one of the target genes herein described, the other double stranded RNA regions may comprise at least one strand that is complementary to a portion of any other insect target gene (including known target genes).

In some constructs, dsRNAs may comprise additional sequences and optionally a linker. Additional sequences may include, for example, (i) a sequence facilitating large-scale production of the dsRNA construct; (ii) a sequence effecting an increase or decrease in the stability of the dsRNA; (iii) a sequence allowing the binding of proteins or other molecules to facilitate uptake of the RNA construct by insects; (iv) a sequence which is an aptamer that binds to a receptor or to a molecule on the surface or in the cytoplasm of an insect to facilitate uptake, endocytosis and/or transcytosis by the insect; or (v) additional sequences to catalyze processing of dsRNA regions. In one embodiment, the linker is a conditionally self-cleaving RNA sequence, preferably a pH sensitive linker or a hydrophobic sensitive linker.

Multiple dsRNA regions of the dsRNA construct may be connected directly or by one or more linkers. A linker may be present at a site in the RNA construct, separating dsRNA regions from another region of interest. Multiple dsRNA regions of dsRNA constructs may be connected without linkers.

When present, linkers may be used to disconnect smaller dsRNA regions in the pest organism. Advantageously, in this situation the linker sequence may promote division of a long dsRNA into smaller dsRNA regions under particular circumstances, resulting in the release of separate dsRNA regions under these circumstances and leading to more efficient gene silencing by these smaller dsRNA regions. Examples of suitable conditionally self-cleaving linkers are RNA sequences that are self-cleaving at high pH conditions. Suitable examples of such RNA sequences are described by Borda et al. (Nucleic Acids Res. 2003 May 15; 31(10):2595-600), which document is incorporated herein by reference. This sequence originates from the catalytic core of the hammerhead ribozyme HH16.

Linkers may also be located at a site in the dsRNA construct, separating the dsRNA regions from another, e.g., an additional, sequence of interest, which preferably provides some additional function to the RNA construct.

dsRNA constructs may include aptamers to facilitate uptake of the dsRNA by the insect. The aptamer is designed to bind a substance which is taken up by the insect. Such substances may be from an insect or plant origin. One specific example of an aptamer, is an aptamer that binds to a transmembrane protein, for example a transmembrane protein of an insect. Alternatively, the aptamer may bind a (plant) metabolite or nutrient which is taken up by the insect.

Linkers may undergo self-cleaving in the endosome. This may be advantageous when the constructs of the present invention are taken up by the insect via endocytosis or transcytosis, and are therefore compartmentalized in the endosomes of the insect species. The endosomes may have a low pH environment, leading to cleavage of the linker.

Linkers that are self-cleaving in hydrophobic conditions are particularly useful in dsRNA constructs when used to be transferred from one cell to another via the transit in a cell wall, for example when crossing the cell wall of an insect pest organism.

An intron may be used as a linker. An "intron" as used herein may be any non-coding RNA sequence of a messenger RNA.

A non-complementary RNA sequence, ranging from about 1 base pair to about 10,000 base pairs, may also be used as a linker.

Without wishing to be bound by any particular theory or mechanism, it is thought that long dsRNAs are taken up by the insect from their immediate environment. dsRNAs taken up into the gut and transferred to the gut epithelial cells are then processed within the cell into short dsRNAs, called small interfering RNAs (siRNAs), by the action of an endogenous endonuclease. The resulting siRNAs then mediate RNAi via formation of a multi-component RNase complex termed the RISC or RNA interfering silencing complex.

In order to achieve down-regulation of a target gene within an insect cell the dsRNA added to the exterior of the cell wall may be any dsRNA or dsRNA construct that can be taken up into the cell and then processed within the cell into siRNAs, which then mediate RNAi, or the RNA added to the exterior of the cell could itself be an siRNA that can be taken up into the cell and thereby direct RNAi.

siRNAs are generally short dsRNAs having a length in the range of from 19 to 25 base pairs, or from 20 to 24 base pairs. In preferred embodiments siRNAs having 19, 20, 21, 22, 23, 24 or 25 base pairs, and in particular 21 or 22 base pairs, corresponding to the target gene to be down-regulated may be used. However, the invention is not intended to be limited to the use of such siRNAs.

siRNAs may include single-stranded overhangs at one or both ends, flanking the double-stranded portion. The siRNA may contain 3' overhanging nucleotides, preferably two 3' overhanging thymidines (dTdT) or uridines (UU). 3' TT or UU overhangs may be included in the siRNA if the sequence of the target gene immediately upstream of the sequence included in double-stranded part of the dsRNA is AA. This allows the TT or UU overhang in the siRNA to hybridize to the target gene. Although a 3' TT or UU overhang may also be included at the other end of the siRNA it is not essential for the target sequence downstream of the sequence included in double-stranded part of the siRNA to have AA. In this context, siRNAs which are RNA/DNA chimeras are also contemplated. These chimeras include, for example, the siRNAs comprising a dsRNA with 3' overhangs of DNA bases (e.g., dTdT), as discussed above, and also dsRNAs which are polynucleotides in which one or more of the RNA bases or ribonucleotides, or even all of the ribonucleotides on an entire strand, are replaced with DNA bases or deoxyribonucleotides.

dsRNA may be formed from two separate (sense and antisense) RNA strands that are annealed together by (non-covalent) base pairing. Alternatively, the dsRNA may have a foldback stem-loop or hairpin structure, wherein the two annealed strands of the dsRNA are covalently linked. In this embodiment the sense and antisense stands of the dsRNA are formed from different regions of single polynucleotide molecule that is partially self-complementary. RNAs having this structure are convenient if the dsRNA is to be synthesized by expression in vivo, for example in a host cell or organism, or by in vitro transcription. The precise nature and sequence of the "loop" linking the two RNA strands is generally not material to the invention, except that it should not impair the ability of the double-stranded part of the molecule to mediate RNAi. The features of "hairpin" or "stem-loop" RNAs for use in RNAi are generally known in the art (see for example WO 99/53050, the contents of which are incorporated herein by reference). In other embodiments of the invention, the loop structure may comprise linker sequences or additional sequences as described above. In certain aspects, the Bronze bug sequences disclosed herein and the complements of such sequences may also be used to inhibit expression of Bronze bug nucleic acids via expression of antisense RNA or overexpression of sense RNA, using methods well known in the art. See, e.g., Frizzi et al., Plant Biotech J, (2010) 8:655-677; Brodersen et al., Trends in Genetics, (2008) 22:268-280; and U.S. Pat. No. 5,759,829. Using expression elements, vectors and methods described herein, antisense RNAs or sense RNAs for Bronze bug target genes are expressed in *eucalyptus* plants. Upon ingestion by Bronze bug pests, the antisense or sense RNAs inhibit expression of the target genes to control pest infestation.

Target nucleotide sequences for design the dsRNA constructs are preferably at least 17, preferably at least 18, 19, 20 or 21, more preferably at least 22, 23 or 24 nucleotides in length. Non-limiting examples of preferred target nucleotide sequences are given in the examples.

Target sequences may include sequences that are homologous to sequences disclosed herein. Homologues of target genes can be found using methods well known to those of ordinary skill in the art. Preferred homologues are genes comprising a sequence which is at least about 85% or 87.5%, still more preferably about 90%, still more preferably at least about 95% and most preferably at least about 99% or 99.9% identical to a sequence disclosed herein, or the complement thereof. Methods for determining sequence identity are routine in the art and include use of the Blast software and EMBOSS software (The European Molecular Biology Open Software Suite (2000), Rice, P. Longden, I. and Bleasby, A. Trends in Genetics 16, (6) pp 276-277). The term "identity" as used herein refers to the relationship between sequences at the nucleotide level. The expression "% identical" is determined by comparing optimally aligned sequences, e.g., two or more, over a comparison window wherein the portion of the sequence in the comparison window may comprise insertions or deletions as compared to the reference sequence for optimal alignment of the sequences. The reference sequence does not comprise insertions or deletions. The reference window is chosen from between at least 10 contiguous nucleotides to about 50, about 100 or to about 150 nucleotides, preferably between about 50 and 150 nucleotides. "percent identity" is then calculated by determining the number of nucleotides that are identical between the sequences in the window, dividing the number of identical nucleotides by the number of nucleotides in the window and multiplying by 100.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) Anal. Biochem., 138:267-84: $T_m=81.5°$ C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, Laboratory Techniques in Biochemistry and Molecular Biology—Hybridization with Nucleic Acid Probes, part I, chapter 2, "Overview of principles of hybridization and the strategy of nucleic acid probe assays," Elsevier, N.Y. (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

dsRNA may be expressed by (e.g., transcribed within) a host cell or host organism. The host cell or organism may or may not be a host cell or organism susceptible or vulnerable to infestation by an insect. If the host cell or organism is a host cell or organism susceptible or vulnerable to infestation by an insect, RNAi-mediated gene silencing of one or more target genes in the insect may be used as a mechanism to control growth of the insect in or on the host organism and/or to prevent or reduce insect infestation of the host organism. Expression of the dsRNA within cells of the host organism may thus confer resistance to a particular insect or to a class of insects. In case the dsRNA hits more than one insect target gene, expression of the dsRNA within cells of the host organism may confer resistance to more than one insect or more than one class of insects.

In a preferred embodiment the host organism is a plant and the insect is a plant pathogenic insect. In this embodiment the insect is contacted with the dsRNA by expressing the dsRNA in a plant, plant tissue or plant cell that is infested with or susceptible to infestation with, or ingestion by, the plant pathogenic insect. A preferred plant host organism is *eucalyptus*. Examples of *eucalyptus* include, without limitation, the following species: *E. botryoides, E. bridgesiana, E. camaldulensis, E. cinerea, E. globule, E. grandis, E. gunii, E. nicholii, E. pulverulenta, E. robusta, E. rudis, E. saligna, E. Tereticornis, E. Urophilla, E. viminalis* and a cross hybrids of any of the preceding species especially *Eucalyptus grandis* and *Eucalyptus urophylla*. A preferred plant pathogenic insect is a Bronze bug, e.g., Bronze bug.

The term "plant" encompasses any plant material that it is desired to treat to prevent or reduce insect growth and/or insect infestation. This includes, inter alia, whole plants, seedlings, propagation or reproductive material such as seeds, cuttings, grafts, explants, etc. and also plant cell and tissue cultures. The plant material should express, or have the capability to express, dsRNA corresponding to one or more target genes of the insect.

In certain aspects the invention provides a plant, preferably a transgenic plant, or propagation or reproductive material for a (transgenic) plant, or a plant cell culture expressing or capable of expressing at least one dsRNA, wherein the dsRNA comprises annealed complementary strands, one of which has a nucleotide sequence which is complementary to at least part of a target nucleotide sequence of a target gene of an insect, such that the dsRNA is taken up by an insect upon plant-insect interaction, said double stranded RNA being capable of inhibiting the target gene or down-regulating expression of the target gene by RNA interference. The target gene may be any of the target genes herein described, for instance a target gene that is essential for the viability, growth, development or reproduction of the insect.

A plant may be provided in a form that is actively expressing (transcribing) a dsRNA in one or more cells, cell types or tissues. Alternatively, a plant may be "capable of expressing", meaning that it is transformed with a transgene which encodes the desired dsRNA but that the transgene is not active in the plant when (and in the form in which) the plant is supplied. A recombinant DNA construct comprising a nucleotide sequence encoding a dsRNA or dsRNA construct may be thus be operably linked to at least one regulatory sequence. Preferably, the regulatory sequence is selected from the group comprising constitutive promoters or tissue specific promoters as described below.

A target gene may be any target gene herein described. Preferably a regulatory element is a regulatory element that is active in a plant cell. More preferably, the regulatory element is originating from a plant. The term "regulatory sequence" is to be taken in a broad context and refers to a regulatory nucleic acid capable of effecting expression of the sequences to which it is operably linked.

Encompassed by the aforementioned term are promoters and nucleic acids or synthetic fusion molecules or derivatives thereof which activate or enhance transcription of a nucleic acid, so called activators or enhancers. The term "operably linked" as used herein refers to a functional linkage between the promoter sequence and the gene of interest, such that the promoter sequence is able to initiate transcription of the gene of interest.

By way of example, the transgene nucleotide sequence encoding the dsRNA could be placed under the control of an inducible or growth or developmental stage-specific promoter which permits transcription of the dsRNA to be turned on, by the addition of the inducer for an inducible promoter or when the particular stage of growth or development is reached.

Alternatively, the transgene encoding the dsRNA is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus (FMV) 34S promoter, cassaya vein mosaic virus (CsVMV) promoter (Verdaguer B. et al, Plant Mol. Biol. 1998 37(6):1055-67).

Alternatively, the transgene encoding the dsRNA is placed under the control of a tissue specific promoter such as any selected from the group comprising root specific promoters of genes encoding PsMTA Class III chitinase, photosynthetic tissue-specific promoters such as promoters of cab1 and cab2, rbcS, gapA, gapB and ST-LS1 proteins, JAS promoters, chalcone synthase promoter and promoter of RJ39 from strawberry.

A transgene encoding the dsRNA may also be placed under the control of an insect-induced promoter, for instance the potato proteinase inhibitor II (PinII) promoter (Duan X et al, Nat. Biotechnol. 1996, 14(4):494-8)); or a wounding-induced promoter, for instance the jasmonates and ethylene induced promoters, PDF1.2 promoter (Manners J M et al., Plant Mol. Biol. 1998, 38(6):1071-80); or under a defense related promoter, for instance the salicylic acid induced promoters and plant-pathogenesis related protein (PR protein) promoters (PR1 promoter (Cornelissen B J et al., Nucleic Acids Res. 1987, 15(17):6799-811; COMT promoter (Toquin V et. al., Plant Mol. Biol. 2003, 52(3):495-509).

When using the methods described herein for developing transgenic plants resistant against insects, it may be beneficial to place the nucleic acid encoding the dsRNA under the control of a tissue-specific promoter. In order to improve the transfer of the dsRNA from the plant cell to the pest, the plants could preferably express the dsRNA in a plant part that is first accessed or damaged by the plant pest. In case of plant pathogenic insects, preferred tissues to express the dsRNA are the leaves, stems, roots, and seeds. Therefore, in the methods disclosed herein, a plant tissue-preferred promoter may be used, such as a leaf-specific promoter, a stem-specific promoter, a phloem-specific promoter, a xylem-specific promoter, a root-specific promoter, or a seed-specific promoter (sucrose transporter gene AtSUC promoter (Baud S et al., Plant J. 2005, 43(6):824-36), wheat high molecular weight glutenin gene promoter (Robert L S et al., Plant Cell. 1989, 1(6):569-78.)).

Suitable examples of a root specific promoter are PsMTA (Fordam-Skelton, A. P., et al., 1997 Plant Molecular Biology 34: 659-668.) and the Class III Chitinase promoter. Examples of leaf- and stem-specific or photosynthetic tissue-specific promoters that are also photoactivated are promoters of two chlorophyll binding proteins (cab1 and cab2) from sugar beet (Stahl D. J., et al., 2004 BMC Biotechnology 2004 4:31), ribulose-bisphosphate carboxylase (Rubisco), encoded by rbcS (Nomura M. et al., 2000 Plant Mol. Biol. 44: 99-106), A (gapA) and B (gapB) subunits of chloroplast glyceraldehyde-3-phosphate dehydrogenase (Conley T. R. et al. 1994 Mol. Cell. Biol. 19: 2525-33; Kwon H. B. et al. 1994 Plant Physiol. 105: 357-67), promoter of the *Solanum tuberosum* gene encoding the leaf and stem specific (ST-LS1) protein (Zaidi M. A. et al., 2005 Transgenic Res. 14:289-98), stem-regulated, defense-inducible genes, such as JAS promoters (patent publication no. 20050034192/US-A1). An example of a flower-specific promoter is for instance, the chalcone synthase promoter (Faktor O. et al. 1996 Plant Mol. Biol. 32: 849) and an example of a fruit-specific promoter is for instance RJ39 from strawberry (WO 98 31812).

Other promoters useful for the expression of dsRNA are used and include, but are not limited to, promoters from an RNA PolI, an RNA PolI, an RNA PolIII, T7 RNA polymerase or SP6 RNA polymerase. These promoters are typically used for in vitro-production of dsRNA, which dsRNA is then included in an anti-insecticidal agent, for example, in an anti-insecticidal liquid, spray or powder.

The dsRNA or RNA constructs described herein may be generated by the steps of (i) contacting an isolated nucleic acid or a recombinant DNA construct with cell-free components; or (ii) introducing (e.g., by transformation, transfection or injection) an isolated nucleic acid or a recombinant DNA construct into a cell, under conditions that allow transcription of the nucleic acid or recombinant DNA construct to produce the dsRNA or RNA construct.

Optionally, one or more transcription termination sequences may also be incorporated in the recombinant construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

Recombinant constructs may further include an origin of replication which is required for maintenance and/or replication in a specific cell type. One example is when an expression construct is required to be maintained in a bacterial cell as an episomal genetic element (e.g., plasmid or cosmid molecule) in a cell. Preferred origins of replication include, but are not limited to, fl-ori and colE1 ori.

Recombinant construct may optionally include a selectable marker gene. As used herein, the term "selectable marker gene" includes any gene, which confers a phenotype on a cell in which it is expressed to facilitate the identification and/or selection of cells, which are transfected or transformed, with an expression construct of the invention. Examples of suitable selectable markers include resistance genes against ampicillin ($Amp^r$), tetracycline ($Tc^r$), kanamycin ($Kan^r$), phosphinothricin, and chloramphenicol (CAT) gene. Other suitable marker genes provide a metabolic trait, for example manA. Visual marker genes may also be used and include for example beta-glucuronidase (GUS), luciferase and Green Fluorescent Protein (GFP).

Plants that have been stably transformed with a transgene encoding the dsRNA may be supplied as seed, reproductive material, propagation material or cell culture material which does not actively express the dsRNA but has the capability to do so. The plant may be provided in a form wherein it is actively expressing (transcribing) the RNA molecule in one or more cells, cell types or tissues. Alternatively, the plant may be "capable of expressing", meaning that it is transformed with a transgene which encodes the desired RNA molecule but that the transgene is not active in the plant when (and in the form in which) the plant is supplied. Many vectors are available for this purpose, and selection of the appropriate vector will depend mainly on the size of the nucleic acid to be inserted into the vector and the particular host cell to be transformed with the vector.

General techniques for expression of exogenous dsRNA in plants for the purposes of RNAi are known in the art (see Baulcombe D, 2004, Nature. 431(7006):356-63. RNA silencing in plants, the contents of which are incorporated herein by reference). More particularly, methods for expression of dsRNA in plants for the purposes of down-regulating gene expression in plant pests such as nematodes or insects are also known in the art. Similar methods can be applied in an analogous manner in order to express dsRNA in plants for the purposes of down-regulating expression of a target gene in a plant pathogenic insect. In order to achieve this effect it is necessary only for the plant to express (transcribe) the dsRNA in a part of the plant which will come into direct contact with the insect, such that the dsRNA can be taken up by the insect. Depending on the nature of the insect and its relationship with the host plant, expression of the dsRNA could occur within a cell or tissue including the vasculature of a plant within which the insect is also present during its life cycle, or the RNA may be secreted into a space between cells, such as the apoplast, that is occupied by the insect during its life cycle. Furthermore, the dsRNA may be located in the plant cell, for example in the cytosol, or in the plant cell organelles such as a chloroplast, mitochondrion, vacuole or endoplastic reticulum. dsRNA may further be expressed in and/or transported to the phloem, e.g., leaf phloem, where it may be taken up by sap sucking pests. See Pitino et al., PLoS ONE, 6(10):e25709 (2011) and Mlotshwa et al., Plant Cell, 14:S289-S301 (2002).

During development, Bronze bug larvae are exposed to the extracellular environment including the vasculature and to intracellular contents, due to ingestion (e.g., ingestion of apoplasts) or cell lysis.

Alternatively, the dsRNA may be secreted by the plant cell and by the plant to the exterior of the plant. As such, the dsRNA may form a protective layer on the surface of the plant.

In a further aspect, the invention also provides combinations of methods and compositions for preventing or protecting plants from pest infestation. For instance, one means provides using the plant transgenic approach combining methods using expression of dsRNA molecules and methods using expression of Bt insecticidal proteins.

In a further embodiment, the invention relates to a composition for controlling insect growth and/or preventing or reducing insect infestation, comprising at least a plant part, plant cell, plant tissue or seed comprising at least one dsRNA, wherein said dsRNA comprises annealed complementary strands, one of which has a nucleotide sequence which is complementary to at least part of a nucleotide sequence of an insect target gene. Optionally, the composition further comprises at least one suitable carrier, excipient or diluent. The target gene may be any target gene described herein. Preferably the insect target gene is essential for the viability, growth, development or reproduction of the insect.

Whenever the term "a" is used within the context of "a target gene", this means "at least one" target gene. The same applies for "a" target organism meaning "at least one" target organism, and "a" RNA molecule or host cell meaning "at least one" RNA molecule or host cell.

According to one embodiment, the methods of the invention rely on uptake by the insect of dsRNA present outside of the insect (e.g., by feeding) and does not require expression of dsRNA within cells of the insect. In addition, the present invention also encompasses methods as described above wherein the insect is contacted with a composition comprising the dsRNA.

The invention further provides a method for down-regulating expression of at least one target gene in a target organism (which is capable of ingesting a plant, plant part, plant cell or seeds) comprising feeding a plant, plant part, plant cell or seed to the target organism which plant, plant part, plant cell or seed expresses dsRNA.

In a more preferred aspect, the invention provides a method for down-regulating expression of at least one target gene in a target organism (which is capable of ingesting a host cell, or extracts thereof) comprising feeding a host plant, plant part, plant cell or seed to the target organism which host plant, plant part, plant cell or seed expresses a dsRNA molecule comprising a nucleotide sequence complementary to or representing the RNA equivalent of at least part of the nucleotide sequence of the at least one target gene, whereby the ingestion of the host cell, host plant, plant part, plant cell or seed by the target organism causes and/or leads to down-regulation of expression of the at least one target gene.

The invention provides for use of a plant, plant part, plant cell or seed as defined herein for down regulation of expression of an insect target gene. In more detailed terms, the invention provides for use of a host cell as defined herein and/or an RNA molecule comprising a nucleotide sequence that is the RNA complement of or that represents the RNA equivalent of at least part of the nucleotide sequence of a target gene from a target organism, as produced by transcription of a nucleic acid molecule in a plant, plant part, plant cell or seed, for instance in the manufacture of a commodity product, for down regulation of expression of a target gene.

According to one embodiment, the methods of the invention rely on a genetically modified organism (GMO) approach wherein the dsRNA is expressed by a cell or an organism infested with or susceptible to infestation by insects. Preferably, said cell is a plant cell or said organism is a plant.

For siRNA mediated downregulation of insect genes, dsRNA is introduced and/or expressed in an insect cell, either directly or indirectly. dsRNA can be added to an insect diet artificially or produced by a transgenic source of food such as bacteria and plants [2,8]. Transgenic plants transcribing inverted repeat RNAs comprised of insect gene specific sequences, can process it to dsRNA and later into siRNA (small interfering RNA that are the first product in the silencing pathway). Insects digesting such transgenic plants are affected by the plant synthesized dsRNA and siRNA [5]. This insect control method can be utilized to protect plants efficiently against specific pests [2,8]. It is not required, however, that dsRNA be processed to siRNA in plant material. dsRNA may be ingested by the insect pest and processed to siRNA for the first time within the insect cell.

Numerous methods for introducing foreign genes into plants are known and can be used to insert an NT polynucleotide into a plant host, including biological and physical plant transformation protocols. See, e.g., Mild et al., "Procedure for Introducing Foreign DNA into Plants," in Methods in Plant Molecular Biology and Biotechnology, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as Agrobacterium (Horsch et al., Science 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in Methods in Plant Molecular Biology and Biotechnology, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) Biotechniques 4:320-334; and U.S. Pat. No. 6,300,543), electroporation (Riggs, et al., (1986) Proc. Natl. Acad. Sci. USA 83:5602-5606, direct gene transfer (Paszkowski et al., (1984) EMBO J. 3:2717-2722), and ballistic particle acceleration (see, for example, Sanford, et al., U.S. Pat. No. 4,945,050; WO 91/10725; and McCabe, et al., (1988) Biotechnology 6:923-926). Also see, Tomes, et al., "Direct DNA Transfer into Intact Plant Cells Via Microprojectile Bombardment". pp. 197-213 in Plant Cell, Tissue and Organ Culture, Fundamental Methods. eds. O. L. Gamborg & G. C. Phillips. Springer-Verlag Berlin Heidelberg N.Y., 1995; U.S. Pat. No. 5,736,369 (meristem); Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); WO 91/10725 (maize); Klein, et al., (1988) Plant Physiol. 91:440-444 (maize); Fromm, et al., (1990) Biotechnology 8:833-839; and Gordon-Kamm, et al., (1990) Plant Cell 2:603-618 (maize); Hooydaas-Van Slogteren & Hooykaas (1984) Nature (London) 311:763-764; Bytebierm, et al., (1987) Proc. Natl. Acad. Sci. USA 84:5345-5349 (Liliaceae); De Wet, et al., (1985) In The Experimental Manipulation of Ovule Tissues, ed. G. P. Chapman, et al., pp. 197-209. Longman, N.Y. (pollen); Kaeppler, et al., (1990) Plant Cell Reports 9:415-418; and Kaeppler, et al., (1992) Theor. Appl. Genet. 84:560-566 (whisker-mediated transformation); U.S. Pat. No. 5,693,512 (sonication); D'Halluin, et al., (1992) Plant Cell 4:1495-1505 (electroporation); Li, et al., (1993) Plant Cell Reports 12:250-255; and Christou and Ford, (1995) Annals of Botany 75:407-413 (rice); Osjoda, et al., (1996) Nature Biotech. 14:745-750; Agrobacterium mediated maize transformation (U.S. Pat. No. 5,981,840); silicon carbide whisker methods (Frame, et al., (1994) Plant J. 6:941-948); laser methods (Guo, et al., (1995) Physiologia Plantarum 93:19-24); sonication methods (Bao, et al., (1997) Ultrasound in Medicine & Biology 23:953-959; Finer and Finer, (2000) Lett Appl Microbiol. 30:406-10; Amoah, et al., (2001) J Exp Bot 52:1135-42); polyethylene glycol methods (Krens, et al., (1982) Nature 296:72-77); protoplasts of monocot and dicot cells can be transformed using electroporation (Fromm, et al., (1985) Proc. Natl. Acad. Sci. USA 82:5824-5828) and microinjection (Crossway, et al., (1986) Mol. Gen. Genet. 202:179-185); all of which are herein incorporated by reference.

The most widely utilized method for introducing an expression vector into plants is based on the natural transformation system of Agrobacterium. A. tumefaciens and A. rhizogenes are plant pathogenic soil bacteria, which genetically transform plant cells. The Ti and Ri plasmids of A. tumefaciens and A. rhizogenes, respectively, carry genes responsible for genetic transformation of plants. See, e.g., Kado, (1991) Crit. Rev. Plant Sci. 10:1. Descriptions of the Agrobacterium vector systems and methods for Agrobacterium-mediated gene transfer are provided in Gruber, et al., supra; Mild, et al., supra; and Moloney, et al., (1989) Plant Cell Reports 8:238.

Similarly, the gene can be inserted into the T-DNA region of a Ti or Ri plasmid derived from A. tumefaciens or A. rhizogenes, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) Science 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 06/913,914, filed Oct. 1, 1986, as referenced in U.S. Pat. No. 5,262,306, issued Nov. 16, 1993; and Simpson, et al., (1986) Plant Mol. Biol. 6:403-15, all incorporated by reference in their entirety.

Once constructed, these plasmids can be placed into A. rhizogenes or A. tumefaciens and these vectors used to transform cells of plant species, which are ordinarily susceptible to Fusarium or Alternaria infection. The selection of either A. tumefaciens or A. rhizogenes will depend on the plant being transformed thereby. In general A. tumefaciens is the preferred organism for transformation. Most dicotyledonous plants, some gymnosperms, and a few monocotyledonous plants (e.g., certain members of the Liliales and Arales) are susceptible to infection with A. tumefaciens. A. rhizogenes also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using Agrobacterium. European Application No. 672 752 A1 discloses a method for transforming monocots with Agrobacterium using the scutellum of immature embryos. Ishida, et al., discuss a method for transforming maize by exposing immature embryos to A. tumefaciens (Nature Biotechnology 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) Theor. Appl. Genet. 69:235-40; U.S. Pat. No. 4,658,082; Simpson, et al., supra; and U.S. patent application Ser. Nos. 06/913,913 and 06/913,914, both filed Oct. 1, 1986, as referenced in U.S. Pat. No. 5,262,306, issued Nov. 16, 1993, the entire disclosures therein incorporated herein by reference.

Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) Part. Sci. Technol. 5:27; Sanford, (1988) Trends Biotech 6:299; Sanford, (1990) Physiol. Plant 79:206; and Klein, et al., (1992) Biotechnology 10:268).

Another method for physical delivery of DNA to plants is sonication of target cells as described in Zang, et al., (1991) BioTechnology 9:996. Alternatively, liposome or spheroplast fusions have been used to introduce expression vectors into plants. See, e.g., Deshayes, et al., (1985) EMBO J. 4:2731; and Christou, et al., (1987) Proc. Natl. Acad. Sci. USA 84:3962. Direct uptake of DNA into protoplasts using $CaCl_2$ precipitation, polyvinyl alcohol, or poly-L-ornithine has also been reported. See, e.g., Hain, et al., (1985) Mol. Gen. Genet. 199:161; and Draper, et al., (1982) Plant Cell Physiol. 23:451.

Electroporation of protoplasts and whole cells and tissues has also been described. See, e.g., Donn, et al., (1990) Abstracts of the VIIth Int'l. Congress on Plant Cell and Tissue Culture IAPTC, A2-38, p. 53; D'Halluin, et al., (1992) Plant Cell 4:1495-505; and Spencer, et al., (1994) Plant Mol. Biol. 24:51-61.

Following stable transformation, plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant.

Transformed plant may be regenerated by micropropagation which provides a rapid, consistent reproduction of the transformed plants. Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

In certain aspects the invention provides methods of producing a plant resistant to a plant pathogenic pest by transforming a plant cell with a recombinant DNA construct or combination of constructs that express a dsRNA; regenerating a plant from the transformed plant cell; and growing the transformed plant cell under conditions suitable for the expression said recombinant DNA construct.

The methods of the invention are applicable to Bronze bug species, e.g., *Thaumastocoris peregrinus* that are susceptible to gene silencing by RNA interference and that are capable of internalizing dsRNA from their immediate environment. The invention is applicable to the insect at any stage in its development. Because insects have a non-living exoskeleton, they cannot grow at a uniform rate and rather grow in stages by periodically shedding their exoskeleton. This process is referred to as molting or ecdysis. The stages between molts are referred to as "instars" and these stages may be targeted according to the invention. Also, insect eggs or live young may also be targeted according to the present invention. All stages in the developmental cycle, which includes metamorphosis in the pterygotes, may be targeted according to the present invention. Thus, individual stages such as larvae, pupae, nymph etc. stages of development may all be targeted.

Bronze bug are pests for *eucalyptus*. The nucleic acids, dsRNAs and methods described herein are thus useful for treating or inhibiting Bronze bug infection and infestation of *eucalyptus*.

EXAMPLES

Example 1

Bronze Bug Transcriptome Sequencing

Bronze bug specimens were collected from infected leaves from *eucalyptus* from Sao Paulo State, Brazil. Total RNA was obtained from a mixture of nymphs and adults at various developmental stages. Batches of 100 specimens were placed in individual microtubes on ice. The tubes were then sealed and immediately frozen in liquid nitrogen and kept at −80° C. until further treatment. Total RNA was isolated using MasterPure RNA purification kit and protocol (MRC85102, Epicentere Biotechnologies). Total RNA volume was 50 μl. Total RNA was then treated with DNAse to remove residual DNA, followed by isolation of poly A mRNA (MicroPoly(A) Purist, Small scale mRNA Purification kit, AM1919 Ambion). mRNA final volume was 20 µl. The purified mRNA was kept at −80° C. until 454 Sequencing was performed. 454 Sequencing was carried out according to standard protocols to provide transcriptomes of the target pest. Sequences were assembled and results annotated on the basis of sequence alignment with known published hemiptera Pea Aphid *Acyrthosiphon pisum* (Ap) transcriptomes using the Roche software package and annotated using the Blast2Go program.

Example 2

Identification of Bronze Bug Target Genes and Sequences

Unique, vital Bronze bug genes essential either for cellular processes or proper developmental processes of a specific tissue or entire organism were chosen as targets for gene silencing. Based on published RNAi libraries in *Drosophila melanogaster* (Dm) [15, 16] a list was generated of 591 genes that were shown to be lethal in RNAi transgenic Dm. This list was further narrowed to genes that are involved in translation, transcription and development. The resulting subset of 141 genes are involved in one or more of the following: protein synthesis and/or metabolism, RNA synthesis and metabolism and cellular processes.

BLAST (NCBI) comparisons using 141 genes identified as being lethal when expressed as RNAi in *Drosophila* were used to identify 128 orthologous sequences Pea Aphid *Acyrthosiphon pisum* (Ap). Comparisons using the identified Ap sequences were further used to screen the Bronze bug 454 transcriptome library for potential target genes. Potential Bronze bug target genes were limited to Bronze bug 454 transcriptome sequences that included at least 310 bp in a continuous open reading frame or were at least 50% of the full predicted gene length. The screen of the Bronze bug 454 transcriptome identified 28 potential Bronze bug target sequences.

The 28 potential Bronze bug targets were further screen to identify sequences that share limited homology to honey bee, *Apis mellifera* (Ap) sequences. Comparisons were made using a publicly available NCBI Bl2Seq analysis program to identify 100 bp sequences from each Bronze bug target that shared limited (i.e., less than 80%) identity to corresponding Am genes (or, when not possible to identify a 100 bp sequence with less than 80% identity to identify, a shorter fragment of such sequences). The regions identified all exhibited 41-74% identity to the respective honey bee sequences.

The respective Bronze bug target genes and the sequences with limited homology to Ap sequences that were identified are set out in SEQ ID NO: 1-59 and 74-87. Table 1 sets out the SEQ ID NOs for the respective Bronze bug target genes and sequences with limited homology identified therein.

TABLE 1

Bronze Bug Target Sequences and Fragments With Limited Identity to Honey Bee (*Apis mellifera*) Sequences

| Bronze Bug Gene No. | Dm gene symbol/function (*A. mellifera* accession no.) | Bronze Bug Target Gene | Bronze Bug Sequence <80% identical to Am Sequence (% identity) |
| --- | --- | --- | --- |
| 2 | Aats-trp/Tryptophanyl-tRNA synthetase (XM_001123290) | SEQ ID NO: 1 | SEQ ID NO: 2 (58) |
| 3 | blw/hydrogen-exporting ATPase activity, (XM_392639) | SEQ ID NO: 3 + SEQ ID NO: 84 | SEQ ID NO: 4 (74) |
| 4 | Bur/ubiquitin-specific protease activator activity (XM_393336) | SEQ ID NO: 5 | SEQ ID NO: 6 (57) |
| 7 | Pros28.1A/Proteasome 28kD subunit 1A; ubiquitin-dependent protein catabolic process (XM_393583) | SEQ ID NO: 7 | SEQ ID NO: 8 (55) |
| 8 | Prosα3T/Proteasome α3T subunit; endopeptidase activity. ubiquitin-dependent protein catabolic process (XM_397196) | SEQ ID NO: 9 | SEQ ID NO: 10 (52) |
| 9 | CG2931/nuclear mRNA splicing, via spliceosome (XM_392161) | SEQ ID NO: 11 | SEQ ID NO: 12 (58) |
| 10 | CG31524/procollagen-proline 4-dioxygenase activity. oxidation-reduction process (XM_392392) | SEQ ID NO: 13 | SEQ ID NO: 14 (52) |
| 12 | CG3590/AMP AMP-lyase; purine nucleotide metabolic process (XM_393961) | SEQ ID NO: 15 | SEQ ID NO: 16 (59) |
| 13 | CG5451/nuclear mRNA splicing, via spliceosome (XM_393446) | SEQ ID NO: 17 | SEQ ID NO: 18 (66) |
| 20 | dlg 1/protein binding.anatomical structure development (XM_003251584) | SEQ ID NO: 19 | SEQ ID NO: 20 (64) |
| 24 | e(r)/regulation of transcription from RNA polymerase II promoter (XM_00111990) | SEQ ID NO: 21 | SEQ ID NO: 22 (68) |
| 26 | ebi/regulation of epidermal growth factor receptor signaling pathway; regulation of cell cycle (XM_003251282) | SEQ ID NO: 23 + SEQ ID NO: 85 | SEQ ID NO: 24 (70) |
| 27 | EcR/repressing transcription factor binding. anatomical structure development; biological regulation (NM_001159355) | SEQ ID NO: 25 | SEQ ID NO: 26 (57) |
| 28 | Efl alpha48D/translation elongation factor activity. determination of adult lifespan (NM_001014993) | SEQ ID NO: 27 | SEQ ID NO: 28 (65) |
| 29 | Efl gamma/translation elongation factor autophagic cell death; salivary gland cell autophagic cell deat (XM_623679) | SEQ ID NO: 29 | SEQ ID NO: 30 (62) |
| 30 | eIF-2alpha/translational initiation (XM_001122232) | SEQ ID NO: 31 | SEQ ID NO: 32 (41) |
| 31 | eIF3-S8/translational initiation (XM_623577) | SEQ ID NO: 33 | SEQ ID NO: 34 (60) |
| 32 | eIF5/translational initiation (XM_392511) | SEQ ID NO: 35 | SEQ ID NO: 36 (55) |
| 34 | hay/ATP-dependent DNA helicase activity (XM_624122) | SEQ ID NO: 37 or SEQ ID NO: 87 | SEQ ID NO: 38 (67) |

TABLE 1-continued

Bronze Bug Target Sequences and Fragments With Limited Identity to Honey Bee (Apis mellifera) Sequences

| Bronze Bug Gene No. | Dm gene symbol/function (A. mellifera accession no.) | Bronze Bug Target Gene | Bronze Bug Sequence <80% identical to Am Sequence (% identity) |
|---|---|---|---|
| 35 | Hel25E/RNA helicase activity (XM_624891) | SEQ ID NO: 39 + SEQ ID NO: 86 | SEQ ID NO: 40 (68) |
| 37 | Hr38/ligand-dependent nuclear receptor activity (NM_001159355) | SEQ ID NO: 41 | SEQ ID NO: 42 (65) |
| 40 | mask/structural constituent of cytoskeleton (XM_393472) | SEQ ID NO: 43 | SEQ ID NO: 44 (67) |
| 41 | mor/transcription coactivator activity (XM_393008) | SEQ ID NO: 45 | SEQ ID NO: 46 (50) |
| 47 | RpS2/structural constituent of ribosome (XM_392843) | SEQ ID NO: 47 | SEQ ID NO: 48 (61) |
| 48 | RpS5a/(XM_624081) structural constituent of ribosome | SEQ ID NO: 49 | SEQ ID NO: 50 (51) |
| 53 | Trip1/translation initiation factor activity (XM_392780) | SEQ ID NO: 51 | SEQ ID NO: 52 (63) |
| 54 | tws/protein serine/threonine phosphatase activity (XM_394082) | SEQ ID NO: 53 | SEQ ID NO: 54 (65) |
| 55 | Ubc-E2H/ubiquitin-protein ligase activity (XM_624081) | SEQ ID NO: 55 | SEQ ID NO: 56 (59) |
| 56 | Uev1A/ubiquitin-conjugating enzyme-like (XM_393411) | SEQ ID NO: 57 | SEQ ID NO: 58 (68) |
| 57 | Vps23/NADH-ubiquinone oxidoreductase, 20 Kd subunit (XM_392437.4) | SEQ ID NO: 74 | SEQ ID NO: 75 (61) |
| 58 | Vps28/Vacuolar protein sorting 28 (XM_392314.4) | SEQ ID NO: 76 | SEQ ID NO: 77 (59) |
| 59 | Vps22/lsn/Regulation of Notch signaling pathway (XM_003251158.1) | SEQ ID NO: 78 | SEQ ID NO: 79 (50) |
| 60 | Vps2/Protein transport (XM_625161.3) | SEQ ID NO: 80 | SEQ ID NO: 81 (70) |
| 61 | Snf7/shrub/ESCRT-III pathway (XM_395324.4) | SEQ ID NO: 82 | SEQ ID NO: 83 (60) |

The identified Bronze bug genes were divided into the following categories:

Proteins Synthesis and Metabolism:
SEQ ID NO: 1, 5, 7, 9, 21, 25, 27, 29, 31, 33, 35, 47, 49 and 51, respectively.

Cellular Processes:
SEQ ID NO: 3+84, 13, 15, 19, 23+85, 41, 43, 53, 55 and 57, respectively.

Nucleic Acid Synthesis and Metabolism:
SEQ ID NO: 11, 17, 37, 39+86 and 45, respectively.

Example 3

Preparation of dsRNA Silencing Constructs

Figure 1B:
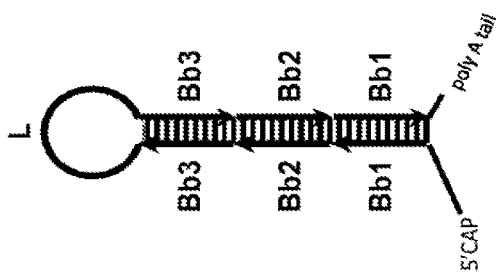
Figure 1C:
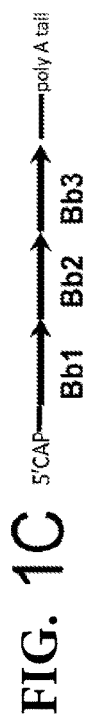

A schematic of the structure of dsRNA triple silencing constructs comprising segments from three Bronze bug genes is shown in FIG. 1. Silencing constructs contain two transgenes. A first transgene comprises fragments from each of three Bronze bug genes which are fused and synthesized in inverted repeats, separated by a loop sequence. See FIG. 1A. Transcription of this transgene (initiated at promoter P1 and terminated at T1) produces a hairpin RNA, containing a dsRNA section, formed by annealing of the inverted-repeat sequences of the three Bronze bug genes, and a loop region. See FIG. 1B. A second transgene contains three fused Bronze bug genes, oriented to be transcribed to yield a sense strand with the three gene fragments. See FIGS. 1A and 1C.

The following sequences are used to construct three silencing constructs.

Silencing Construct #1

Figure 2A:
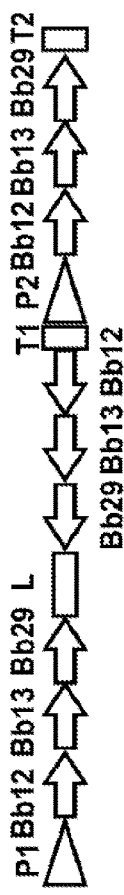
FIG. 2 schematically depicts certain, non-limiting nucleic acids according to the invention. (A) Schematic of silencing construct #1, constructed from sequences from three Bronze bug genes in accordance with the general scheme depicted in FIG. 1. (B) Schematic of hpRNA molecule produced by transcription of transgene P1 to T1. (C) Schematic of mRNA produced by transcription of transgene P2 to T2. Definitions: P1—CaMV 35S Promoter (SEQ ID NO: 60); P2—sgFIMV Promoter (SEQ ID NO: 61); T1—AtActin7 Terminator (SEQ ID NO: 62); T2—Nos Terminator (SEQ ID NO: 63); Bb12—SEQ ID NO: 16; Bb13—SEQ ID NO: 18; Bb29—SEQ ID NO: 30; L—loop sequence site (SEQ ID NO: 64).
Figure 2B:
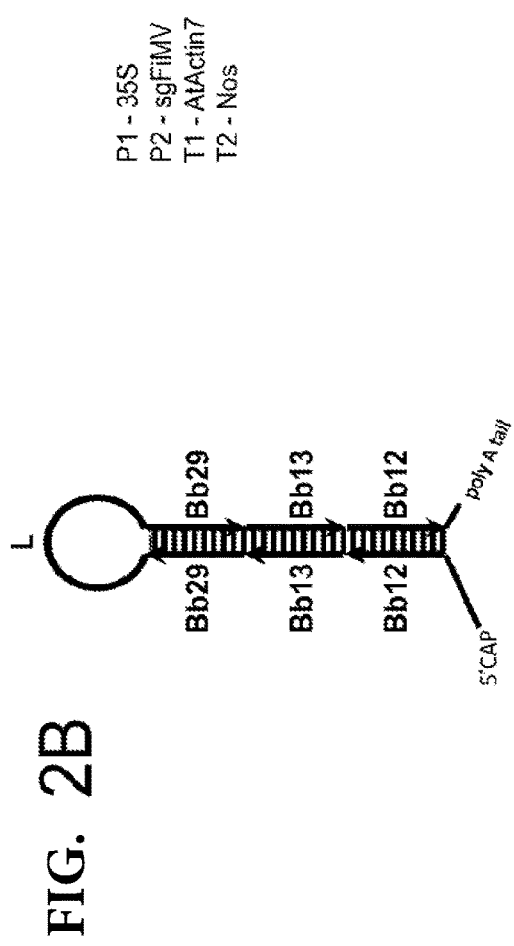
Figure 2C:

Silencing Construct #1 is shown schematically in FIG. 2. Respective 100 bp fragments of each of the Bronze bug CG3590 gene (SEQ ID NO: 15), CG5451 gene (SEQ ID NO: 17) and Ef1 gamma gene (SEQ ID NO: 29) were fused and synthesized in inverted repeats separated by 106 bp of a loop sequence (Loop 1; SEQ ID NO: 64). Transcription initiation was driven by the 35S CaMV promoter (SEQ ID NO: 60). Transcription termination was provided by the AtActin7 Terminator (SEQ ID NO: 62). The select 100 bp of Bronze bug SEQ ID NO: 15, 17 and 29 (respectively, SEQ ID NO: 16, SEQ ID NO: 18 and SEQ ID NO: 30) were synthesized in sense orientation between sgFIMV Promoter (SEQ ID NO: 61) to NOS Terminator (SEQ ID NO: 63).

Transcription of construct 1 would yield two mRNAs: (1) A hairpin RNA (hpRNA) with a stem formed by the reverse complementary sequences of the three Bronze bug 100 bp sequences, to silence the corresponding Bronze bug genes (see FIG. 2B); and (2) sense mRNA of the three, fused Bronze bug genes (see FIG. 2C).

The hpRNA formed upon transcription of the hpRNA-forming transgene of Construct #1 has the following sequence (SEQ ID NO: 65):

```
CTCTGCTCGGATGCTCTCCTCATCACTTTGATGAACATTTTGGAAGGGCT
CGTAGTCTACCCGAAAGTCATTGAAAAGCACATCGGAGAAGAACTTCCTT
CCGATTCTCAAGGGACAACAGTCAAATCCTCACCGCCTCGTTCGACACGA
CAATCAAAATTCACGGGTTGAAGTCAGGTAAATCGTTGAAGGAATTCCGC
GCAAAAGGTCTTCATGAGCTGCAACCTCATCACCGGCATGTACCAGAGAC
TGGACAAAATGAGGAAAAACGCTTTCGCCTCCGTCATTCTGTTCGGCAAA
GGCTCGAACGAGCCGACTAATTGTCTTTAAACGCGCGATATAAGCGCACA
ATGCTCGAGAAACGATAAACTCTATCGCTCTGTCGCGTGCGTGGCATCTT
CGCGCGTTTGCCGAACAGAATGACGGAGGCGAAAGCGTTTTCCTCATTT
TGTCCAGTCTCTGGTACATGCCGGTGATGAGGTTGCAGCTCATGAAGACC
TTTTGCGCGGAATTCCTTCAACGATTTACCTGACTTCAACCCGTGAATTT
TGATTGTCGTGTCGAACGAGGCGGTGAGGATTTGACTGTTGTCCCTTGAG
AATCGGAAGGAAGTTCTTCTCCGATGTGCTTTTCAATGACTTTCGGGTAG
ACTACGAGCCCTTCCAAAATGTTCATCAAAGTGATGAGGAGAGCATCCGA
GCAGAG
```

The respective hpRNA sequences correspond to the following elements:

Nucleotides 1-100 and 607-706: Respective sense and reverse complement sequences of SEQ ID NO: 16, corresponding to nucleotides 244-343 of SEQ ID NO: 15

Nucleotides 101-200 and 507-606: Respective sense and reverse complement sequences of SEQ ID NO: 18, corresponding to nucleotides 438-537 of SEQ ID NO: 17

Nucleotides 201-300 and 407-506: Respective sense and reverse complement sequences of SEQ ID NO: 30, corresponding to nucleotides 951-1050 of SEQ ID NO: 29

Nucleotides 301-406: 106 bp Loop fragment (SEQ ID NO: 64) based on Partial *Leptocibe invasa* Chitin Synthase intron The sense mRNA transcribed from construct 1 has the following sequence (SEQ ID NO: 66):

CTCTGCTCGGATGCTCTCCTCATCACTTTGATGAACATTTTGGAAGGGCT

CGTAGTCTACCCGAAAGTCATTGAAAAGCACATCGGAGAAGAACTTCCTT

CCGATTCTCAAGGGACAACAGTCAAATCCTCACCGCCTCGTTCGACACGA

CAATCAAAATTCACGGGTTGAAGTCAGGTAAATCGTTGAAGGAATTCCGC

GCAAAAGGTCTTCATGAGCTGCAACCTCATCACCGGCATGTACCAGAGAC

TGGACAAAATGAGGAAAAACGCTTTCGCCTCCGTCATTCTGTTCGGCAAA

Silencing Construct 2

Figure 3A:
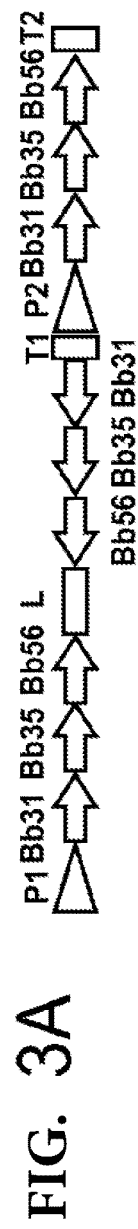
FIG. 3 schematically depicts certain, non-limiting nucleic acids according to the invention. (A) Schematic of silencing construct #2, constructed from sequences from three Bronze bug genes in accordance with the general scheme depicted in FIG. 1. (B) Schematic of hpRNA molecule produced by transcription of transgene P1 to T1. (C) Schematic of mRNA produced by transcription of transgene P2 to T2. Definitions: P1—CaMV 35S Promoter (SEQ ID NO: 60); P2—sgFIMV Promoter (SEQ ID NO: 61); T1—AtActin7 Terminator (SEQ ID NO: 62); T2—Nos Terminator (SEQ ID NO: 63); Bb31—SEQ ID NO: 34; Bb35—SEQ ID NO: 40; Bb56—SEQ ID NO: 59; L—loop sequence site (SEQ ID NO: 64).
Figure 3B:
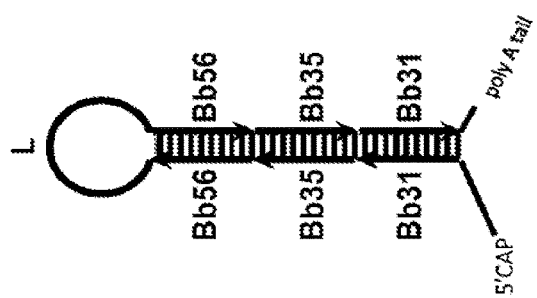
Figure 3C:

Silencing Construct #2 is shown schematically in FIG. 3. Respective 100 bp fragments of each of the Bronze bug eIF3-58 gene (SEQ ID NO: 33), Hel25E gene (SEQ ID NO: 39+86) and, Uev1A gene (SEQ ID NO: 57) were fused and synthesized in inverted repeats separated by 106 bp of a loop sequence (Loop 1; SEQ ID NO: 64). Transcription initiation was driven by the 35S CaMV promoter (SEQ ID NO: 60). Transcription termination was provided by the AtActin7 Terminator (SEQ ID NO: 62). The select 100 bp of Bronze bug SEQ ID NO: 33, 39+86 and 57 (respectively, SEQ ID NO: 34, SEQ ID NO: 40 and SEQ ID NO: 59 (corresponding to nucleotides 181-280 with a T253C substitution) were synthesized in sense orientation between sgFIMV Promoter (SEQ ID NO: 61) to NOS Terminator (SEQ ID NO: 63).

Transcription of construct 2 would yield two mRNAs: (1) A hairpin RNA (hpRNA) with a stem formed by the reverse complementary sequences of the three Bronze bug 100 bp sequences, to silence the corresponding Bronze bug genes (see FIG. 3B); and (2) sense mRNA of the three, fused Bronze bug genes (see FIG. 3C). The hpRNA formed upon transcription of the hpRNA-forming transgene of Construct #2 has the following sequence (SEQ ID NO: 67):

CGACCCGACTGTCATTCAACAGAGAAAGGGCGAATTGGAACCAGGCACC

CAAACTAGCATCCAAGTGATGGACAAATTGTGCAAGTACATTTACGACAA

GTGACATATTGGAGTTCAACCAGGTGGTCATTTTCGTCAAGTCTGTTCAA

CGGTGTATGGCTCTTGCTCAGCTCTTATGCGACCAAAACTTCCCGGCTGT

CAATCGCATGTACAGTTTACGAATAGAGTGTGGTCAGAAGTACCCGGAAG

ACGCTCCCTCGGCCCGATTTATACCTAGAATTAATATGACCTGCGTTAAT

AGGCTCGAACGAGCCGACTAATTGTCTTTAAACGCGCGATATAAGCGCAC

AATGCTCGAGAAACGATAAACTCTATCGCTCTGTCGCGTGCGTGGCATCT

TCGCGCGTATTAACGCAGGTCATATTAATTCTAGGTATAAATCGGGCCGA

GGGAGCGTCTTCCGGGTACTTCTGACCACACTCTATTCGTAAACTGTACA

TGCGATTGACAGCCGGGAAGTTTTGGTCGCATAAGAGCTGAGCAAGAGCC

ATACACCGTTGAACAGACTTGACGAAAATGACCACCTGGTTGAACTCCAA

TATGTCACTTGTCGTAAATGTACTTGCACAATTTGTCCATCACTTGGATG

CTAGTTTGGGTGCCTGGTTCCAATTCGCCCTTTCTCTGTTGAATGACAGT

CGGGTCG

The respective hpRNA sequences correspond to the following elements:

Nucleotides 1-100 and 607-706: Respective sense and reverse complement sequences of SEQ ID NO: 34, corresponding to nucleotides 21-120 of SEQ ID NO: 33

Nucleotides 101-200 and 507-606: Respective sense and reverse complement sequences of SEQ ID NO: 40, corresponding to nucleotides 15-114 of SEQ ID NO: 86

Nucleotides 201-300 and 407-506: Respective sense and reverse complement sequences of SEQ ID NO: 59, corresponding to nucleotides 181-280 of SEQ ID NO: 57, with a T→C mutation at position 253 of SEQ ID NO: 57, to create an Xba I site.

Nucleotides 301-406: 106 bp Loop fragment (SEQ ID NO: 64) based on Partial *Leptocibe invasa* Chitin Synthase intron The sense mRNA transcribed from construct 2 has the following sequence (SEQ ID NO: 68):

CGACCCGACTGTCATTCAACAGAGAAAGGGCGAATTGGAACCAGGCACC

CAAACTAGCATCCAAGTGATGGACAAATTGTGCAAGTACATTTACGACAA

GTGACATATTGGAGTTCAACCAGGTGGTCATTTTCGTCAAGTCTGTTCAA

CGGTGTATGGCTCTTGCTCAGCTCTTATGCGACCAAAACTTCCCGGCTGT

CAATCGCATGTACAGTTTACGAATAGAGTGTGGTCAGAAGTACCCGGAAG

ACGCTCCCTCGGCCCGATTTATACCTAGAATTAATATGACCTGCGTTAAT A

Silencing Construct 3

Silencing Construct #3 is shown schematically in FIG. 4. Respective 100 bp fragments of each of the Bronze bug Mor gene (SEQ ID NO: 45), Trip gene (SEQ ID NO: 51) and, tws gene (SEQ ID NO: 53) were fused and synthesized in inverted repeats separated by 106 bp of a loop sequence (Loop 1; SEQ ID NO: 64). Transcription initiation was driven by the 35S CaMV promoter (SEQ ID NO: 60). Transcription termination was provided by the AtActin7 Terminator (SEQ ID NO: 62). The select 100 bp of Bronze bug SEQ ID NO: 45, 51 and 53 (respectively, SEQ ID NO: 46, SEQ ID NO: 52 and SEQ ID NO: 54) were synthesized in sense orientation between sgFIMV Promoter (SEQ ID NO: 62) to NOS Terminator (SEQ ID NO: 63).

Transcription of construct 3 would yield two mRNAs: (1) A hairpin RNA (hpRNA) with a stem formed by the reverse complementary sequences of the three Bronze bug 100 bp sequences, to silence the corresponding Bronze bug genes (see FIG. 4B); and (2) sense mRNA of the three, fused Bronze bug genes (see FIG. 4C).

The hpRNA formed upon transcription of the hpRNA-forming transgene of Construct #3 has the following sequence (SEQ ID NO: 69):

AAAAGCGACTGCAGCCAAAGTCAAAGACATAATCAAACGCCACCAGGGA

ACGGTGGTCGAAAACGAAGAACAGGCGACCCACATCCTTTACCCTATTGT

-continued
```
GGTTGACGGGCACAACGGGTCAATCAACGACATGCAGATGCACTGGGAC

GGCACCATGTTTGTGACAGCTTCGAGTGACCACACAGCAAAGCTATTCGA

CAGATTTCGGTCGACTGTTTGGATTTTACGAAGAAGATCCTTCACACCGC

TTGGCATCCAACCGAGAACATTATTGCAGTGGCCGCCACCAACAATTTAT

TTGGCTCGAACGAGCCGACTAATTGTCTTTAAACGCGCGATATAAGCGCA

CAATGCTCGAGAAACGATAAACTCTATCGCTCTGTCGCGTGCGTGGCATC

TTCGCGCGAAATAAATTGTTGGTGGCGGCCACTGCAATAATGTTCTCGGT

TGGATGCCAAGCGGTGTGAAGGATCTTCTTCGTAAAATCCAAACAGTCGA

CCGAAATCTGTCGAATAGCTTTGCTGTGTGGTCACTCGAAGCTGTCACAA

ACATGGTGCCGTCCCAGTGCATCTGCATGTCGTTGATTGACCCGTTGTGC

CCGTCAACCACAATAGGGTAAAGGATGTGGGTCGCCTGTTCTTCGTTTTC

GACCACCGTTCCCTGGTGGCGTTTGATTATGTCTTTGACTTTGGCTGCAG

TCGCTTTT
```

The respective hpRNA sequences correspond to the following elements:

Nucleotides 1-100 and 607-706: Respective sense and reverse complement sequences of SEQ ID NO: 46, corresponding to nucleotides 159-258 of SEQ ID NO: 45

Nucleotides 101-200 and 507-606: Respective sense and reverse complement sequences of SEQ ID NO: 52, corresponding to nucleotides 1-100 of SEQ ID NO: 51

Nucleotides 201-300 and 407-506: Respective sense and reverse complement sequences of SEQ ID NO: 54, corresponding to nucleotides 753-852 of SEQ ID NO: 53

Nucleotides 301-406: 106 bp Loop fragment (SEQ ID NO: 64) based on Partial *Leptocibe invasa* Chitin Synthase intron The sense mRNA transcribed from construct 3 has the following sequence (SEQ ID NO: 70):

```
AAAAGCGACTGCAGCCAAAGTCAAAGACATAATCAAACGCCACCAGGGA

ACGGTGGTCGAAAACGAAGAACAGGCGACCCACATCCTTTACCCTATTGT

GGTTGACGGGCACAACGGGTCAATCAACGACATGCAGATGCACTGGGAC

GGCACCATGTTTGTGACAGCTTCGAGTGACCACACAGCAAAGCTATTCGA

CAGATTTCGGTCGACTGTTTGGATTTTACGAAGAAGATCCTTCACACCGC

TTGGCATCCAACCGAGAACATTATTGCAGTGGCCGCCACCAACAATTTAT

TT
```

Example 4

Figure 5A:
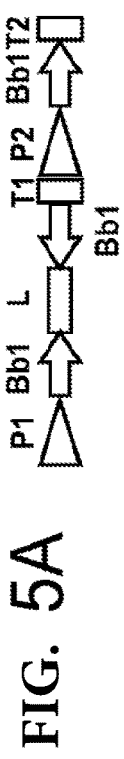
FIG. 5 schematically depicts certain, non-limiting nucleic acids according to the invention. (A) Schematic of silencing construct constructed using sequences from a single Bronze bug gene. Transgene P1 to T1 encodes a hairpin RNA (hpRNA) for silencing Bronze bug, constructed from 100 bp of a Bronze bug gene, by synthesizing the sequence as an inverted repeat, and inserting a loop sequence between the respective sense and inverted repeat sequences. Transgene P2 to T2 encodes an mRNA with the 100 bp sequence from the Bronze bug gene. mRNA transcribed from transgene P2 to T2 is the template for cytoplasmic enhancement of the silencing signal. (B) Schematic of hpRNA molecule produced by transcription of transgene P1 to T1. (C) Schematic of mRNA produced by transcription of transgene P2 to T2.
Figure 5B:
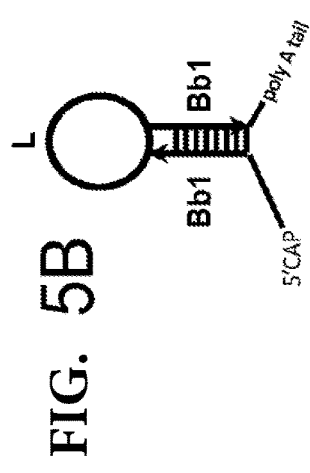
Figure 5C:

Schematic representations of silencing constructs comprising segments from one and two Bronze bug genes are shown in FIG. 5 and FIG. 6, respectively. Silencing constructs contain two transgenes. A first transgene comprises fragments from each of one (see FIG. 5) or two (FIG. 6) Bronze bug genes which are fused (in the case of constructs containing two Bronze bug genes) and synthesized in inverted repeats, separated by a loop sequence. See FIGS. 5A and 6A. Transcription of this transgene (initiated at promoter P1 and terminated at T1) produces a hairpin RNA, containing a dsRNA section, formed by annealing of the inverted-repeat sequences of the respective Bronze bug genes, and a loop region. See FIGS. 5B and 6B. A second transgene contains the Bronze bug genes, oriented to be transcribed to yield a sense strand with. See FIGS. 5C and 6C.

Silencing Construct #4

Single gene control sequences are generated using a combination of sequences comprising a first sequence of 100 bp sense-100 bp (approximate) loop-100 bp antisense, where "100 bp sense" and "100 bp antisense" refer to complementary sequences from a target gene, and a second 100-bp sense amplifying sequence. To construct silencing construct #4, 100 bp fragments of the Bronze bug tws gene (SEQ ID NO: 53) were fused and synthesized in inverted repeats separated by 106 bp of a loop sequence (Loop 1; SEQ ID NO: 64). Transcription initiation was driven by the 35S CaMV promoter (SEQ ID NO: 60). Transcription termination was provided by the AtActin7 Terminator (SEQ ID NO: 62). The select 100 bp of Bronze bug SEQ ID NO: 53 (SEQ ID NO: 54) was synthesized in sense orientation between sgFIMV Promoter (SEQ ID NO: 61) to NOS Terminator (SEQ ID NO: 63).

Transcription of construct 4 would yield two mRNAs: (1) A hairpin RNA (hpRNA) with a stem formed by the reverse complementary sequences of the Bronze bug 100 bp sequences, to silence the corresponding Bronze bug gene (see FIG. 5B); and (2) sense mRNA of the Bronze bug gene (see FIG. 5C).

The hpRNA formed upon transcription of the hpRNA-forming transgene of Construct #4 has the following sequence:

```
(SEQ ID NO: 71)
GATTTCGGTCGACTGTTTGGATTTTACGAAGAAGATCCTTCACACCGCTT

GGCATCCAACCGAGAACATTATTGCAGTGGCCGCCACCAACAATTTATTT

GGCTCGAACGAGCCGACTAATTGTCTTTAAACGCGCGATATAAGCGCACA

ATGCTCGAGAAACGATAAACTCTATCGCTCTGTCGCGTGCGTGGCATCTT

CGCGCGAAATAAATTGTTGGTGGCGGCCACTGCAATAATGTTCTCGGTTG

GATGCCAAGCGGTGTGAAGGATCTTCTTCGTAAAATCCAAACAGTCGACC

GAAATC
```

The respective hpRNA sequences correspond to the following elements:

Nucleotides 1-100 and 207-306: Respective sense and reverse complement sequences of SEQ ID NO: 54, corresponding to nucleotides 753-852 of SEQ ID NO: 53;

Nucleotides 101-206: 106 bp Loop fragment (SEQ ID NO: 61) based on Partial *Leptocibe invasa* Chitin Synthase intron.

The sense mRNA transcribed from construct 4 has the following sequence (SEQ ID NO: 54):

```
GATTTCGGTCGACTGTTTGGATTTTACGAAGAAGATCCTTCACACCGCTT

GGCATCCAACCGAGAACATTATTGCAGTGGCCGCCACCAACAATTTATTT
```

Silencing Construct #5

Two gene control sequences are generated using a combination of sequences comprising a 100 bp sense sequence 1-100 bp sense sequence 2-100 bp (approximate) loop-100 bp antisense sequence 1-,100 bp sense sequence 2 where "100 bp sense" and "100 bp antisense" refer to complementary sequences from a target gene, and a second 100-bp sense amplifying sequence.

To construct silencing construct #5, 100 bp fragments of the Bronze bug Trip1 gene (SEQ ID NO: 51) and tws gene (SEQ ID NO: 53) were fused and synthesized in inverted repeats separated by 106 bp of a loop sequence (Loop 1; SEQ ID NO: 64). Transcription initiation was driven by the 35S CaMV promoter (SEQ ID NO: 60). Transcription termination was provided by the AtActin7 Terminator (SEQ ID NO: 61). The select 100 bp of Bronze bug SEQ ID NO: 51 and 53 (SEQ ID NO: 52 and 54, respectively) were synthesized in sense orientation between sgFIMV Promoter (SEQ ID NO: 62) to NOS Terminator (SEQ ID NO: 63).

Transcription of construct 5 would yield two mRNAs: (1) A hairpin RNA (hpRNA) with a stem formed by the reverse complementary sequences of the Bronze bug 100 bp sequences, to silence the corresponding Bronze bug genes (see FIG. 6B); and (2) sense mRNA of the Bronze bug gene (see FIG. 6C).

The hpRNA formed upon transcription of the hpRNA-forming transgene of Construct #5 has the following sequence:

(SEQ ID NO: 72)
GTTGACGGGCACAACGGGTCAATCAACGACATGCAGATGCACTGGGACG

GCACCATGTTTGTGACAGCTTCGAGTGACCACACAGCAAAGCTATTCGAC

AGATTTCGGTCGACTGTTTGGATTTTACGAAGAAGATCCTTCACACCGCT

TGGCATCCAACCGAGAACATTATTGCAGTGGCCGCCACCAACAATTTATT

TGGCTCGAACGAGCCGACTAATTGTCTTTAAACGCGCGATATAAGCGCAC

AATGCTCGAGAAACGATAAACTCTATCGCTCTGTCGCGTGCGTGGCATCT

TCGCGCGAAATAAATTGTTGGTGGCGGCCACTGCAATAATGTTCTCGGTT

GGATGCCAAGCGGTGTGAAGGATCTTCTTCGTAAAATCCAAACAGTCGAC

CGAAATCTGTCGAATAGCTTTGCTGTGTGGTCACTCGAAGCTGTCACAAA

CATGGTGCCGTCCCAGTGCATCTGCATGTCGTTGATTGACCCGTTGTGCC

CGTCAAC

The respective hpRNA sequences correspond to the following elements:

Nucleotides 1-100 and 407-506: Respective sense and reverse complement sequences of SEQ ID NO: 52, corresponding to nucleotides 1-100 of SEQ ID NO: 51;

Nucleotides 101-200 and 307-406: Respective sense and reverse complement sequences of SEQ ID NO: 54, corresponding to nucleotides 753-852 of SEQ ID NO: 53;

Nucleotides 201-306: 106 bp Loop fragment (SEQ ID NO: 64) based on Partial *Leptocibe invasa* Chitin Synthase intron.

The sense mRNA transcribed from construct 5 has the following sequence:

(SEQ ID NO: 73)
GTTGACGGGCACAACGGGTCAATCAACGACATGCAGATGCACTGGGACG

GCACCATGTTTGTGACAGCTTCGAGTGACCACACAGCAAAGCTATTCGAC

AGATTTCGGTCGACTGTTTGGATTTTACGAAGAAGATCCTTCACACCGCT

TGGCATCCAACCGAGAACATTATTGCAGTGGCCGCCACCAACAATTTATT

T

Example 5

Expression of RNAi Constructs in *Eucalyptus*

RNA constructs are transformed into *eucalyptus* using a protocol essentially described in Prakash et al., *In Vitro Cell Dev Biol.-Plant,* 2009, 45:429-434. Briefly, shoots of *Eucalyptus* are propagated in vitro on Murashige and Skoog (MS) basal salt medium consisting of 3% (w/v) sucrose and 0.8% (w/v) agar. All in vitro plant materials are incubated at 25±2° C. under a 16-h photoperiod with cool white fluorescent lamps with an intensity of 30 $\mu Em^{-2}$ $s^{-1}$. *A. tumefaciens* strain LBA 4404 harboring a binary vector pBI121 containing nptII gene is used for transformation. Bacterial culture collected at late log phase are pelleted and resuspended in MS basal salt medium. Leaves from in vitro material are collected and used as explants for transformation experiments.

Explants are precultured on the MS regeneration medium supplemented with 0.5 mg/l BAP and 0.1 mg/l NAA for 2 d. Precultured leaf explants are gently shaken in the bacterial suspension for 10 min and blotted dry on a sterile filter paper. Explants are then cocultivated in medium under the preculture conditions for 2 d. Following cocultivation, explants are washed in MS liquid medium, blotted dry on a sterile filter paper, and transferred to MS regeneration medium containing 0.5 mg/l BAP and 0.1 mg/l NAA supplemented with 40 mg/l kanamycin and 300 mg/l cefotaxime. After 4-5 weeks of culture, regeneration is observed and explants are transferred to liquid elongation medium (MS medium supplemented with 0.5 mg/l BAP, 40 mg/l kanamycin, and 300 mg/l cefotaxime) on paper bridges. The elongated shoots (1.5-2 cm) are propagated on MS medium with 0.1 mg/l BAP. Leaf segments are regenerated and elongated shoots are analyzed by PCR and western blot. Positive shoots are multiplied to 10 copies on MS medium containing 0.04 mg/L BAP. A few leaves are excised from the shoots and analyzed by RT-PCR.

Expression of dsRNAs is measured using RT-PCR. Total RNA from 50 mg fresh transgenic plant tissue was purified using EPICENTRE MasterPure™ Plant RNA Purification Kit (Cat. #MPR09010) following by DNAse treatment with Ambion TURBO DNA-free™ Dnase (Cat. #AM1907). 1 µl of total RNA from each sample is analyzed by RT PCR. RT PCR is performed using Invitrogen SuperScript III One-Step RT-PCR System with Platinum Taq DNA Polymerase kit (Cat. #12574-018). As a control, the Platinum Taq DNA Polymerase kit (Cat. #12574-018 and #10966-018) is used to recognize traces of DNA contaminations. No fragment amplification is expected for this control.

To detect expression of RNA from constructs, RT-PCR is prepared using primer pairs that generate fragments indicative of the presence and expression of Bronze bug transgenes.

Example 7

Bioassay of Bronze Bug dsRNA Constructs

Sup Suckers Artificial Feeding
100 µl of feeding solution (standard diet described in Febvay et al., Canadian Journal of Zoology 66:2449-2453, 1988) is placed between two stretched paraffin membranes on a plastic cap. 10 Bronze bugs are placed on the paraffin membranes and covered with a Petri dish lid that is ventilated by a 1 cm hole covered with a mesh. Feeding solution containing siRNA, and/or dsRNA and/or hpRNA and/or microRNA homologous to one or more of the target genes described above in Table X is provided. RNA concentration can be between 10 ng to 500 ng per microliter. Bronze bugs are incubated for up to 40 days. Data on the number viable and dead bugs data is compiled daily. Candidate lethal sequences and their corresponding lethal target genes are ranked based on live to dead bug ratios data.

Example 8

Test of Protective Effect of Bronze Bug dsRNA Constructs

*Eucalyptus* plants are transformed with plasmids comprising construct 1, construct 2 or construct 3 (and transgenic lines are established. Controls lines are established by transforming plants with vector alone, without insertion of Bronze bug nucleic acids or without nucleic acids that could form siRNAs.

Transgenic, wt, and control *eucalyptus* plants are grown in insect proof cages in the greenhouse together with adult Bronze bugs. The insect proof cages keep the inoculums in while preventing outside pests from entering the cage. Following Bronze bug inoculation, the appearance of leaf damage is evaluated. Leaf damage can be seen as bronze-like spots or areas on the upper or lower surface of the leaves. These bronze areas are formed by as direct and/or indirect result of the sap-sucking activities of the Bronze Bugs. Plants are examined to determine number of Bronze bugs number of eggs and clusters of eggs on the plant tissues including leaves, reproductive organs, branches, stems, but predominantly on the leaves, and the number of dead or dysfunctional BB specimens found on or adjacent to the plants. The primary endpoints for a resistant plant can be either lack of symptoms, lack of viable pests on the plant surfaces and/or lack of eggs or egg clusters on the plants or retarded or altered growth development of nymphs. In some cases resistant plants may simply cause the contacting pests to become unviable or sterile without causing pest death. Five independent transformation events of transgenic *eucalyptus* plants transcribing dsRNA are tested. Ten lines of each transformation event are inoculated with adult Bronze bug in 3 independent repeats. Number of vital Bronze Bugs, their size, eggs, clusters of eggs, nymphs, dead bugs are recorded every day for 40 days after inoculation.

Exemplary prophetic result: Transgenic plants transcribing dsRNA targeting BB genes exhibit fewer symptoms, fewer vital Bronze bugs, less eggs and less egg clusters, less newly hatched nymphs, compared to controls. Transgenic plants lines are resistant to BB infection showing less leaf and other tissue damage, compared to control and wt plants that are infected with Bronze bugs.

Bioassay:
Whole Plant Assay:
Five 3 month old transgenic and wt *eucalyptus* plants of each line were grown in a green house at 24° C., 40-60% RH and 16 hr of light per day. The trees were tested for Bronze bug resistance for a period of 40 days, from tree age of 3 months. Each plant line was maintained in a separate insect proof cage and each plant was inoculated with 50 adult and/or nymphs bugs that were reared in culture.

Every day after inoculation the following parameters were tested:
1. Number of live bugs on each plant.
2. Number of live bugs not on plants.
3. Number of dead bugs.
4. Number of deformed, dysfunctional or non-reproductive pests.
4. Number of eggs laid.
5. Number of nymph hatched.
6. Number of defoliated leaves.
7. Number of discolored leaves.
8. Number of discolored patches per infected leaf
9. Number of dead branches.
10. Number of dead plants.

Single Leaf Assay:
Five 3 months old transgenic and wt *eucalyptus* of each line were grown in a green house at 24° C., 40-60% RH and 16 hr of light a day. The trees were tested, from age 3 months, for Bronze bug resistance for a period of 40 days. Each line was contained in a separate insect proof cage and 5 leaves of each plant were covered with clip-on insect cages described by Univ of Arizona Center for Insect Science Center for Education Outreach. Ten adult bugs were placed inside each leaf clip cage. Clip cages can be clipped over a leaf-feeding insect without disturbing the insect or the plant. These cages provide a simple way to isolate one or more sap-sucking pests or other small insects for investigation and observation.

Every day the following observations were made:
 1. Percent mortality ((total number of bugs−live bugs)/total number of bugs)×100 was calculated.
 2. Extent, number and percentage of discolored leaves was recorded.
 3. Number of eggs or egg clusters Results:
Full Plant Assay:
Transgenic *eucalyptus* will significantly differ from the wt in these parameters:
 1. Less vital bugs on the plants.
 2. More live bugs off plants.
 3. More dead bugs.
 4. Fewer eggs and/or egg clusters laid.
 5. Fewer nymphs hatched.
 6. Less defoliated leaves.
 7. Less discolored leaves.
 8. Less dead branches
 9. Less dead plants.

Transgenic trees can have part or all of the above list as a phenotype following Bronze bug infestation.

Single Leaf Assay, Predicted Results:
Higher mortality rate was observed in the cages set around transgenic leaves compared to wild type starting day 2 and onwards.

No discoloration symptoms compared to wild type were visible in the transgenic leaves for the whole infection period.

No eggs or egg clusters were found on leaves of transgenic plants compared to wild type.

A number of embodiments of the invention have been described. Nevertheless, it will be understood that various modifications may be made without departing from the spirit and scope of the invention. Accordingly, other embodiments are within the scope of the following claims.

All patents, patent publications and non-patent literature referenced in the specification are hereby incorporated herein by reference in their entireties.

REFERENCES

1. Baum J A, et al., Control of coleopteran insect pests through RNA interference, (2007), Nat Biotechnol. 25:1322-6.

2. Frizzi A, et al., Tapping RNA silencing pathways for plant biotechnology, (2010), Plant Biotechnol 8:655-77.
3. Gordon K H, et al., RNAi for insect-proof plants, (2007), Nat Biotechnol 25:1231-2.
4. Huvenne H, et al., Mechanisms of dsRNA uptake in insects and potential of RNAi for pest control: a review, (2010), J Insect Physiol 56:227-35.
5. Mao Y B, et al., Silencing a cotton bollworm P450 monooxygenase gene by plant-mediated RNAi impairs larval tolerance of gossypol, (2007), Nat Biotechnol 25:1307-13.
7. Nunes F M, et al., A non-invasive method for silencing gene transcription in honeybees maintained under natural conditions, (2009), Insect Biochem Mol Biol 39:157-60.
8. Price D R, et al., RNAi-mediated crop protection against insects, (2008), Trends Biotechnol 26:393-400.
10. Tinoco M L, et al., In vivo trans-specific gene silencing in fungal cells by in planta expression of a double-stranded RNA, (2010), BMC Biol 8:27.
11. Hannon, G. J., RNA interference, (2002), Nature 418: 244-251
12. Baulcombe, D., RNA silencing in plants, (2004), Nature 431:356-363.
13. Pei Y, et al., On the art of identifying effective and specific siRNAs, (2006), Nature Methods 3(9):670-676.
14. Cullen, B R., Enhancing and confirming the specificity of RNAi experiments, (2006), Nature Methods 3(9):677-681.
15. Chen et. al, New Genes in *Drosophila* Quickly become essential, Science (2010), 330:1682-5.
16. Dietzl et. al., A Genome Wide Transgenic RNAi Library for Conditional Gene Inactivation in *Drosophila*. Nature (2007), 448:151-7.

SEQUENCES

```
                                                    SEQ ID NO: 1
Gene #2
Aats-trp
tryptophanyl-tRNA synthetase-like
GATGTCGTCAACCCTTGGTCCGTTTCAAGTTCCTCGCAGGAAGGGATTGA

CTACGATAAACTCATAAAGAAGTTTGGCAGCTCCAAAATCGACCGAGAGC

TGCTCGACCGGTGGGAAAAAGCCACTGGAAAACCAGCCCACCATCTACTC

CGTCGAGGGATTTTCTTCAGTCATCGCGACGTCCATACAATATTGAATTT

GGTGAACAAGGGAAAAAGTTCTATTTGTACACCGGCCGAGGGCCGTCCT

CCGCTTCAATGCATGTCGGACATTTGGTCCCGTTCGTTTTTACAAAGTGG

ATTCAAGAAATGTTCAACGTTCCTCTCGTCATTCAATTGACCGACGACGA

AAAGTTTCTCTGGAAAGACCTATCTGTGGAAGAGGCGAACAAGATGGCCT

GGGAAAACGCTAAAGACATTATCGCCTGTGGCTTCGACGTCAATAAAACG

TTTATCTTCTCTGATTTGGACTACATGGGCAGTGCTCGGAATTCTACAA

GAATGTGGTCCGGATTCAAAAGTGCGTCACTTTCAATCAAGTTAAAGGCA

TTTTCGGATTCGGAGACAGTGACGTCATTGGGAAAATTAGTTTTCCGGCC

ATTCAAGCCGCACCCAGCCTTTCCACGTCGTTTCCATTCATTTTCGGAAA

GGAGAAAATTCCCTGTTTGATACCTTGTGCCATTGATCAGGATCCTTATT

TTCGAATGACGAGAGACGTTGCGCCGCGTCTGGGCTTCCCTAAACCAGCC

CTGCTCCACTCCACTTTTATTCCAGCTCTGCAAGGAGCTCAAACGAAAAT

GTCGGGCAGCGACGCCAACACCGCTATTTTCCTCACGGATACTCCG
```

```
                                                    SEQ ID NO: 2
Gene #2
Nucleotides 93-192 of SEQ ID NO: 1
Aats-trp
tryptophanyl-tRNA synthetase-like

CCGAGAGCTGCTCGACCGGTGGGAAAAAGCCACTGGAAAACCAGCCCAC

CATCTACTCCGTCGAGGGATTTTCTTCAGTCATCGCGACGTCCATACAAT

A
```

```
                                        SEQ ID NO: 3 + SEQ ID NO: 84
Gene #3
Blw
ATP synthase subunit alpha (partial with gap)
SEQ ID NO: 3:
GCCATCGTCGATGTTCCCGTCGGTGACGACATTCTTGGCCGAGTTGTCGA

CGCCCTTGGAAACCCTATCGATGGCAAGGGCCCTCTTTCTGGTAAATAGA

GGATGCGAGTTGGTGTCAAAGCCCCGGGTATCATCCCCAGGATCTCGGTC

CGCGAGCCTATGCAAACCGGAATCAAAGCCGTTGACTCGCTTGTACCCAT

CGGTCGAGGACAACGGGAGCTCATCATTGGAGAG [gap]

SEQ ID NO: 84:
GATGCGGAAGACGAAAAGAAGAAGTTGTACTGTATCTACGTTGCTATTGG

ACAGAAAAGATCCACTGTCGCGCAAATTGTGAAAAGATTGACCGACACCG

GGGCCATGAAATACACCATCATTGTCGCTGCGACTGCATCTGACGCCGCA

CCTCTCCAATACTTGGCTCCCTATTCCGGTTGCGCCATGGGAGAATTTTT

CAGGGACAGCGGAAAACACGCCCTTATCATTTTCGACGATTTGTCCAAAC

AGGCCGTCGCTTACCGTCAAATGTCTCTTCTGTTGAGACGTCCACCTGGT

CGTGAGGCCTACCCTGGAGACGTTTTCTACCTTCACTCTCGTCTATTGGA

ACGAGCTGCTAAAATGAACGAAACGCAAGGAGGTGGTTCGCTCACCGCTT

TGCCTGTTATCGAAACTCAGGCCGGTGACGTGTCTGCCTACATTCCGACC

AATGTTATTTCCATTACGGATGGACAAATTTTCCTTGAAACTGAGTTGTT

CTACAAAGGTATCCGACCCGCCATTAACGTCGGATTGTCTGTGTCCCGTG

TAGGTTCTGCCGCCCAAACCAAGGCCATGAAACAGGTGGCCGGTTCCATG

AAATTGGAGCTTGCTCAGTATCGTGAGGTCGCTGCTTTCGCGCAGTTCGG

TTCCGACTTGGACGCTGCCACCCAACAACTGCTGAACCGTGGTGTTCGTC

TTACGGAACTTCTCAAACAAGGACAATACGTTCCCATGGCCATTGAAGAA

CAGGTCGCTGTCATCTACTGCGGTGTCCGAGGTTTCTTGGACAAATTGGA

CCCGGCCAAGATCACCCAATTCGAGAAGGAGTTCCTTCAACACATCAAGA

CTTCTCACAAAGACCTGTTGGCCTCCATCGCCAAAGAGGGAAAGATCAGT

GACGAAAATGATGCCAAGATGAAGGGCATTGTTACTTCTTTCCTCAGTGG

CTTCTCCGGCTAG
```

```
                                                    SEQ ID NO: 4
Gene #3
Nucleotides 50-149 of SEQ ID NO: 84
Blw
ATP synthase subunit alpha
GACAGAAAAGATCCACTGTCGCGCAAATTGTGAAAAGATTGACCGACACC

GGGGCCATGAAATACACCATCATTGTCGCTGCGACTGCATCTGACGCCGC
```

SEQ ID NO: 5
Gene #4
Bur
GMP synthase [glutamine-hydrolyzing]-like
isoform 1 (partial)
GAAAGGGACTTCTCCGAAACTCAAGTCCTCGTTAAAATTATTGTTGAGTA

CGATCAAATGCTGCAGAAGAATCACGCGTTGTTGAATCGAGTGGAAAATG

CGACGAACGAAGACGAAAGGGTTCAATTGAGGAAGGTGTCGAGCAAGCAG

CACATGGCCGCAACAGTACTTCCGATCCGGAGTGTAGGAGTTCAGGGAGA

CTGTCGCAGCTACAGCTACGTCGTTGGGATATCAAGCGAGAAAGACCCGG

ATTGGGATGACCTCGTCATCCTCTCGCAGCTTATTCCCCGTGTGTGCCAC

AACGTCAACCGAGTCTGCTACATTGCTGGCGGCCTCGTCAAAGACCCTGT

TCAGGACATCACTCCGACTTTTCTCACTTCTCCAGTTCTGGCGACGATAC

GACAAGCAGACCATTTGGCGACTCAGGTCCTCTATAATAGCGATTACATG

TCTAAAATATCGCAAATGCCCGTGATCCTCCTTCCACTGCATTTTGACCG

GGACGCCGCTCTCCGAGTCCCATCGTGTCAACGGTCCGTTGTTCTCCGCC

CATTTATCACGCACGATTTCATGACGGGAATCCCAGCCATCCCGGGATCC

ACATACCCATTGACATCGTTCAAAAAAATGTTCTCTGAAATCTCCTTAAT

GCCGGGAATCTCTCGTGTCCTGTACGACCTGACAGCCAAACCACCCGGAA

CAACTGAATGGGAGTGA

SEQ ID NO: 6
Gene #4
Nucleotides 368-467 of SEQ ID NO: 5
Bur
GMP synthase [glutamine-hydrolyzing]-like
isoform 1 (partial)
CTTTTCTCACTTCTCCAGTTCTGGCGACGATACGACAAGCAGACCATTTG

GCGACTCAGGTCCTCTATAATAGCGATTACATGTCTAAAATATCGCAAAT

SEQ ID NO: 7
Gene #7
Pros28.1A
proteasome subunit alpha type-like (full)
ATGGGAACTGCGAGGTACGACCGGGCCATCACCGTTTTCTCGCCTGATGG

GCACCTCCTCCAAGTCGAATACGCCCAAGAGGCCGTCCGAAAAGGATCAA

CTGCCGTGGGAGTCCGAGGGGAAGACTGCGTCGTTCTCGGAGTTGAAAAG

AAATCAGTGGCGAAACTCCAAGAGGAAAGAACAGTGAGGAAAGTGTGTCT

TTTAGACGATCACATTCTCATCGCGTTTGCCGGTCTGACTGCGGATGCTC

GAATATTAATTAATCGGGCGCAAATAGAGTGTCAATCGCACAAGTTGACT

GTAGAGGACCCGGTGACGGTTGAGTACATCACACGTTACATAGCAGGGCT

TAAACAGAAATACACGCAGAGCAATGGCCGGCGACCGTTTGGCATTTCGT

GCCTTATTGGTGGTTTTGATTTGGACGGGTCACCTCATCTGTTCCAAACG

GAACCTTCTGGAATATTCTACGAGTGGAAAGCCAATGCCACAGGTCGCGG

TGCCAAGTCAGTTAAGGAGTTCCTTGAAAAGAATTACGAAACTTCCGACT

TGAAGACTGAAGACGGTGTCATCAAGTTGGCAGTTCGGGCTCTGCTAGAA

GTCGTGCAGTCCGGCCGAAGAATTTGGAAGTCGCTGTGATGCGCCGGAA

TCAGCCTTTGAGAATGCTGGATCTGGATTCGATCGATCAAATTGTGACTC

AAGTTGAACAAGAAAAAGAGGAGGAAGCTGAAAAGAAGAAGCAGAAGAAA

TAA

SEQ ID NO: 8
Gene #7
Nucleotides 498-497 of SEQ ID NO: 7
Pros28.1A
proteasome subunit alpha type-like
CGGTGCCAAGTCAGTTAAGGAGTTCCTTGAAAAGAATTACGAAACTTCCG

ACTTGAAGACTGAAGACGGTGTCATCAAGTTGGCAGTTCGGGCTCTGCTA

SEQ ID NO: 9
Gene #8
Prosa3T
proteasome subunit alpha type-like (full)
ATGGCCCGCCGTTATGACTCGAGAACGACAATATTTTCGCCGGAAGGTCG

ACTGTACCAAGTTGAGTATGCGATGGAGGCGATAAGTCATGCCGGTACGT

GTTTGGGCATCCTGGCCAACGACGGTATCATTCTCGTCGCTGAAAAAGAA

AACCCCAACAAGCTCTTGGATGAGTCCGTGTACTCGGAAAAAATTTTCAA

GCTTAACGAAAACATGATATGCAGTTTAGCCGGGATCACTTCCGATGCGA

ACGTCCTCACAAACGAGCTCCGTGTCATCTCCCAACGCTATTTGATCCAG

TACGGTGAAACGATCCCCTGTGAGCAGCTCGTCTCGTGGCTTTGTGACAT

TAAACAAGCGTACACTCAATACGGTGGTAAGAGGCCTTTCGGTGTTTCCG

TCCTGTACATGGGCTGGGACAAACACTACGGCTACCAACTCTATCAATCC

GATCCGAGCGGTAACTACTCCGGATGGAAAGCCACCTGTATCGGGCAAAA

CAGTGGAGCAGCCGTTTCCAGCCTTAAAACCGACTATAAAGAAGGTGAAA

TGACCGTTCAAGACGCTCTAGCTCTCGGAATCAAAGTCTTAAGCAAAACT

TTAGACACTGCCAAATTAACAACTGATCGCGTGGAAGTTGCAACGCTTCA

GCGCATCGATGGCAAATGCATCACTCGGATTTTGCCCGCTAGTGAAGTTC

AAGTACTCATTGACGCATTTGAAAAGTCTGAGGCTGAAGCCGCCGCTCAA

AGGAGAGAAAGAGCTCCGAATCCTTAA

SEQ ID NO: 10
Gene #8
Nucleotides 673-772 of SEQ ID NO: 9
Prosa3T
proteasome subunit alpha type-like
ACTCGGATTTTGCCCGCTAGTGAAGTTCAAGTACTCATTGACGCATTTGA

AAAGTCTGAGGCTGAAGCCGCCGCTCAAAGGAGAGAAAGAGCTCCGAATC

SEQ ID NO: 11
Gene #9
CG2931
RNA-binding protein 42-like (partial)
ACCGCTGGAGGTCAGACTTGGGAAGACAACACGCTCGCCGAATGGGAAGA

TGATGATTTCCGGCTTTTTTGTGGAGATTTAGGAAACGATGTCACCGACG

AAGTCTTAACCCGAGCGTTTTCCAAGTATCCGTCATTTCTCAAAGCTCGA

GTCGTTCGCGACAAAAGAACAAATAAAACTAAAGGATTTGGTTTCGTCAG

TTTCAAAGATCCAAACGATTTCATACGAGCAACTAAAGAAATGAATGGCC

GCTACGTCGGGTCACGTCCCATTAAATTAAGGAAAAGCTCATGGAAAAAC

AGAACTTTGGATGTCGTCAGAAAGAAGGATAAAGAAAAAGCAGCTCTCAT

TAGTATGCTCACAGGGAAATGA

SEQ ID NO: 12
Gene #9
Nuclotides 272-371 of SEQ ID NO: 11
CG2931
RNA-binding protein 42-like
TTAAATTAAGGAAAAGCTCATGGAAAAACAGAACTTTGGATGTCGTCAGA

AAGAAGGATAAAGAAAAAGCAGCTCTCATTAGTATGCTCACAGGGAAATG

SEQ ID NO: 13
Gene #10
CG31524
prolyl 4-hydroxylase subunit
alpha-2-like isoform 2 (partial)
GAAATGTATGAGTTGGCCTGTCGTGGGCTCCTGTCACCGCCACCGTCGCT

TTGCTCAACTGAAGTGCCGCTACGTTACCAAATCTCCTTTTACAATTTGG

CTCCATTGAAAGAAGAAGAAGCATATCTGAAACCGAAAATCATACTTTAC

CGGGAAGTGATGTATCACTCGGAAATTGAAATCATCAAACAAATGGCTCA

TCCCAGGTTGAAACGAGCGACAGTCCAAAATTACAAAACTGGAGAGTTGG

AAATCGCCTCATATCGAATATCAAAATCCGCGTGGTTCAATGACAACGAC

CACGAGGTGATGGCGCGGTTGACGAGGAGAGTCGAGGACATGACGGGCTT

AACAATGAAATCTGCCGAAGACCTCCAAGTCGTCAATTACGGCATTGGAG

GCCACTATGAGCCACATTACGATTTTGCCAGAAAAGGAGAAGAAACACAT

GCGTTCAAGTCTCTCGGAACTGGGAACAGAATCGCTACAGTATTGTTCTA

TATGAGCGACGTCGCTCAAGGAGGTGCCACCGTGTTCCCCCAGCTAAATC

TGTCTCTTTGGCCGGAAAAAGGAACTGCTGCGTTTTGGATGAATCTTCTC

GCCAATGGTGAAGGTGATTACGACACGAGGCATGCAGCATGTCCTGTACT

AGCAGGCACGAAATGGGTGTCTAACCGGTGGATCCACGAAAGAGAACAAG

AGTTCAGGAGACCCTGTTCGCTGGATCCCAACGAGTGAATTATTCCCACA

SEQ ID NO: 14
Gene #10
Nuclotides 241-340 of SEQ ID NO: 13
CG31524
prolyl 4-hydroxylase subunit
alpha-2-like isoform 2
GGAGAGTTGGAAATCGCCTCATATCGAATATCAAAATCCGCGTGGTTCAA

TGACAACGACCACGAGGTGATGGCGCGGTTGACGAGGAGAGTCGAGGACA

SEQ ID NO: 15
Gene #12
CG3590
adenylosuccinate lyase-like (partial)
CTCTGCACAGACCTCAGGCTCCTTGACAAATATGAAAGAGATTGAAGAGC

CTTTCGAAAAACTCAAATTGGGTCAAGCGCTATGGCGTACAAAAGGAATC

CAATGAGAAGTGAAAGGTGTTGCGCTTTGGCCCGTCACTTGGTCTCTTTG

CACTCGAATGCGGCCAACACTGCTGCCGTCCAATGGCTCGAAAGAACCCT

AGATGACAGCGCCAATCGACGCATCACCCTAGCCGAAGCGTTTCTCTGCT

CGGATGCTCTCCTCATCACTTTGATGAACATTTTGGAAGGGCTCGTAGTC

TACCCGAAAGTCATTGAAAAGCACATCGGAGAAGAACTTCCTTTTATGGC

AACTGAGAACATCATTATGGCCATGGTCAAAGCTGGCGAAGACAGACAAG

AATGCCATGAGAAAATCCGAGTTTGGGCCCAAGAAGCGGGCACTCAAGTC

AAAATTTTGGGCCTTAAAAACGATCTAGTGGACCGAATCAAAAAG

SEQ ID NO: 16
Gene #12
Nucleotides 244-343 of SEQ ID NO: 15
CG3590
adenylosuccinate lyase-like
CTCTGCTCGGATGCTCTCCTCATCACTTTGATGAACATTTTGGAAGGGCT

CGTAGTCTACCCGAAAGTCATTGAAAAGCACATCGGAGAAGAACTTCCTT

SEQ ID NO: 17
Gene #13
CG5451
WD40 repeat-containing protein
SMU1-like isoform 1 (partial)
CAAGCATTGAAGTGGCAACAGCACCAGGGGCTTCTTCCACCAGGTACGAC

ATCGCTTGTCCGTGGTAAAGCTGCGATAAGAGACCAAGACGATGAAAAGT

ACCCAACGCAGTTGTCAAAGCAGATCAAGTTCGGTCACAAGTCCCATGTC

GAATGTGCCACTTTTTCGCCGGACGGGCAATTCCTCGTGTCTGGGAGCGT

TGACGGTTTCATTGAAGTGTGGAATTTCACGACGGGGAAAATCCGAAAGG

ATCTCAAGTACCAAGGCCAGGACAATTTCATGATGATGGAAGAAGCCGTT

TTGGCGCTAGCTTTCAGCCGCGACTCAGAAATGCTTGCGAGCGGTTCCCA

AGAGGGTAAAATCAAAGTGTGGAAAATCGTGACGGGTCAGTGTCTCCGCA

AGTATGAAAAGCCCATTCCAAAGGCGTTACTTGCATCCGATTCTCAAGG

GACAACAGTCAAATCCTCACCGCCTCGTTCGACACGACAATCAAAATTCA

CGGGTTGAAGTCAGGTAAATCGTTGAAGGAATTCCGC

SEQ ID NO: 18
Gene #13
Nucleotides 438-537 of SEQ ID NO: 17
CG5451
WD40 repeat-containing protein
SMU1-like isoform 1
CCGATTCTCAAGGGACAACAGTCAAATCCTCACCGCCTCGTTCGACACGA

CAATCAAAATTCACGGGTTGAAGTCAGGTAAATCGTTGAAGGAATTCCGC

SEQ ID NO: 19
Gene #20
Dhc64C
dynein heavy chain, cytoplasmic-like
(partial)
CAACGGCTACTGTCATCTTTCCTTTCGAAATTGTTCACTCCGCGAAGCTT

TGAGTCGGATTTTGCATTGGTTGCCAACGTTGACGGTGCCCAACGGCACA

TTGTGATGCCGGACGGAACAAGGAGGGATCACTTCCTCCGGTGGATCGAA

GGGTTGTCCGATCGCCAGACACCCGCGTGGCTCGGTCTTCCAAACAACGC

CGAGAAAGTCCTATTGACCAATCGAGGAGCCGATTTGGTCATGAAACTGC

TCAAAATGCAACAATTAGAGGACGAAGACGAGCTCGCCTACACCGAAGAA

GCCGCCGCCAACAATCCAGACGGCCCTTCGTCCGCTCTCCCTGAAGACGC

TAGACCAGCCTGGATGCGCACTTTGTACAATTCCGCAGTTTCCTGGCTCG

AACTCCTCCCCACAAGCCTTCCGACTCTGAAGAGAACTGTGGAAAATATC

AAAGATCCTCTCTACCGGTACTTCGAAAGGGAGGTGAACGCCATCGCCAA

ACTCTTACGTGATGTTGTCCACGATTTAACTGACATAGTCGCGATTTGTC

AAGGTACGAAAAACAAACAAATTACCATAGAACTATGGTTGGGGAGTTG

GTTCGAGGAATGCTCCCGGCATCTTGGCGGCGCTACACAGTTCCCCGCGG

CTGCACAGTAATCCAATGGGTCACCGACTTCAGTAACAGAGTCAAGCAAT

TGGCCCACATATCCCAATTAGCCTCTCAGAGAGGTCCTTCAGAAATAAAG

```
AGTGTCGCTGTATGGCTGGGCGGTCTCACCAACCCCGAGGCTTACGTTAC

TGCTACGCGTCAGTGCATTGCACAAGCTAACAGTTGGTCTTTGGAGGAGC

TTGTGCTCGACGTTACGATTTTGGACAGTTCGGGACAAGTTCCTATCGAC

GGCTCCAGTTTCCCTGTGACTGGGCTGAAGCTTCAAGGAGCTCAATGTAA

AAACAACCAATTGCAGCTCGCCTCGACTATCATGATGGAACTACCCACAA

CTCTTCTTCGCTGGACCAGAATCGGTGACTGCACCAGCGACGGCAAGCTT

TCCCTTCCCGTTTATTTGAATTCAACCCGAAGTGAACTTCTGTTCACGGT

CGACCTCAACGTTCTTCCGGGCCAAGATCCGCACAGTTTCTACGAAAGAG

GAGTCGCTTTGCTTGCTTCAACTGCCCTTAATTAA
```

SEQ ID NO: 20
Gene #20
Nucleotides 146-245 of SEQ ID NO: 19
Dhc64C
dynein heavy chain, cytoplasmic-like
```
TCGAAGGGTTGTCCGATCGCCAGACACCCGCGTGGCTCGGTCTTCCAAAC

AACGCCGAGAAAGTCCTATTGACCAATCGAGGAGCCGATTTGGTCATGAA
```

SEQ ID NO: 21
Gene #24
e(r)
enhancer of rudimentary (full)
```
ATGTCGCACACGATAATGCTCATCCAGCCGGGTACCAAACCTGAGACGAG

AACCTACTCAGACTACGAATCTGTGAACGAGTGTATGGAAGGTGTGTGCA

AAATATATGAGGAGCACTTGAAAAGGCAGAACCCGAACACTCCCGCTATC

ACTTACGACATTAGTCAATTGTTTGACTTCATTGACCAGTTGTGCGATTT

GTCCTGCCTAGTGTACCAGAAAGGCTCCAACACTTACGCCCCCTACAACA

AAGACTGGATCAAAGAGAAGATCTACATTCTGCTCCGACGGCAGGCCAAT

AATCGCCAATAA
```

SEQ ID NO: 22
Gene #24
Nucleotides 178-277 of SEQ ID NO: 21
e(r)
enhancer of rudimentary
```
TTCATTGACCAGTTGTGCGATTTGTCCTGCCTAGTGTACCAGAAAGGCTC

CAACACTTACGCCCCCTACAACAAAGACTGGATCAAAGAGAAGATCTACA
```

SEQ ID NO: 23 + SEQ ID NO: 85
Gene #26
ebi
f-box-like/WD repeat-containing
protein ebi-like (partial/gapped)
SEQ ID NO: 23:
```
GCCCTTGACGTCGACTGGCAAACGAACACGAGTTTTGCCTCGTGCAGTAC

CGACCAGTGTATCCACGTTTGCAAATTAAATGTTGAAAAACCCATCAAGT

CCTTCCAAGGGCACACAAATGAAGTCAACGCGATTAAGTGGGATCCG
```
[gap]

SEQ ID NO: 85:
```
GGAAATCTGTTGGCGTCCTGCTCTGACGATATGACTCTTAAAATTTGGTC

GATGAAACAAGACACGTGTGTGTACGACTTGCAAGCTCACAATAAGGAAA

TTTACACTATCAAGTGGAGCCCAACTGGACCGGGCACACTGAACCCAAT

ATGAATCTTATTTTAGCCAGTGCCTCATTCGATTCTACTGTTCGTCTCTG

GGAAGTGGATCGGGGAGCTTGTATTCACACTTTAACTAAACACACTGAGC

CCGTGTACAGCGTCGCCTTTTCCCCCGACGGTAAATTCTTGGCTTCTGGA

AGCTTCGACAAATGCGTTCATATATGGTCAACTCAGTCGGGGCACTTAGT

TCACAGTTACAAAGGAACGGGTGGGATATTCGAAGTATGTTGGAACTCTC

GGGGCGATAAAGTCGGAGCTAGTGCATCGGACGGAAGCGTATTTGTTTTG

GACCTCCGCAAGCTGTGA
```

SEQ ID NO: 24
Gene #26
Nucleotides 186-285 of SEQ ID NO: 85
ebi
f-box-like/WD repeat-containing protein
ebi-like
```
TACTGTTCGTCTCTGGGAAGTGGATCGGGGAGCTTGTATTCACACTTTAA

CTAAACACACTGAGCCCGTGTACAGCGTCGCCTTTTCCCCCGACGGTAAA
```

SEQ ID NO: 25
Gene #27
EcR
ecdysone receptor isoform A (partial)
```
ATCAAGCCCGTCAGTCCCGAACAAGAAGAGCTCATACACCGTCTCGTATA

TTTCCAAAGCGAGTACGAACATCCGTGTGAAGAGGACGTCCGCCGAATAA

ATGCTCCAAACGACGACGATGAGCCCAACTCAGACTACAGGTTCCGATAC

TTGGCCGAAATCTCCATACTAACTGTTCAACTTATTGTTGAATTTGCAAA

AAGACTTCCTGGATTCGACAAACTTTTGAGGGAAGACCAAATCACTTTAC

TTAAGGCATGTTCAAGCGAAGTGATGATGTTGAGGATGGCTCGGCGGTAC

GACGCACAGACCGACTCGATCCTCTTCGCGAACAACCAACCCTATACCAG

AGACTCGTATAATTTAGCAGGCATGGGAGAAATAGTCGAGGATCTGCTCA

GGTTTTGCCGGCAAATGTACAATATGAAAGTGGACAACGCTGAGTACGCA

CTTCTCACCGCCATCGTTATATTCTCAGAGAGACCGTCACTTATTGAAGG

GTGGAAAGTGGAAAAAATCCAGGAAATCTATTTGGAGGGGCTCAAATCCT

ACGTGGACAACAGGTCGAGGCCTCGATCCCCTACAATATTCGCCAAACTC

CTCTCGGTCCTGACTGAGCTTCGAACACTCGGAAATCAAAATACGGAGAT

GTGTTTCTCATTAAAACTTCAAAATAAGAAACTTCCTCCGTTTTTGTCAG

AAATATGGGACGTA
```

SEQ ID NO: 26
Gene #27
Nucleotides 65-164 of SEQ ID NO: 25
EcR
ecdysone receptor isoform A
```
ACGAACATCCGTGTGAAGAGGACGTCCGCCGAATAAATGCTCCAAACGAC

GACGATGAGCCCAACTCAGACTACAGGTTCCGATACTTGGCCGAAATCTC
```

SEQ ID NO: 27
Gene #28
Ef1 alpha48D
elongation factor 1-alpha-like (partial)
```
ATCGTCGTCATCGGCCACGTCGACTCTGGTAAATCGACGACCACCGGGCA

TTTGATCTACAAATGCGGTGGTATTGACAAACGTACCATTGAGAAGTTCG

AGAAGGAAGCCCAAGAAATGGGAAAAGGTTCCTTCAAGTACGCTTGGGTT

TTGGACAAGCTGAAAGCCGAACGTGAGCGTGGTATCACAATTGACATTGC

GCTCTGGAAGTTCGAAACTGCCAAGTACTACGTTACCATCATTGATGCCC

CCGGTCACAGGGATTTCATCAAGAACATGATCACCGGAACGTCTCAGGCT

GATTGTGCTGTTTTGATCGTTGCTGCTGGTACTGGTGAATTCGAGGCGGG

TATTTCCAAGAACGGACAAACCCGTGAGCACGCTCTCCTCGCTTTCACTC
```

-continued

TCGGTGTGAAACAGCTCATTGTCGGAGTGAACAAAATGGACTCGACTGAG

CCCCCGTACAGCGAGAGCCGTTACGAGGAAATCAAGAAAGAGGTGTCTTC

GTACATCAAGAAAATCGGGTACAACCCAGCGGCTGTCGCTTTCGTTCCCA

TCTCCGGATGGCACGGTGACAACATGTTGGAGGCGTCCGACAAAATGCCC

TGGTTCAAGGGATGGAACGTTGAGAGGAAAGAGGGTAAGGCCGACGGAAA

GTGCCTTATTGAAGCCCTCGACGCCATCCTCCCCCCGTCCCGTCCCACCG

ACAAGGCCCTTCGACTTCCCCTTCAGGACGTGTACAAAATCGGTGGTATC

GGAACAGTGCCCGTCGGCCGAGTCGAAACCGGTCTACTGAAACCTGGTAT

GATCGTTACTTTTGCCCCTGTCAACCTCACGACTGAGGTTAAATCCGTGG

AGATGCACCACGAAGCCCTCCAAGAGGCTGTGCCCGGAGACAACGTCGGA

TTCAACGTTAAGAACGTCTCCGTTAAAGAGTTGCGTCGTGGTTTCGTCGC

CGGCGACTCCAAAAACGCTCCTCCCAAGGCCGCGAGTGACTTCACTGCCC

AAGTCATCGTTCTCAACCATCCCGGTCAAATCGCCAACGGGTACACTCCC

GTCTTGGATTGTCACACTGCCCACATCGCGTGTAAATTCAACGAGATCAA

AGAAAAATGTGACAGACGTACTGGTAAAACCACTGAGCAGAACCCCAAGT

TCATCAAGTCTGGTGACGCCGCTATTGTCACCCTCATCCCGACTAAGCCC

ATGTGCGTCGAGTCTTTCCAGGAGTTCCCTCCCCTGGGACGTTTCGCCGT

GCGTGACATGAGGCAAACCGTCGCTGTCGGCGTCATTAAAAGCGTCACTA

ATAAAGACGTGACGACTGGTAAAGTGACG

SEQ ID NO: 28
Gene #28
Nucleotides 944-1043 of SEQ ID NO: 27
Ef1 alpha48D
elongation factor 1-alpha-like
TCGTCGCCGGCGACTCCAAAAACGCTCCTCCCAAGGCCGCGAGTGACTTC

ACTGCCCAAGTCATCGTTCTCAACCATCCCGGTCAAATCGCCAACGGGTA

SEQ ID NO: 29
Gene #29
Ef1 gamma (full)
ATGGCGTCAGGAACTTTGTACACTTACTCGGGAAATTTCCGCGCGTACAA

AGCCCTCATTGCGGCCGAATACGGGGCGGTTCGGTCAAAGTGGCACCGG

ATTTTGTCTTCGGCGAAACGAACAGGACTCCTAATTTTCTCAAGAAATTC

CCCCTGGGAAAGGTGCCTGCTTTCGAAAGTACCGACGGCACATGTGTCAC

CGAAAGCAACGCCATAGCCTGGTTCGTTGCCAGTCCAGAATTGAGAGGGA

AGTCTGACGCGAAAAAGCTCAAATTGTTCAATGGTTGAGCTACTCAGAC

TCCGAAGTTCTTCAAGCCACTTGTACTTGGGTCTTCCCCTACCTCGGTAT

CCTTCCCTTCAACAAATCCGAAGTTCAAAAAGGCGGCAAAGAAGCCCTTC

AAGCCATTCTGAAATGCCTGAATTCGTATTTGCTCACGAGGACTTATCTA

GTGGGTGAAGCAATTACTTTGGCCGACATCGTACTCACATGCACGCTTCT

CCCTGCCTACCAGACTGTCTTAGACCCTAGCTTCAGGAAGGAGTTCCAAA

ATGTCAACCGGTGGTTCAACACTATCGTCAATCAGCCAAAAGTCAAAAAA

GTCTTGGGAGATGTCAAACTCTGTGACAAAGAGCCCGTCATCCCTGCTCC

TGATGGGAAGAAGAAAGAGAAGGCAGAAAAGCCTCAGGGGACGCTCAAC

CCAAAAAAGAGAAAAAAGCTGCGAAACCTGCGGAGGAGGAGGAAATGGAC

GCGGCGGAAGCTGCCCTGGCCGCTGAGCCCAAGTCCAAAGACCCCCTTGA

CGCACTGCCCAAAGGGACATTCGTCATGGACGACTTCAAACGAGTTTACT

CCAACGAGGACGTTGATAAGTCCATTCCGTACTTTTGGGAGAAATTCGAC

AAAGAAAACTACTCGATTTGGTTGGGCGAGTACTTGTACAACGACGAGCT

GCAAAAGGTCTTCATGAGCTGCAACCTCATCACCGGCATGTACCAGAGAC

TGGACAAAATGAGGAAAAACGCTTTCGCCTCCGTCATTCTGTTCGGCAAA

GACAACGACAGCACCATTTCCGGTGTTTGGGTGTGGCGAGGCCAAGATCT

TGCTTTCAAAATGAGCCCTGACTGGCAAGTGGACTACGAGTCGTACAAAT

GGTCCAAACTCGACCCGACTAATCAAGAACACAAAAAAATGGTCGATAAT

TATATGGCGTGGACAGGAACGGACAAACAAGGCCGCCCATTCAATCAAGG

GAAAATCTTCAAATGA

SEQ ID NO: 30
Gene #29
Nucleotides 951-1050 of SEQ ID NO: 29
Ef1 gamma
GCAAAAGGTCTTCATGAGCTGCAACCTCATCACCGGCATGTACCAGAGAC

TGGACAAAATGAGGAAAAACGCTTTCGCCTCCGTCATTCTGTTCGGCAAA

SEQ ID NO: 31
Gene #30
eIF-2alpha
eukaryotic translation initiation factor
2 subunit 1-like isoform 1 (partial)
TACATCGATCTCAGCAAAAGAAGAGTTTCGCCTGAGGACGTTGAAAAATG

CACTGAGAGATTTGCCAAGGCCAAAGCTGTCAACTCAATTTTGAGACACG

TCGCTGAGCTCCTCCACTACGACGCCGATGAACAGCTGGAGGACCTCTAC

CAGCGAACGGCGTGGTTTTTCGAAGAGCGAACCAAGAAGAAGTCCTCTGC

CTACGATTTCTTCAAACAAGCTGTTCTTGACAACTCAATTTTGGCTGAGT

GCGGACTTGACGAAGCTACTCAGGAAGTCCTTTTGACCAATATCAAGAGG

AAATTGACGTCGCAGGCCGTCAAAATCAGAGCTGACATCGAAGTAGCTTG

TTACGGCTACGAAGGGATTGACGCTGTTAAAACTGCACTCAAGGCCGGTT

TAGCACTCTCCACCGAAGAACTTCCAATCAAAATCAATCTTATTGCTCCT

CCACTATATGTCATGACGACAGCCACTCCTGAAAAAGCTGATGGGCTCAA

AGCCCTTCAAAATGCGATCGAAGTCATCGAAAAGGAAATCACCAGTCTTG

GCGGTGTCTTTCAAGTCGAAATGGGCCCAAAGTCGTTACAGCGACGGAC

GAAGCGGAATTGGCTAAACAAATGGAAAGAGCTGAGGCCGAAAATGCCGA

AGTGGCCGGG

SEQ ID NO: 32
Gene #30
Nucleotides 90-189 of SEQ ID NO: 31
eIF-2alpha
eukaryotic translation initiation factor
2 subunit 1-like isoform 1
TTTGAGACACGTCGCTGAGCTCCTCCACTACGACGCCGATGAACAGCTGG

AGGACCTCTACCAGCGAACGGCGTGGTTTTTCGAAGAGCGAACCAAGAAG

SEQ ID NO: 33
Gene #31
eIF3-S8
eukaryotic translation initiation factor
3 subunit C-like isoform 1 (partial)
GAGCACTTGTACTACAAATTCGACCCGACTGTCATTCAACAGAGAAAGGG

CGAATTGGAACCAGGCACCCAAACTAGCATCCAAGTGATGGACAAATTGT

-continued

GCAAGTACATTTACGACAAGGACCAAACAGATCGGCTGAGAACGAGGGCC

ATTCTGGCCCACGTGTACCATCACGCGTTGCACGACAATTGGTTCCAAGC

TCGGGACCTCATCCTCATGTCACATCTTCAAGAAGCCATACAACATTCCG

ATCCATCTACCCAGATCCTGTACAACCGTACTATGGCCCATTTGGGACTT

TGCGCCTTCCGCCACGCGAACATCAAAGATGCCCACAATTGCTTAGTGGA

CTTGATGATGACTGGAAAAACGAAAGAACTTTTGGCCCAGGGACTCATGC

CGCAGAGGCAGCACAACGAAGCAAAGAACAAGAAAAAGTTGAAAAACAG

AGACAAATGCCGTTCCACATGCACATTAACTTGGAGTTGATCGAGTGCGC

TTATTTAGTGTCAGCTATGCTCATTGAAATTCCTTACATGGCCGCTCATG

AATTCGATGCACGGAGAAGGATGATCTCCAAAACGTTCTATCAGCAGTTG

AGAAGCAGCGAACGACAGTCATTGGTCGGTCCTCCAGAAAGTATG

SEQ ID NO: 34
Gene #31
Nucleotides 21-120 of SEQ ID NO: 33
eIF3-S8
eukaryotic translation initiation
factor 3 subunit C-like isoform 1
CGACCCGACTGTCATTCAACAGAGAAAGGGCGAATTGGAACCAGGCACCC

AAACTAGCATCCAAGTGATGGACAAATTGTGCAAGTACATTTACGACAAG

SEQ ID NO: 35
Gene #32
eIF5
eukaryotic translation initiation
factor 5-like isoform1 (partial)
ATGGGCAGCGTCAACGTGAACCGGTCCGTTTCCGATGCCTTCTATCGGTA

CAAGATGCCGCGCCTCCTCGCTAAGGTCGAGGGCAAAGGGAACGGCATAA

AAACGGTCATAGTGAACATGGCAGACGTCGCTAAGGCTCTCGGTCGGCCA

GCCACCTACCCAACCAAGTACTTCGGATGCGAACTCGGAGCTCAGACTTT

GGTGGATTTCAAGAACGACAGATTCATCGTGAACGGGTCCCATGACGCGG

CCAAACTGCAGGACCTCCTCGACGGGTTCATTCGGAAATTCGTGCTCTGC

CCCGAATGCGACAACCCTGAAACTGATCTTCTCGTCAATTCGAAGAAAGA

GACGATCAGTCAAGGGTGCAAGGCCTGCGGCTTCCACGGCCTCCTCCAGT

TCAACCACAAACTGAACATGTACATTATCAAAAATCCACCAAACATGAAT

CCGGCTACACAGGGCGCTTCTCTGACCGAAGGGAAAAGAGCTCGTCGGTC

CAAAGCCAAGCAAAACGGCGACGTCACCAACGGAGACCGTTCCGGTTCAC

CCAAGTCAGAAGACGAGCCCGAGCTCATCGTCGCTCCTACAAAGAACATC

GAAAATAAAAACGACGACGACCTCCAATGGGCCGTCGACGTCTCCGAAGA

AGCCGTCCGAGCTCGTCTTCAAGACCTGACCGACGGAGCTAAAAACCTGA

CCTTAACTGATGATCTTGAGAAACCAGAAAACGAGCGGATGGACATTTTC

TACGTGATGGTGAAACAGAGGCGGGACACAGGCGATTTGTCGACTCCACT

CGCCGCCAAGGAGATCCTCGCCGAAGCGGAGCGACTTGAAATCAAAACCA

AAGCTCCACTTGTCCTCGCTGAGCTTCTTTTTGACGACAAAATCCACGTT

CAGATCAAGCGCTACCGTTTTTGTTTCTTCGTTTCACTCATCAAGATAC

TAAAGCTCAAAAAGCTCTGATTGGAGGCATCGAGCAGATCATTGGTTTGC

ACAAGGCTTCGCTCCTGCCTAAAGTACCCGCGATCTTGAAACTTTTGTAT

GACCTGGATATACTGGAGGAAGGTGTGATTCTTCAATGGGGAGAAAAGC

GAGTAAAAAATACGTGTCCAAAGAGCTGAGTCAAGAGATACATAGTAAAG

CCACGCCTTTCTTAACTTGGTTGAAA

SEQ ID NO: 36
Gene #32
Nucleotides 741-840 of SEQ ID NO: 35
eIF5
eukaryotic translation initiation
factor 5-like isoform1
GGACATTTTCTACGTGATGGTGAAACAGAGGCGGGACACAGGCGATTTGT

CGACTCCACTCGCCGCCAAGGAGATCCTCGCCGAAGCGGAGCGACTTGAA

SEQ ID NO: 37
Gene #34
hay
DNA excision repair protein
haywire-like (partial)
TATATTTACGGTCCAACTTCTCAGAACGAAAGGATCCAAATTCTACAAAA

TTTCAAATTCAATCCCAAAGTAAATACGATTTTTGTGAGTAAAGTTGCCG

ATACGTCGTTTGATCTTCCCGAGGCTAATGTACTGATTCAAATATCCTCT

CATGGAGGCTCTCGACGTCAAGAAGCTCAGAGATTGGGTAANAATTCTCA

GAGCCAAAAAAGGGAGCGATCGCTGAAGAGTATAATGCGTTTTTTCCTA

CACACTCGTTTCCCAAGACACGATGGAAATGGCGTATTCGCGGAAGCGCC

AAGCGGTTCCTCGTCAATCAGGGCTACAGTTACAAAGTGGTGACGAAATT

GGCTGGTATCGACCAAGNTCCTGACATAATGTACAAAACCCGNGACGAG

SEQ ID NO: 38
Gene #34
Nucleotides 300-399 of SEQ ID NO: 87
hay
DNA excision repair protein haywire-like
CAAGCGGTTCCTCGTCAATCAGGGCTACAGTTACAAAGTGGTGACGAAAT

TGGCTGGTATCGACCAAGATCCTGACATAATGTACAAAACCCGAGACGAG

SEQ ID NO: 39 + SEQ ID NO: 86
Gene #35
Hel25E
ATP-dependent RNA helicase WM6-like
(partial/gapped)
SEQ ID NO: 39:
GTTCTCGGCATGGACATCCTTTGCCAGGCCAAATCAGGTATGGGAAAAAC

GGCCGTGTTCGTCCTGGCGACTCTGCAACAAATGGAATTGACCGAAAACC

AAGTGACGGTCTTGGTCATGTGCCACACGAGGGAACTTGCTTTCCAAATA

TCCAAAGAGTACGAGCGATTCTCCAAGTACATGCCGCACATTAAGGTGGC

CGTATTCTTCGGTGGTTTACCCATTGCAAAAGATGAGGAAACTTTGAAAA

ACAATTGTCCTCACATTGTGGTCGGGACTCCGGGACGGATCCTTGCTCTT

GTCCGCAATAAAAAATTGAGTTTGAAGAATTTGAAACATTTCATTTTGGA

TGAATGCGACAAAATGTTGGAGCAACTTGATATGAGACGCGACGTACAGG

AGATATTTCGACAAACTCCACACAGTAAACAAGTGATGATGTTCAGTGCC

ACTTTGAGCAAGGACATACGTCCCGTCTGCAAGAAGTTCATGCAAGAACC

GATGGAAGTCTACGTTGATGACGAGGCCAAACTCACACTTCACGGTCTGC

AACAACACTACGTTAAATTAAAGGAAAACGAG [gap]

SEQ ID NO: 86:
CTTTTTTGATTTACTTGACATATTGGAGTTCAACCAGGTGGTCATTTTCGT

CAAGTCTGTTCAACGGTGTATGGCTCTTGCTCAGCTCTTATGCGACCAAA

ACTTCCCGGCTGTCGCGATCCACAGAGCCATGAATCAAGAGGAGCGGCTC

TCGAAATATCAAGAATTTAAAGACTTCCAAAAGAGGATTCTTGTGGCGAC

CAATCTCTTTGGCCGAGGAATGGACATAGAGAGAGTGAACATTGTTTTCA

ACTACGACATGCCCGAAGACTCAGACACTTATTTACATCGTGTGGCTCGG

GCTGGTCGTTTTGGAACTAAGGGTTTGGCCATCACGTTTGCCAGTGACGA

AAACGACGCCAAAGTTCTCAATCAAGTACAGGACCGATTTGATGTCAACA

TTACTGAGTTACCTGACGAGATTGATCTGTCATCTTACATTGACGGCCGG

SEQ ID NO: 40
Gene #35
Nucleotides 15-114 of SEQ ID NO: 86
Hel25E
ATP-dependent RNA helicase WM6-like
TGACATATTGGAGTTCAACCAGGTGGTCATTTTCGTCAAGTCTGTTCAAC

GGTGTATGGCTCTTGCTCAGCTCTTATGCGACCAAAACTTCCCGGCTGTC

SEQ ID NO: 41
Gene #37
Hr38
ecdysone receptor isoform B1 (partial)
ATCAAGCCCGTCAGTCCCGAACAAGAAGAGCTCATACACCGTCTCGTATA

TTTCCAAAGCGAGTACGAACATCCGTGTGAAGAGGACGTCCGCCGAATAA

ATGCTCCAAACGACGACGATGAGCCCAACTCAGACTACAGGTTCCGATAC

TTGGCCGAAATCTCCATACTAACTGTTCAACTTATTGTTGAATTTGCAAA

AAGACTTCCTGGATTCGACAAACTTTTGAGGGAAGACCAAATCACTTTAC

TTAAGGCATGTTCAAGCGAAGTGATGATGTTGAGGATGGCTCGGCGGTAC

GACGCACAGACCGACTCGATCCTCTTCGCGAACAACCAACCCTATACCAG

AGACTCGTATAATTTAGCAGGCATGGGAGAAATAGTCGAGGATCTGCTCA

GGTTTTGCCGGCAAATGTACAATATGAAAGTGGACAACGCTGAGTACGCA

CTTCTCACCGCCATCGTTATATTCTCAGAGAGACCGTCACTTATTGAAGG

GTGGAAAGTGGAAAAAATCCAGGAAATCTATTTGGAGGGGCTCAAATCCT

ACGTGGACAACAGGTCGAGGCCTCGATCCCCTACAATATTCGCCAAACTC

CTCTCGGTCCTGACTGAGCTTCGAACACTCGGAAATCAAAATACGGAGAT

GTGTTTCTCATTAAAACTTCAAAATAAGAAACTTCCTCCGTTTTTGTCAG

AAATATGGGACGTAAACGTACCTTAG

SEQ ID NO: 42
Gene #37
Nucleotides 559-658 of SEQ ID NO: 41
Hr38
ecdysone receptor isoform B1
AACAGGTCGAGGCCTCGATCCCCTACAATATTCGCCAAACTCCTCTCGGT

CCTGACTGAGCTTCGAACACTCGGAAATCAAAATACGGAGATGTGTTTCT

SEQ ID NO: 43
Gene #40
mask
hypothetical protein (partial)
GAAGTTGTGAGTCTTTTACTGGATCGTCGAGCCAATGTAGAACATCGCGC

CAAGACTGGTTTGACGCCTTTGATGGAAGCTGCAAGTGGAGGATATGTTG

AAGTTGGACGAGTCCTGCTTGACAAAGGAGCTGACGTGAACGCACCACCT

GTTCCTTCGTCCCGGGACACGGCTCTCACCATAGCCGCTGACAAAGGGCA

TTGCCGTTTTGTTGAACTTCTCCTCAGCAGAAATGCTCAAGTTGAAGTGA

AAAACAAAAAGGAAACTCTCCCTTGTGGCTCGCAGCAAATGGAGGTCAC

CTAACTGTGGTCGAGTACCTGTACAATGCTGGTTCGGACATCGATTCCCA

AGATAACCGCAAGGTCTCATGTCTGATGGCCGCGTTCCGAAAGGGCCATG

TAAAAGTGGTCAAATGGATGGTGAACGCTGTCACCCAATTCCCAAGTGAC

CAAGAAATGACTAGGTACATTGGCACGGTCAATGATAAAGAACTACTTGA

AAAATGTCAAGAGTGCACGAAAATCATAAGAACCGCCAAAGACCAGCAAG

CTGCCAAAGCGAATAAAAACGCGACGATCCTCCTTGAAGAACTTTACATG

GAGAAAACGCGAGAAGAG

SEQ ID NO: 44
Gene #40
Nucleotides 208-307 of SEQ ID NO: 43
mask
hypothetical protein
TTTGTTGAACTTCTCCTCAGCAGAAATGCTCAAGTTGAAGTGAAAAACAA

AAAAGGAAACTCTCCCTTGTGGCTCGCAGCAAATGGAGGTCACCTAACTG

SEQ ID NO: 45
Gene #41
mor
SWI/SNF complex subunit SMARCC2-like
(partial)
GTGTTCAAGTATAAAACGGAACAGGGGTGGAGGAGGTTCGACTTCCAGAG

CCCCAGCCGTATGGACAGAAACGTCGAGATGTTCATGGCCATTGAAAAGG

CCTTAATTCAAGCCAAATGTTTCACTCTGCCAGTCGTCTACGTCCGGCCC

GAAGTTGAAAAAGCGACTGCAGCCAAAGTCAAAGACATAATCAAACGCCA

CCAGGGAACGGTGGTCGAAAACGAAGAACAGGCGACCCACATCCTTTACC

CTATTGTGGATCCTTTGGATGAGGAATTCGCTCGACCTACCCTGAAAAGG

GATCGTATGGCTTTGCTCCATTGGTACTATTTCCCGGATTCGCATGATTC

TTGGGTTGCTTCAGATCTCCCGGTCGATCCACCTGATTCACCCGTTCAAC

ACACTCTGCCTTGGAGGGTCACCGCGTCTTGGGCCATTGAACTCGAACAG

TACAACGAATGGATGAACGAAGAAGATTACGAAGTCGACGAAACTGGACG

GAAAAAAATTCACAGACTTCGTTTATCCGTCGACGATCTCATG

SEQ ID NO: 46
Gene #41
Nucleotides 159-258 of SEQ ID NO: 45
mor
SWI/SNF complex subunit SMARCC2-like
AAAAGCGACTGCAGCCAAAGTCAAAGACATAATCAAACGCCACCAGGGA

ACGGTGGTCGAAAACGAAGAACAGGCGACCCACATCCTTTACCCTATTGT

G

SEQ ID NO: 47
Gene #47
RpS2
40S ribosomal protein S2-like (partial)
AAGGAAACCGAGAAAGAATGGATGCCTGTCACCAAATTGGGCCGTTTGGT

CAGAGATGGCAAAATCGGTACTCTTGAGGAGATCTACCTCTACTCCCTTC

CCATCAAGGAGTATGAAATCATCGACTTTTTCATTGGGCCCAGCCTCAAG

GATGAAGTGCTGAAGATCATGCCGGTTCAGAAGCAGACTCGAGCCGGGCA

AAGGACTCGATTCAAGGCGTTTGTTGCCATCGGCGACAGCAACGGTCATA

TCGGTCTTGGAGTCAAGTGTTCCAAAGAAGTAGCGACGCCATCCGTGGC

GCTATCATTCTAGCCAAGTTGTCCGTTGTGCCCGTTCGTCGAGGTTACTG

GGGAAACAAAATCGGAAAACCCCACACTGTTCCGTGCAAGGTGACCGGTA

-continued
AATGTGGCTCAGTCCAGGTGAGGCTTATCCCGGCCCCAAGAGGAACTGGT

ATTGTCGGCGCTCCTGTTCCTAAGAAGTTGCTCCAAATGGCAGGAATTGA

CGATTGTTACACTTCATCCCGTGGCTCCACCGGAACTTTGGGCAATTTTG

CTAAAGCAACTTACGCGGCTATTGCGAAGACCTACGCGTATTTGACTCCG

GATCTGTGGAAGGATGAGCCGCTCGGCCGACCCCCATACAGTGAGTTTGC

GGACCATTTGGACAAAAATCAC

SEQ ID NO: 48
Gene #47
Nucleotides 573-672 of SEQ ID NO: 47
RpS2
40S ribosomal protein S2-like
TGCGAAGACCTACGCGTATTTGACTCCGGATCTGTGGAAGGATGAGCCGC

TCGGCCGACCCCCATACAGTGAGTTTGCGGACCATTTGGACAAAAATCAC

SEQ ID NO: 49
Gene #48
RpS5a
40S ribosomal protein S5-like
isoform 1 (partial)
ATGGACGAGGACAATTGGGATGTGACCCCTGTCGAGGGTGGCGGAGTCGA

GGCTTTGGTCCCGGCCCCATCAGCTGAACTTCCTGACATCAAGTTGTTCG

GCAGGTGGAGCTGCGACGATGTCCAAGTGGCCGATATGTCTCTCCAGGAT

TACATTGCGGTAAAAGAGAAAAACGCCAAGTATTTGCCTCATTCGGCTGG

TCGGTTCGCGGCCAAGAGGTTCCGCAAGGCCCAGTGCCCCATCGTCGAGC

GGTTGACCAATTCGTTAATGATGCACGGGAGAAACAACGCCAAGAAACTG

ATGGCTGTTCGCATAGTCAAACACGCTTTTGAAATTATTCATCTGCTGAC

TGGCGAAAACCCGCTGCAAACCCTTGTCAACGCCATCACTCACTCTGGCC

CACGCGAGGACTCAACTCGTATCGGTCGTGCCGGTACGGTGAGGCGACAA

GCAGTTGACGTTTCGCCTCTTCGACGAGTCAATCAGGCGATTTGGCTCCT

CTGTACTGGTGCTCGTGAAGCGGCTTTCCGAAACATTAAAACCATCGCTG

AGTGTTTAGCTGATGAGCTCATCAACGCCGCTAAGGGATCGTCGAATTCG

TACGCTATCAAGAAGAAAGACGAACTGGAGCGCGTTGCCAAATCCAACCG

TTAA

SEQ ID NO: 50
Gene #48
Nucleotides 1-100 of SEQ ID NO: 49
RpS5a
40S ribosomal protein S5-like isoform 1
ATGGACGAGGACAATTGGGATGTGACCCCTGTCGAGGGTGGCGGAGTCGA

GGCTTTGGTCCCGGCCCCATCAGCTGAACTTCCTGACATCAAGTTGTTCG

SEQ ID NO: 51
Gene #53
Trip1
eukaryotic translation initiation
factor 3 subunit 2 beta-like (partial)
GTTGACGGGCACAACGGGTCAATCAACGACATGCAGATGCACTGGGACGG

CACCATGTTTGTGACAGCTTCGAGTGACCACACAGCAAAGCTATTCGACA

CCGAGTCCCTCAGCCATTTGAAAACATACCAGACCGAAAGACCTGTTAAC

AGCGCCTCGCTTTCCCCTATTATGGACCATGTTGTACTCGGAGGTGGTCA

AGAAGCGTCTGTTGTCACGACTACATCTACTCGCGTGGGAAAATTCGACG

CTCGGTTCTACCACGTTGTTTTTGAAGAGGAATTCGGTCGGGTTAAAGGT

CATTTCGGGCCGATCAACAGTTTGGCGTTTCATCCGGATGGAAAGAGCTT

-continued
TGCAAGTGGAGGTGAAGACGGTTACGTCCGTGTTCAGTCATTCGATCAAT

CGTACTTTGAATTTAATTTCGAG

SEQ ID NO: 52
Gene #53
Nucleotides 1-100 of SEQ ID NO: 51
Trip1
eukaryotic translation initiation
factor 3 subunit 2 beta-like
GTTGACGGGCACAACGGGTCAATCAACGACATGCAGATGCACTGGGACGG

CACCATGTTTGTGACAGCTTCGAGTGACCACACAGCAAAGCTATTCGACA

SEQ ID NO: 53
Gene #54
tws
protein phosphatase PP2A 55 kDa reg-
ulatory subunit-like isoform 3 (partial)
ATAAAACCGATGGAATTAATGGTCGAGGCATCACCTCGGAGAATCTTCGC

CAACGCCCACACGTACCACATTAATTCAATATCTGTCAACTCGGACCAAG

AAACGTATCTGTCCGCTGATGACCTCCGAATAAATCTGTGGCATTTGGAA

ATAACGGATCAGTCCTTCAATATAGTTGACATTAAGCCAGCTAATATGGA

AGAGCTCACAGAGGTAATCACTGCGGCCGAGTTTCACCCATTAGAGTGTA

ATCTATTCGTGTATTCATCGAGTAAGGGAACGATACGGTTGTGCGACATG

AGGCAGGCGGCGCTTTGTGATCGACACACGAAAATTTTTGAAGAACCCGA

AGACCCAACGAACAGATCGTTTTTCTCTGAAATAATTTCCAGCATTTCGG

ACGTGAAACTGTCCAATTCCGGGCGGTACATGATCTCTAGGGATTATCTC

TCGGTGAAAGTCTGGGACCTTCACATGGAGTCGAGGCCTATTGAAAGTTA

TCCTGTTCACGAGTATTTGAGGTCTAAACTCTGCTCTCTGTACGAGAACG

ACTGTATCTTCGACAAATTCGAGTGCTGTTGGGCCGGCAACGACCAGTAC

ATCATGACCGGCTCGTACAATAATTTCTTCCGCATGTTTGATCGGACCTC

CAAACGCGACGTGACCCTGGAGGCGTCCCGGGACATCGCCAAACCGAAAA

CCCTTCTGAAACCCCGAAAAGTCTGCACTGGAGGGAAACGGAAAAAAGAT

GAGATTTCGGTCGACTGTTTGGATTTTACGAAGAAGATCCTTCACACCGC

TTGGCATCCAACCGAGAACATTATTGCAGTGGCCGCCACCAACAATTTAT

TTCTATTTCAGGATCGATTGTAG

SEQ ID NO: 54
Gene #54
Nucleotides 753-852 of SEQ ID NO: 53
tws
protein phosphatase PP2A 55 kDa
regulatory subunit-like isoform 3
GATTTCGGTCGACTGTTTGGATTTTACGAAGAAGATCCTTCACACCGCTT

GGCATCCAACCGAGAACATTATTGCAGTGGCCGCCACCAACAATTTATTT

SEQ ID NO: 55
Gene #55
Ubc-E2H
ubiquitin-conjugating enzyme E2
H-like (partial)
AAAGTGAGAGTCCATCTTCCAGAGCACTATCCGTTCAAAATCTCCATCGA

TAGGATTATGAATAAAGTTTATCATCCAAATATTGATGAGGTCTCAGGCA

CCGTGTGTTTGGATGTCATCAATCAGGCTTGGACAGCCTTATACGATCTG

TCTAACATTTTTGAATCTTTTCTGCCGCAGTTATTGACTTATCCTAATCC

CATAGATCCTCTGAACGGCGATGCCGCAGCAATGTACCTTCATAAACCTG

```
ACGAGTATCGGAAAAAAGTTCACGAATATGTTCGGAAGTACGCCACCGAA

GAAGCACTTAGAGAACAAGAACAACAAGCAGTTTCTTCAGACAGCGAATC

CTCAATGTCAGATTTCAGTGAAGATGAGGCGCAAGATATGGAGTTATAA
```

SEQ ID NO: 56
Gene #55
Nucleotides 267-366 of SEQ ID NO: 55
Ubc-E2H
ubiquitin-conjugating enzyme E2 H-like
```
AGTTCACGAATATGTTCGGAAGTACGCCACCGAAGAAGCACTTAGAGAAC

AAGAACAACAAGCAGTTTCTTCAGACAGCGAATCCTCAATGTCAGATTTC
```

SEQ ID NO: 57
Gene #56
Uev1A
ubiquitin-conjugating enzyme-like (partial)
```
ATGGCCAGTCCTACAGGACGAGTGGTGGTTCCGAGGAACTTCCGCCTCCT

CGAGGAGCTTGAACAGGGACAGCGCGGAGTGAGCGACGGCACTATATCAT

GGGGTCTGGAAACCGTCGACGATATGACTCTCACTTATTGGACCGGCGTC

ATTATCGGCCCACCCCGAACCCCATATGAAAATCGCATGTACAGTTTACG

AATAGAGTGTGGTCAGAAGTACCCGGAAGACGCTCCCTCGGCCCGATTTA

TATCTAGAATTAATATGACCTGCGTTAATAGTACTACAGGACAGGTTGAG

AATAAAAGTGTACCCTTGTTGGCAAGATGGCAAAGGGACTACACCATTAA

ATCACTCCTTCAGGAGCTTCGTCGTCTGATGACGATAAAAGACAACATGA

AACTAACACAGCCACCAGAAGGAAGCAATTTTCCCGAGTGGCAGGTTAAA
```

SEQ ID NO: 58
Gene #56
Nucleotides 181-280 of SEQ ID NO: 57
Nuc
Uev1A
ubiquitin-conjugating enzyme-like
```
AATCGCATGTACAGTTTACGAATAGAGTGTGGTCAGAAGTACCCGGAAGA

CGCTCCCTCGGCCCGATTTATATCTAGAATTAATATGACCTGCGTTAATA
```

SEQ ID NO: 59
Gene #56
Nucleotides 181-280 of SEQ ID NO: 57
with T→C mutation at position 253 of
SEQ ID NO: 57 to create Xba I site Nuc
Uev1A
ubiquitin-conjugating enzyme-like
```
AATCGCATGTACAGTTTACGAATAGAGTGTGGTCAGAAGTACCCGGAAGA

CGCTCCCTCGGCCCGATTTATACCTAGAATTAATATGACCTGCGTTAATA
```

SEQ ID NO: 60
P1 - CaMV 35S Promoter & Omega UTR
```
AGATTAGCCTTTTCAATTTCAGAAAGAATGCTAACCCACAGATGGTTAGA

GAGGCTTACGCAGCAGGTCTCATCAAGACGATCTACCCGAGCAATAATCT

CCAGGAAATCAAATACCTTCCCAAGAAGGTTAAAGATGCAGTCAAAAGAT

TCAGGACTAACTGCATCAAGAACACAGAGAAAGATATATTTCTCAAGATC

AGAAGTACTATTCCAGTATGGACGATTCAAGGCTTGCTTCACAAACCAAG

GCAAGTAATAGAGATTGGAGTCTCTAAAAAGGTAGTTCCCACTGAATCAA

AGGCCATGGAGTCAAAGATTCAAATAGAGGACCTAACAGAACTCGCCGTA

AAGACTGGCGAACAGTTCATACAGAGTCTCTTACGACTCAATGACAAGAA

GAAAATCTTCGTCAACATGGTGGAGCACGACACACTTGTCTACTCCAAAA

ATATCAAAGATACAGTCTCAGAAGACCAAAGGGCAATTGAGACTTTTCAA

CAAAGGGTAATATCCGGAAACCTCCTCGGATTCCATTGCCCAGCTATCTG
```

```
TCACTTTATTGTGAAGATAGTGGAAAAGGAAGGTGGCTCCTACAAATGCC

ATCATTGCGATAAAGGAAAGGCCATCGTTGAAGATGCCTCTGCCGACAGT

GGTCCCAAAGATGGACCCCCACCCACGAGGAGCATCGTGGAAAAAGAAGA

CGTTCCAACCACGTCTTCAAAGCAAGTGGATTGATGTGATATCTCCACTG

ACGTAAGGGATGACGCACAATCCCACTATCCTTCGCAAGACCCTTCCTCT

ATATAAGGAAGTTCATTTCATTTGGAGAGAACACGGGGGACTCTAGATAT

TTTTACAACAATTACCAACAACAACAAACAACAAACAACATTACAATTAC

TATTTACAATTACA
```

SEQ ID NO: 61
sgFiMV Promoter
```
TTTACAGTAAGAACTGATAACAAAAATTTTACTTATTTCCTTAGAATTAA

TCTTAAAGGTGATAGTAAACAAGGACGATTAGTCCGTTGGCAAAATTGGT

TCAGCAAGTATCAATTTGATGTCGAACATCTTGAAGGTGTAAAAAACGTT

TTAGCAGATTGCCTCACGAGAGATTTTAATGCTTAAAAACGTAAGCGCTG

ACGTATGATTTCAAAAAACGCAGCTATAAAAGAAGCCCTCCAGCTTCAAA

GTTTTCATCAACACAAATTCTAAAAACAAAATTTTTTAGAGAGGGGGAGT

G
```

SEQ ID NO: 62
AtActin7 Terminator including 3UTR
```
GTGTGTCTTGTCTTATCTGGTTCGTGGTGGTGAGTTTGTTACAAAAAAAT

CTATTTTCCCTAGTTGAGATGGGAATTGAACTATCTGTTGTTATGTGGAT

TTTATTTTCTTTTTTCTCTTTAGAACCTTATGGTTGTGTCAAGAAGTCTT

GTGTACTTTAGTTTTATATCTCTGTTTTATCTCTTCTATTTTCTTTAGGA

TGCTTGTGATGATGCTGTTTTTTTTTTGTCCCTAAGCAAAAAAATATCATA

TTATATTTGGTCCTTGGTTCATTTTTTTGGTTTTTTTTTGTCTTCACATA

TAAATATTGTTTGAATGTCTTCAATCTTTTATTTGTATGAGACAATTATT

TAAGTATCGGGTGACAATGCAGCTATTATGTATTGTCGATTGTTATATTG

GCGCCCAAAATATATACTTAGCCTAAGAATTTGGTAAGTGAGTGGCTTAT

GTTTTACTCCAGCAAAAATTGTGTGTGTATTACCATTCTGATGCGAAACA

AGAAAAGAATTTGATCTAAGAAACCAAGTTTATTCACTAGTTAAAAAACA

AATGACCTAATGTAATCGACTCCACATATCAAAATACGTAAAACAAACAT

TGTATGTTGACAAAAGGGAAAAGAAATGATTTATTTGGTTAAAAAGAAAG

CTGGATTCAATTGCAACAGTTTAGTCGAAATCATTTTGAAAGGCTTACAA

TGGATTGAATGTGAATATTCCATTAAGCCGCTTCTGTCTACACAGAATGT

TACGCTGGAGAGCAGCAATCATTTTCACGTTTTTATCTTTTTAGGTGGA

CATGTATATTATTGGTTACGCCTTTGGAGTTTTTCGAAATTTATTTCTTT

CAAATCACAAGATGACTAAACATCACAATCTGTTTATCTTCCTAACTAGT

TAAATTTTTGTCCCCACCATT
```

SEQ ID NO: 63
NOS Terminator
```
GATCGTTCAAACATTTGGCAATAAAGTTTCTTAAGATTGAATCCTGTTGC

CGGTCTTGCGATGATTATCATATAATTTCTGTTGAATTACGTTAAGCATG

TAATAATTAACATGTAATGCATGACGTTATTTATGAGATGGGTTTTTATG
```

-continued
ATTAGAGTCCCGCAATTATACATTTAATACGCGATAGAAAACAAAATATA
GCGCGCAAACTAGGATAAATTATCGCGCGGTGTCATCTATGTTACTAG
ATC SEQ ID NO: 64
Loop Sequence
GGCTCGAACGAGCCGACTAATTGTCTTTAAACGCGCGATATAAGCGCACA
ATGCTCGAGAAACGATAAACTCTATCGCTCTGTCGCGTGCGTGGCATCTT
CGCGCG SEQ ID NO: 65
Construct 1, hpRNA
CTCTGCTCGGATGCTCTCCTCATCACTTTGATGAACATTTTGGAAGGGCT
CGTAGTCTACCCGAAAGTCATTGAAAAGCACATCGGAGAAGAACTTCCTT
CCGATTCTCAAGGGACAACAGTCAAATCCTCACCGCCTCGTTCGACACGA
CAATCAAAATTCACGGGTTGAAGTCAGGTAAATCGTTGAAGGAATTCCGC
GCAAAAGGTCTTCATGAGCTGCAACCTCATCACCGGCATGTACCAGAGAC
TGGACAAAATGAGGAAAAACGCTTTCGCCTCCGTCATTCTGTTCGGCAAA
GGCTCGAACGAGCCGACTAATTGTCTTTAAACGCGCGATATAAGCGCACA
ATGCTCGAGAAACGATAAACTCTATCGCTCTGTCGCGTGCGTGGCATCTT
CGCGCGTTTGCCGAACAGAATGACGGAGGCGAAAGCGTTTTTCCTCATTT
TGTCCAGTCTCTGGTACATGCCGGTGATGAGGTTGCAGCTCATGAAGACC
TTTTGCGCGGAATTCCTTCAACGATTTACCTGACTTCAACCCGTGAATTT
TGATTGTCGTGTCGAACGAGGCGGTGAGGATTTGACTGTTGTCCCTTGAG
AATCGGAAGGAAGTTCTTCTCCGATGTGCTTTTCAATGACTTTCGGGTAG
ACTACGAGCCCTTCCAAAATGTTCATCAAAGTGATGAGGAGAGCATCCGA
GCAGAG SEQ ID NO: 66
Construct 1, sense mRNA
CTCTGCTCGGATGCTCTCCTCATCACTTTGATGAACATTTTGGAAGGGCT
CGTAGTCTACCCGAAAGTCATTGAAAAGCACATCGGAGAAGAACTTCCTT
CCGATTCTCAAGGGACAACAGTCAAATCCTCACCGCCTCGTTCGACACGA
CAATCAAAATTCACGGGTTGAAGTCAGGTAAATCGTTGAAGGAATTCCGC
GCAAAAGGTCTTCATGAGCTGCAACCTCATCACCGGCATGTACCAGAGAC
TGGACAAAATGAGGAAAAACGCTTTCGCCTCCGTCATTCTGTTCGGCAAA SEQ ID NO: 67
Construct 2, hpRNA
CGACCCGACTGTCATTCAACAGAGAAAGGGCGAATTGGAACCAGGCACCC
AAACTAGCATCCAAGTGATGGACAAATTGTGCAAGTACATTTACGACAAG
TGACATATTGGAGTTCAACCAGGTGGTCATTTTCGTCAAGTCTGTTCAAC
GGTGTATGGCTCTTGCTCAGCTCTTATGCGACCAAAACTTCCCGGCTGTC
AATCGCATGTACAGTTTACGAATAGAGTGTGGTCAGAAGTACCCGGAAGA
CGCTCCCTCGGCCCGATTTATACCTAGAATTAATATGACCTGCGTTAATA
GGCTCGAACGAGCCGACTAATTGTCTTTAAACGCGCGATATAAGCGCACA
ATGCTCGAGAAACGATAAACTCTATCGCTCTGTCGCGTGCGTGGCATCTT
CGCGCGTATTAACGCAGGTCATATTAATTCTAGGTATAAATCGGGCCGAG
GGAGCGTCTTCCGGGTACTTCTGACCACACTCTATTCGTAAACTGTACAT -continued
GCGATTGACAGCCGGGAAGTTTTGGTCGCATAAGAGCTGAGCAAGAGCCA
TACACCGTTGAACAGACTTGACGAAAATGACCACCTGGTTGAACTCCAAT
ATGTCACTTGTCGTAAATGTACTTGCACAATTTGTCCATCACTTGGATGC
TAGTTTGGGTGCCTGGTTCCAATTCGCCCTTTCTCTGTTGAATGACAGTC
GGGTCG SEQ ID NO: 68
Construct 2, sense mRNA
CGACCCGACTGTCATTCAACAGAGAAAGGGCGAATTGGAACCAGGCACCC
AAACTAGCATCCAAGTGATGGACAAATTGTGCAAGTACATTTACGACAAG
TGACATATTGGAGTTCAACCAGGTGGTCATTTTCGTCAAGTCTGTTCAAC
GGTGTATGGCTCTTGCTCAGCTCTTATGCGACCAAAACTTCCCGGCTGTC
AATCGCATGTACAGTTTACGAATAGAGTGTGGTCAGAAGTACCCGGAAGA
CGCTCCCTCGGCCCGATTTATACCTAGAATTAATATGACCTGCGTTAATA SEQ ID NO: 69
Construct 3, hpRNA
AAAAGCGACTGCAGCCAAAGTCAAAGACATAATCAAACGCCACCAGGGA
ACGGTGGTCGAAAACGAAGAACAGGCGACCCACATCCTTTACCCTATTGT
GGTTGACGGGCACAACGGGTCAATCAACGACATGCAGATGCACTGGGACG
GCACCATGTTTGTGACAGCTTCGAGTGACCACACAGCAAAGCTATTCGAC
AGATTTCGGTCGACTGTTTGGATTTTACGAAGAAGATCCTTCACACCGCT
TGGCATCCAACCGAGAACATTATTGCAGTGGCCGCCACCAACAATTTATT
TGGCTCGAACGAGCCGACTAATTGTCTTTAAACGCGCGATATAAGCGCAC
AATGCTCGAGAAACGATAAACTCTATCGCTCTGTCGCGTGCGTGGCATCT
TCGCGCGAAATAAATTGTTGGTGGCGGCCACTGCAATAATGTTCTCGGTT
GGATGCCAAGCGGTGTGAAGGATCTTCTTCGTAAAATCCAAACAGTCGAC
CGAAATCTGTCGAATAGCTTTGCTGTGTGGTCACTCGAAGCTGTCACAAA
CATGGTGCCGTCCCAGTGCATCTGCATGTCGTTGATTGACCCGTTGTGCC
CGTCAACCACAATAGGGTAAAGGATGTGGGTCGCCTGTTCTTCGTTTTCG
ACCACCGTTCCCTGGTGGCGTTTGATTATGTCTTTGACTTTGGCTGCAGT
CGCTTTT SEQ ID NO: 70
Construct 3, sense mRNA
AAAAGCGACTGCAGCCAAAGTCAAAGACATAATCAAACGCCACCAGGGA
ACGGTGGTCGAAAACGAAGAACAGGCGACCCACATCCTTTACCCTATTGT
GGTTGACGGGCACAACGGGTCAATCAACGACATGCAGATGCACTGGGACG
GCACCATGTTTGTGACAGCTTCGAGTGACCACACAGCAAAGCTATTCGAC
AGATTTCGGTCGACTGTTTGGATTTTACGAAGAAGATCCTTCACACCGCT
TGGCATCCAACCGAGAACATTATTGCAGTGGCCGCCACCAACAATTTATT
T SEQ ID NO: 71
GATTTCGGTCGACTGTTTGGATTTTACGAAGAAGATCCTTCACACCGCTT
GGCATCCAACCGAGAACATTATTGCAGTGGCCGCCACCAACAATTTATTT
GGCTCGAACGAGCCGACTAATTGTCTTTAAACGCGCGATATAAGCGCACA
ATGCTCGAGAAACGATAAACTCTATCGCTCTGTCGCGTGCGTGGCATCTT

```
CGCGCGAAATAAATTGTTGGTGGCGGCCACTGCAATAATGTTCTCGGTTG

GATGCCAAGCGGTGTGAAGGATCTTCTTCGTAAAATCCAAACAGTCGACC

GAAATC

SEQ ID NO: 72
GTTGACGGGCACAACGGGTCAATCAACGACATGCAGATGCACTGGGACGG

CACCATGTTTGTGACAGCTTCGAGTGACCACACAGCAAAGCTATTCGACA

GATTTCGGTCGACTGTTTGGATTTTACGAAGAAGATCCTTCACACCGCTT

GGCATCCAACCGAGAACATTATTGCAGTGGCCGCCACCAACAATTTATTT

GGCTCGAACGAGCCGACTAATTGTCTTTAAACGCGCGATATAAGCGCACA

ATGCTCGAGAAACGATAAACTCTATCGCTCTGTCGCGTGCGTGGCATCTT

CGCGCGAAATAAATTGTTGGTGGCGGCCACTGCAATAATGTTCTCGGTTG

GATGCCAAGCGGTGTGAAGGATCTTCTTCGTAAAATCCAAACAGTCGACC

GAAATCTGTCGAATAGCTTTGCTGTGTGGTCACTCGAAGCTGTCACAAAC

ATGGTGCCGTCCCAGTGCATCTGCATGTCGTTGATTGACCCGTTGTGCCC

GTCAAC

SEQ ID NO: 73
GTTGACGGGCACAACGGGTCAATCAACGACATGCAGATGCACTGGGACGG

CACCATGTTTGTGACAGCTTCGAGTGACCACACAGCAAAGCTATTCGACA

GATTTCGGTCGACTGTTTGGATTTTACGAAGAAGATCCTTCACACCGCTT

GGCATCCAACCGAGAACATTATTGCAGTGGCCGCCACCAACAATTTATTT

SEQ ID NO: 74
Gene #57
Vps23
NADH-ubiquinone oxidoreductase,
20 Kd subunit (partial)
GCCCAAGACAAAATCGAACCTGTAAAGAGGAAACCGTATTCACCATTTCC

TAAGGGTAACAACGCTGCTGAGTTCGCAATGGCTCGTCTGGACGATTTAA

TCAATTGGGCGAGAAAGGGGTCACTATGGCCTCTGACATTCGGACTGGCT

TGCTGCGCTGTAGAAATGATGCACTTCGCTGCTCCGCGCTACGACATGGA

TCGTTACGGAGTAGTATTCAGGGCGTCTCCACGACAGGCTGATGTCATCA

TCGTCGCTGGTACTTTGACTAATAAAATGGCCCCTGCCTTGAGAAAAGTT

TATGATCAGATGCCGGAGCCGAGGTGGGTATATCCATGGGGAGCTGTGC

TAACGGAGGTGGATACTACCATTACTCCTACTCCGTCGTCAGAGGCTGTG

ATAGAATTGTACCTGTGGATATATACGTTCCAGGTTGTCCACCCACCGCT

GAGGCTCTCCTCTATGGGGTTCTTCAACTTCAGAAGAAAATTAAAAGAAG

TAACCAGATGCAGATGTGGTACAGGAAGTAA

SEQ ID NO: 75
Gene #57
Nucleotides 19-118 of SEQ ID NO: 74
Vps23
NADH-ubiquinone oxidoreductase,
20 Kd subunit
CCTGTAAAGAGGAAACCGTATTCACCATTTCCTAAGGGTAACAACGCTGC

TGAGTTCGCAATGGCTCGTCTGGACGATTTAATCAATTGGGCGAGAAAGG

SEQ ID NO: 76
Gene #58
Vps28
Vacuolar protein sorting 28 (partial)
CTCGTTGATGAAGTGAAGCTTTTCAGAAATGCAAGGGAAAGAGAAAGGTA

CGATAACATGGCAGACTTATTCGCTGTCATAAATACGCTTCAGAACCTGG

AAAAAGCTTACATTCGAGACTGCGTGACGGCTAAAGAGTACACAGCCGCC

TGCTCCAAACTCCTCGTCCAGTACAAAGCCGCTTTTAAGCAAGTTCAAAA

TGACGAGTACCCGACCATCGAAGCCTTCGTCGCTAAATACAAATTGGACT

GTCCTGCGGCGATGGAGAGGATTAAAGAAGATCGACCCATTACTATCAAA

GATGACAAAGGGAACACGAGTAAATGCATTGCGGACATCGTTTCGCTGTT

TATCACTTTAATGGATAAACTCAGACTGGAAATGAAAGCGGTTGATGAAC

TACATCCAGATTTGAGGGATTTGACCGACACAATGAACCGACTCAGCATC

CTTCCTTCGGACTTTGAAGGGAAGAAAAAAGTCACTGAATGGCTTGGAAC

ACTCGACTCGATGTCAGCCTCTGACGAGCTGACTGAGCAACAAGTCCGTC

AATTAATATTTGATTTGGAATCGTCATACAACGCTTTCAACAAGCTCTTG

CACAATACATAA

SEQ ID NO: 77
Gene #58
Nucleotides 160-259 of SEQ ID NO: 76
Vps28
Vacuolar protein sorting 28
CTCCTCGTCCAGTACAAAGCCGCTTTTAAGCAAGTTCAAAATGACGAGTA

CCCGACCATCGAAGCCTTCGTCGCTAAATACAAATTGGACTGTCCTGCGG

SEQ ID NO: 78
Gene #59
Vps22/Isn (Partial)
Regulation of Notch signaling pathway
GGGCGACTTCTACTTTGAACTGAGCATACAAATTGTTGAAGTTTGTCTGGC

GACGAACGAGAAAAACGGAGGTATCATCGGGTTGAACGAGCTCCGTTTGA

AACTACTAAAGTCGAGGGGTCGCCACGCCCAAGAGGTGACCCAGGAGGAC

ATCCTTTGCGCCGCCAAGAAACTCAGTGTGTTTGGAAATGGA

SEQ ID NO: 79
Gene #59
Nucleotides 46-145 of SEQ ID NO: 78
Vps22/Isn
Regulation of Notch signaling pathway
CTGGCGACGAACGAGAAAAACGGAGGTATCATCGGGTTGAACGAGCTCCG

TTTGAAACTACTAAAGTCGAGGGGTCGCCACGCCCAAGAGGTGACCCAGG

SEQ ID NO: 80
Gene #60
Vps2 (partial)
Protein transport
AAACGGGTCACCCCTGAGGAACAGCTGAGGAAGAATCAAAGAGCCCTGA

ACAGAGCGACGAGAGAACTTGACAGGGAAAAAGCGCGCATGGAAGCGCA

AGAGAAGAAAACGATCGCAGACATTAAGAAAATGGCTAAACATGGTCAAA

TGGATTCTGTCACAGTAATGGCCCAAGATCTTGTCCGGACGAGAAGGTAC

CTAAAAAAATTCATGTTGATGAAAGCCAACATCCAAGCGGTTTCACTCAA

GATTCAAAGTCTGCGTTCGCAAAACGCGATGGGAGAAGCGATGAGGGGTG

TGTGCATAGCCATACGAAACATGAACAGACAACTAAACATACCTCGACTC

CAAAGGATACTCCGGGAGTTTGAAAAACAGTCGGATATAATGGATATGAA
```

AGAGGCAATATCAAATGATGCAATTGATGGGGCGATGGAAGATGACGGGG

ATGAAGAGGAAAGTGATGCTGTAGTTTCGCAAGTGTTGGACGAGCTGGGT

CTCCAATTGGCTGACCAA

SEQ ID NO: 81
Gene #60
Nucleotides 218-317 of SEQ ID NO: 80
Vps2
Protein transport
TGAAAGCCAACATCCAAGCGGTTTCACTCAAGATTCAAAGTCTGCGTTCG

CAAAACGCGATGGGAGAAGCGATGAGGGGTGTGTGCATAGCCATACGAAA

SEQ ID NO: 82
Gene #61
Snf7/shrub (partial)
ESCRT-III pathway
ATACAGAAACTGAGGGAGATCGAGGACATGCTCATCAAAAAACAAGAACA

CTTAGAAAGGCAAATCGAGCGAGAATTAGAAGTGGCTAAAAAAAATGGAA

TGGCCAACAAGCGGGTTTCCCTTCAAGCGTTGAAGAAAAAACGGCGGTAT

GAGAAACAATTGCAGCAAATTGACGGGACTCTTAGCACGATTGAAATGCA

AAGGGAGGCTTTGGAGTCGGCCAGCACAAACACCGCTGTCTTCCAAACCA

TGAAAATGGCAGCGAACTCTTTGAAAACAGCACATTTAAACATGGACGTC

GACCATGTTCACGACATCATGGATGACATCGCTGAACAGCAAGAACTGGC

CAAGGAAATAGCCGACGCTATAACCCAACCTTTAGGTTTCAGCGCAGACG

TG

SEQ ID NO: 83
Gene #61
Nucleotides 210-309 of SEQ ID NO: 80
Snf7/shrub (partial)
ESCRT-III pathway
TTTGGAGTCGGCCAGCACAAACACCGCTGTCTTCCAAACCATGAAAATGG

CAGCGAACTCTTTGAAAACAGCACATTTAAACATGGACGTCGACCATGTT

SEQ ID NO: 87
Gene #34
hay
DNA excision repair protein
haywire-like (partial)
TATATTTACGGTCCAACTTCTCAGAACGAAAGGATCCAAATTCTACAAAA

TTTCAAATTCAATCCCAAAGTAAATACGATTTTTGTGAGTAAAGTTGCCG

ATACGTCGTTTGATCTTCCCGAGGCTAATGTACTGATTCAAATATCCTCT

CATGGAGGCTCTCGACGTCAAGAAGCTCAGAGATTGGGTAAAAATTCTCA

GAGCCAAAAAAGGGAGCGATCGCTGAAGAGTATAATGCGTTTTTTCCTA

CACACTCGTTTCCCAAGACACGATGGAAATGGCGTATTCGCGGAAGCGCC

AAGCGGTTCCTCGTCAATCAGGGCTACAGTTACAAAGTGGTGACGAAATT

GGCTGGTATCGACCAAGATCCTGACATAATGTACAAAACCCGAGACGAG

---

What is claimed is:

1. A vector comprising an expression control sequence operably linked to a nucleotide sequence that is a template for both strands of a double stranded ribonucleic acid molecule (dsRNA) comprising a unit of a first strand of nucleotides that is at least 90% identical to at least 23 contiguous nucleotides in SEQ ID NO 33 and a second strand of nucleotides that is the complement of said first strand of nucleotides, wherein expression of said dsRNA inhibits growth of Bronze bug.

2. The vector of claim 1 wherein said first and second strands of nucleotides are at least about 25, 35, 50, 70, 100, 150, 200, 250, 300, 400, 500, 600, 700, 900, 1100, 1300, or 1500 nucleotides in length.

3. The vector of claim 1 wherein said first and second strands of nucleotides are at least 95% identical to SEQ ID NO 33.

4. The vector of claim 1 wherein the sequences of said first and second strands of nucleotides are less than about 80% identical to the sequence of the honey bee ortholog of said first and second strands of nucleotides.

5. The vector of claim 1 comprising at least two of said units.

6. The vector of claim 1 further comprising a loop region separating said first and second strands of nucleotides.

7. A host cell comprising the expression vector of claim 1.

8. The host cell of claim 7 wherein said host is a bacterial cell or a yeast cell.

9. The host cell of claim 8 wherein said host is an *Agrobacterium*.

10. A plant tissue transformed with the host cell of claim 9.

11. A plant tissue comprising the vector of claim 1.

12. A method of producing a pest resistant plant comprising expressing the vector of claim 1 in said plant.

13. The method of claim 12, wherein said plant is *Eucalyptus*.

14. The method of claim 12 wherein said pest is Bronze bug.

15. A method of inhibiting a pest infestation comprising cultivating a plant comprising the vector of claim 1.

16. The method of claim 15 wherein said plant is *Eucalyptus*.

17. The method of claim 16 wherein said pest is Bronze bug.

18. A method of producing a plant resistant to a plant pathogenic pest comprising:
    (a) transforming a plant cell with the vector of claim 1;
    (b) regenerating a plant from the transformed plant cell; and
    (c) growing the transformed plant cell under conditions suitable for the transcription of said recombinant DNA construct,
    said grown transformed plant thus being resistant to said pest compared to an untransformed plant.

19. The method of claim 18 further comprising transforming said plant cell with a recombinant DNA construct that expresses a single stranded RNA that is complementary to any one strand of said dsRNA or a fragment thereof.

20. The method of claim 18 wherein said plant is *Eucalyptus*.

21. The method of claim 20 wherein said pest is Bronze bug.

22. A vector comprising an expression control sequence operably linked to a nucleotide sequence that is a template for both strands of a double stranded ribonucleic acid molecule (dsRNA) comprising a unit of a first strand of nucleotides that is at least 90% identical to at least 23 contiguous nucleotides in SEQ ID NO 34 and a second strand of nucleotides that is the complement of said first strand of nucleotides, wherein expression of said dsRNA inhibits growth of Bronze bug.

23. The plant tissue of claim 11 wherein said tissue is selected from the group consisting of leaf tissue, veins, petioles, small branches, branches, flowers, trunk, fruit and seeds.

* * * * *

SEQUENCE LISTING

<160> NUMBER OF SEQ ID NOS: 87

<210> SEQ ID NO 1
<211> LENGTH: 846
<212> TYPE: DNA
<213> ORGANISM: Thaumastocoris peregrinus

<400> SEQUENCE: 1

```
gatgtcgtca acccttggtc cgtttcaagt tcctcgcagg aagggattga ctacgataaa      60
ctcataaaga agtttggcag ctccaaaatc gaccgagagc tgctcgaccg gtgggaaaaa     120
gccactggaa aaccagccca ccatctactc cgtcgaggga ttttcttcag tcatcgcgac     180
gtccatacaa tattgaattt ggtggaacaa gggaaaaagt tctatttgta caccggccga     240
gggccgtcct ccgcttcaat gcatgtcgga catttggtcc cgttcgtttt tacaaagtgg     300
attcaagaaa tgttcaacgt tcctctcgtc attcaattga ccgacgacga aaagtttctc     360
tggaaagacc tatctgtgga agaggcgaac aagatggcct gggaaaacgc taaagacatt     420
atcgcctgtg gcttcgacgt caataaaacg tttatcttct ctgatttgga ctacatgggg     480
cagtgctcgg aattctacaa gaatgtggtc cggattcaaa agtgcgtcac tttcaatcaa     540
gttaaaggca ttttcggatt cggagacagt gacgtcattg ggaaaattag ttttccggcc     600
attcaagccg cacccagcct ttccacgtcg tttccattca ttttcggaaa ggagaaaatt     660
ccctgtttga taccttgtgc cattgatcag gatccttatt ttcgaatgac gagagacgtt     720
gcgccgcgtc tgggcttccc taaaccagcc ctgctccact ccacttttat tccagctctg     780
caaggagctc aaacgaaaat gtcgggcagc gacgccaaca ccgctatttt cctcacggat     840
actccg                                                               846
```

<210> SEQ ID NO 2

```
<211> LENGTH: 100
<212> TYPE: DNA
<213> ORGANISM: Thaumastocoris peregrinus

<400> SEQUENCE: 2
ccgagagctg ctcgaccggt gggaaaaagc cactggaaaa ccagcccacc atctactccg      60
tcgagggatt ttcttcagtc atcgcgacgt ccatacaata                           100

<210> SEQ ID NO 3
<211> LENGTH: 234
<212> TYPE: DNA
<213> ORGANISM: Thaumastocoris peregrinus

<400> SEQUENCE: 3
gccatcgtcg atgttcccgt cggtgacgac attcttggcc gagttgtcga cgcccttgga      60
aaccctatcg atggcaaggg ccctctttct ggtaaataga ggatgcgagt tggtgtcaaa     120
gccccgggta tcatccccag gatctcggtc cgcgagccta tgcaaaccgg aatcaaagcc     180
gttgactcgc ttgtacccat cggtcgagga caacgggagc tcatcattgg agag           234

<210> SEQ ID NO 4
<211> LENGTH: 100
<212> TYPE: DNA
<213> ORGANISM: Thaumastocoris peregrinus

<400> SEQUENCE: 4
gacagaaaag atccactgtc gcgcaaattg tgaaaagatt gaccgacacc ggggccatga      60
aatacaccat cattgtcgct gcgactgcat ctgacgccgc                           100

<210> SEQ ID NO 5
<211> LENGTH: 717
<212> TYPE: DNA
<213> ORGANISM: Thaumastocoris peregrinus

<400> SEQUENCE: 5
gaaagggact tctccgaaac tcaagtcctc gttaaaatta ttgttgagta cgatcaaatg      60
ctgcagaaga atcacgcgtt gttgaatcga gtggaaaatg cgacgaacga agacgaaagg     120
gttcaattga ggaaggtgtc gagcaagcag cacatggccg caacagtact tccgatccgg     180
agtgtaggag ttcagggaga ctgtcgcagc tacagctacg tcgttgggat atcaagcgag     240
aaagacccgg attgggatga cctcgtcatc ctctcgcagc ttattccccg tgtgtgccac     300
aacgtcaacc gagtctgcta cattgctggc ggcctcgtca agaccctgt tcaggacatc      360 actccgactt ttctcacttc tccagttctg gcgacgatac gacaagcaga ccatttggcg     420
actcaggtcc tctataatag cgattacatg tctaaaatat cgcaaatgcc cgtgatcctc     480
cttccactgc attttgaccg ggacgccgct ctccgagtcc catcgtgtca acggtccgtt     540
gttctccgcc catttatcac gcacgatttc atgacgggaa tcccagccat cccgggatcc     600
acatacccat tgacatcgtt caaaaaaatg ttctctgaaa tctccttaat gccgggaatc     660
tctcgtgtcc tgtacgacct gacagccaaa ccacccggaa caactgaatg ggagtga       717

<210> SEQ ID NO 6
<211> LENGTH: 100
<212> TYPE: DNA
<213> ORGANISM: Thaumastocoris peregrinus

<400> SEQUENCE: 6
cttttctcac ttctccagtt ctggcgacga tacgacaagc agaccatttg gcgactcagg      60
```

<210> SEQ ID NO 7
<211> LENGTH: 753
<212> TYPE: DNA
<213> ORGANISM: Thaumastocoris peregrinus

<400> SEQUENCE: 7

```
atgggaactg cgaggtacga ccgggccatc accgttttct cgcctgatgg gcacctcctc    60
caagtcgaat acgcccaaga ggccgtccga aaaggatcaa ctgccgtggg agtccgaggg   120
gaagactgcg tcgttctcgg agttgaaaag aaatcagtgg cgaaactcca agaggaaaga   180
acagtgagga aagtgtgtct tttagacgat cacattctca tcgcgtttgc cggtctgact   240
gcggatgctc gaatattaat taatcgggcg caaatagagt gtcaatcgca caagttgact   300
gtagaggacc cggtgacggt tgagtacatc acacgttaca tagcagggct aaacagaaa    360
tacacgcaga gcaatggccg cgaccgtttt ggcatttcgt gccttattgg tggttttgat   420
ttggacgggt cacctcatct gttccaaacg gaaccttctg gaatattcta cgagtggaaa   480
gccaatgcca caggtcgcgg tgccaagtca gttaaggagt tccttgaaaa gaattacgaa   540
acttccgact tgaagactga agacggtgtc atcaagttgg cagttcgggc tctgctagaa   600
gtcgtgcagt ccggccggaa gaatttggaa gtcgctgtga tgcgccggaa tcagccttttg  660
agaatgctgg atctggattc gatcgatcaa attgtgactc aagttgaaca agaaaaagag   720
gaggaagctg aaaagaagaa gcagaagaaa taa                                753
```

<210> SEQ ID NO 8
<211> LENGTH: 100
<212> TYPE: DNA
<213> ORGANISM: Thaumastocoris peregrinus

<400> SEQUENCE: 8

```
cggtgccaag tcagttaagg agttccttga aaagaattac gaaacttccg acttgaagac    60
tgaagacggt gtcatcaagt tggcagttcg ggctctgcta                         100
```

<210> SEQ ID NO 9
<211> LENGTH: 777
<212> TYPE: DNA
<213> ORGANISM: Thaumastocoris peregrinus

<400> SEQUENCE: 9

```
atggcccgcc gttatgactc gagaacgaca atattttcgc cggaaggtcg actgtaccaa    60
gttgagtatg cgatggaggc gataagtcat gccggtacgt gtttgggcat cctggccaac   120
gacggtatca ttctcgtcgc tgaaaaagaa accccaaca agctcttgga tgagtccgtg    180
tactcggaaa aaattttcaa gcttaacgaa acatgatat gcagtttagc cgggatcact    240
tccgatgcga acgtcctcac aaacgagctc cgtgtcatct cccaacgcta tttgatccag   300
tacggtgaaa cgatcccctg tgagcagctc gtctcgtggc tttgtgacat taaacaagcg   360
tacactcaat acggtggtaa gaggcctttc ggtgtttccg tcctgtacat gggctgggac   420
aaacactacg gctaccaact ctatcaatcc gatccgagcg taactactc cggatggaaa    480
gccacctgta tcgggcaaaa cagtggagca gccgtttcca gccttaaaac cgactataaa   540
gaaggtgaaa tgaccgttca agacgctcta gctctcggaa tcaaagtctt aagcaaaact   600
ttagacactg ccaaattaac aactgatcgc gtggaagttg caacgcttca gcgcatcgat   660
```

```
ggcaaatgca tcactcggat tttgcccgct agtgaagttc aagtactcat tgacgcattt    720
gaaaagtctg aggctgaagc cgccgctcaa aggagagaaa gagctccgaa tccttaa      777
```

<210> SEQ ID NO 10
<211> LENGTH: 100
<212> TYPE: DNA
<213> ORGANISM: Thaumastocoris peregrinus

<400> SEQUENCE: 10

```
actcggattt tgcccgctag tgaagttcaa gtactcattg acgcatttga aaagtctgag    60
gctgaagccg ccgctcaaag gagagaaaga gctccgaatc                         100
```

<210> SEQ ID NO 11
<211> LENGTH: 372
<212> TYPE: DNA
<213> ORGANISM: Thaumastocoris peregrinus

<400> SEQUENCE: 11

```
accgctggag gtcagacttg gaagacaac acgctcgccg aatgggaaga tgatgatttc     60 cggcttttt gtggagattt aggaaacgat gtcaccgacg aagtcttaac ccgagcgttt    120
tccaagtatc cgtcatttct caaagctcga gtcgttcgcg acaaaagaac aaataaaact   180
aaaggatttg gtttcgtcag tttcaaagat ccaaacgatt tcatacgagc aactaaagaa   240
atgaatggcc gctacgtcgg gtcacgtccc attaaattaa ggaaaagctc atggaaaaac   300
agaactttgg atgtcgtcag aaagaaggat aagaaaaag cagctctcat tagtatgctc    360
acagggaaat ga                                                       372
```

<210> SEQ ID NO 12
<211> LENGTH: 100
<212> TYPE: DNA
<213> ORGANISM: Thaumastocoris peregrinus

<400> SEQUENCE: 12

```
ttaaattaag gaaaagctca tggaaaaaca gaactttgga tgtcgtcaga agaaggata     60 aagaaaaagc agctctcatt agtatgctca cagggaaatg                         100
```

<210> SEQ ID NO 13
<211> LENGTH: 750
<212> TYPE: DNA
<213> ORGANISM: Thaumastocoris peregrinus

<400> SEQUENCE: 13

```
gaaatgtatg agttggcctg tcgtgggctc ctgtcaccgc caccgtcgct tgctcaact     60 gaagtgccgc tacgttacca aatctccttt tacaatttgg ctccattgaa agaagaagaa   120
gcatatctga aaccgaaaat catactttac cgggaagtga tgtatcactc ggaaattgaa   180
atcatcaaac aaatggctca tcccaggttg aaacgagcga cagtccaaaa ttacaaaact   240
ggagagttgg aaatcgcctc atatcgaata tcaaaatccg cgtggttcaa tgacaacgac   300
cacgaggtga tggcgcggtt gacgaggaga gtcgaggaca tgacgggctt aacaatgaaa   360
tctgccgaag acctccaagt cgtcaattac ggcattggag ccactatga gccacattac    420 gattttgcca gaaaaggaga agaaacacat gcgttcaagt ctctcggaac tgggaacaga   480
atcgctacag tattgttcta tatgagcgac gtcgctcaag gaggtgccac cgtgttcccc   540
cagctaaatc tgtctctttg gccggaaaaa ggaactgctg cgttttggat gaatcttctc   600
gccaatggtg aaggtgatta cgacacgagg catgcagcat gtcctgtact agcaggcacg   660
```

```
aaatgggtgt ctaaccggtg gatccacgaa agagaacaag agttcaggag accctgttcg    720
ctggatccca acgagtgaat tattcccaca                                     750
```

<210> SEQ ID NO 14
<211> LENGTH: 100
<212> TYPE: DNA
<213> ORGANISM: Thaumastocoris peregrinus

<400> SEQUENCE: 14

```
ggagagttgg aaatcgcctc atatcgaata tcaaaatccg cgtggttcaa tgacaacgac     60
cacgaggtga tggcgcggtt gacgaggaga gtcgaggaca                          100
```

<210> SEQ ID NO 15
<211> LENGTH: 495
<212> TYPE: DNA
<213> ORGANISM: Thaumastocoris peregrinus

<400> SEQUENCE: 15

```
ctctgcacag acctcaggct ccttgacaaa tatgaaagag attgaagagc ctttcgaaaa     60
actcaaattg ggtcaagcgc tatggcgtac aaaaggaatc caatgagaag tgaaaggtgt   120
tgcgctttgg cccgtcactt ggtctctttg cactcgaatg cggccaacac tgctgccgtc   180
caatggctcg aaagaaccct agatgacagc gccaatcgac gcatcaccct agccgaagcg   240
tttctctgct cggatgctct cctcatcact ttgatgaaca ttttggaagg gctcgtagtc   300
tacccgaaag tcattgaaaa gcacatcgga gaagaacttc cttttatggc aactgagaac   360
atcattatgg ccatggtcaa agctggcgaa gacagacaag aatgccatga gaaaatccga   420
gtttgggccc aagaagcggg cactcaagtc aaaattttgg ccttaaaaa cgatctagtg   480 gaccgaatca aaaag                                                   495
```

<210> SEQ ID NO 16
<211> LENGTH: 100
<212> TYPE: DNA
<213> ORGANISM: Thaumastocoris peregrinus

<400> SEQUENCE: 16

```
ctctgctcgg atgctctcct catcactttg atgaacattt tggaagggct cgtagtctac     60
ccgaaagtca ttgaaaagca catcggagaa gaacttcctt                          100
```

<210> SEQ ID NO 17
<211> LENGTH: 537
<212> TYPE: DNA
<213> ORGANISM: Thaumastocoris peregrinus

<400> SEQUENCE: 17

```
caagcattga agtggcaaca gcaccagggg cttcttccac caggtacgac atcgcttgtc     60
cgtggtaaag ctgcgataag agaccaagac gatgaaaagt acccaacgca gttgtcaaag   120
cagatcaagt tcggtcacaa gtcccatgtc gaatgtgcca cttttcgcc ggacgggcaa    180 ttcctcgtgt ctgggagcgt tgacggtttc attgaagtgt ggaatttcac gacggggaaa   240
atccgaaagg atctcaagta ccaaggccag gacaatttca tgatgatgga agaagccgtt   300
ttggcgctag ctttcagccg cgactcagaa atgcttgcga gcggttccca agagggtaaa   360
atcaaagtgt ggaaaatcgt gacgggtcag tgtctccgca agtatgaaaa agcccattcc   420
aaaggcgtta cttgcatccg attctcaagg gacaacagtc aaatcctcac cgcctcgttc   480
```
gacacgacaa tcaaaattca cgggttgaag tcaggtaaat cgttgaagga attccgc       537

<210> SEQ ID NO 18
<211> LENGTH: 100
<212> TYPE: DNA
<213> ORGANISM: Thaumastocoris peregrinus

<400> SEQUENCE: 18
ccgattctca agggacaaca gtcaaatcct caccgcctcg ttcgacacga caatcaaaat       60 tcacggggttg aagtcaggta aatcgttgaa ggaattccgc       100

<210> SEQ ID NO 19
<211> LENGTH: 1185
<212> TYPE: DNA
<213> ORGANISM: Thaumastocoris peregrinus

<400> SEQUENCE: 19
caacggctac tgtcatcttt cctttcgaaa ttgttcactc cgcgaagctt tgagtcggat       60
tttgcattgg ttgccaacgt tgacggtgcc aacggcaca ttgtgatgcc ggacggaaca       120
aggagggatc acttcctccg gtggatcgaa gggttgtccg atcgccagac acccgcgtgg       180
ctcggtcttc caaacaacgc cgagaaagtc ctattgacca atcgaggagc cgatttggtc       240
atgaaactgc tcaaaatgca acaattagag gacgaagacg agctcgccta caccgaagaa       300
gccgccgcca acaatccaga cggcccttcg tccgctctcc ctgaagacgc tagaccagcc       360
tggatgcgca cttttgtacaa ttccgcagtt tcctggctcg aactcctccc cacaagcctt       420
ccgactctga agagaactgt ggaaaatatc aaagatcctc tctaccggta cttcgaaagg       480
gaggtgaacg ccatcgccaa actcttacgt gatgttgtcc acgatttaac tgacatagtc       540
gcgatttgtc aaggtacgaa aaacaaaca aattaccata gaactatggt tggggagttg       600
gttcgaggaa tgctcccggc atcttggcgg cgctacacag ttccccgcgg ctgcacagta       660
atccaatggg tcaccgactt cagtaacaga gtcaagcaat ggcccacat atcccaatta       720 gcctctcaga gaggtccttc agaaataaag agtgtcgctg tatggctggg cggtctcacc       780
aaccccgagg cttacgttac tgctacgcgt cagtgcattg cacaagctaa cagttggtct       840
ttggaggagc ttgtgctcga cgttacgatt ttggacagtt cgggacaagt tcctatcgac       900
ggctccagtt tccctgtgac tgggctgaag cttcaaggag ctcaatgtaa aaacaaccaa       960
ttgcagctcg cctcgactat catgatggaa ctacccacaa ctcttcttcg ctggaccaga      1020
atcggtgact gcaccagcga cggcaagctt tcccttcccg tttatttgaa ttcaacccga      1080
agtgaacttc tgttcacggt cgacctcaac gttcttccgg gccaagatcc gcacagtttc      1140
tacgaaagag gagtcgcttt gcttgcttca actgccctta attaa       1185

<210> SEQ ID NO 20
<211> LENGTH: 100
<212> TYPE: DNA
<213> ORGANISM: Thaumastocoris peregrinus

<400> SEQUENCE: 20
tcgaagggtt gtccgatcgc cagacacccg cgtggctcgg tcttccaaac aacgccgaga       60
aagtcctatt gaccaatcga ggagccgatt tggtcatgaa       100

<210> SEQ ID NO 21
<211> LENGTH: 312
<212> TYPE: DNA
<213> ORGANISM: Thaumastocoris peregrinus

<400> SEQUENCE: 21

```
atgtcgcaca cgataatgct catccagccg ggtaccaaac ctgagacgag aacctactca    60
gactacgaat ctgtgaacga gtgtatggaa ggtgtgtgca aaatatatga ggagcacttg   120
aaaaggcaga acccgaacac tcccgctatc acttacgaca ttagtcaatt gtttgacttc   180
attgaccagt tgtgcgattt gtcctgccta gtgtaccaga aaggctccaa cacttacgcc   240
ccctacaaca aagactggat caaagagaag atctacattc tgctccgacg gcaggccaat   300
aatcgccaat aa                                                      312
```

<210> SEQ ID NO 22
<211> LENGTH: 100
<212> TYPE: DNA
<213> ORGANISM: Thaumastocoris peregrinus

<400> SEQUENCE: 22

```
ttcattgacc agttgtgcga tttgtcctgc ctagtgtacc agaaaggctc caacacttac    60
gcccctaca acaaagactg gatcaaagag aagatctaca                         100
```

<210> SEQ ID NO 23
<211> LENGTH: 147
<212> TYPE: DNA
<213> ORGANISM: Thaumastocoris peregrinus

<400> SEQUENCE: 23

```
gcccttgacg tcgactggca acgaacacg agttttgcct cgtgcagtac cgaccagtgt     60
atccacgttt gcaaattaaa tgttgaaaaa cccatcaagt ccttccaagg gcacacaaat   120
gaagtcaacg cgattaagtg ggatccg                                      147
```

<210> SEQ ID NO 24
<211> LENGTH: 100
<212> TYPE: DNA
<213> ORGANISM: Thaumastocoris peregrinus

<400> SEQUENCE: 24

```
tactgttcgt ctctgggaag tggatcgggg agcttgtatt cacactttaa ctaaacacac    60
tgagcccgtg tacagcgtcg ccttttcccc cgacggtaaa                         100
```

<210> SEQ ID NO 25
<211> LENGTH: 714
<212> TYPE: DNA
<213> ORGANISM: Thaumastocoris peregrinus

<400> SEQUENCE: 25

```
atcaagcccg tcagtcccga acaagaagag ctcatacacc gtctcgtata tttccaaagc    60
gagtacgaac atccgtgtga agaggacgtc cgccgaataa atgctccaaa cgacgacgat   120
gagcccaact cagactacag gttccgatac ttggccgaaa tctccatact aactgttcaa   180
cttattgttg aatttgcaaa aagacttcct ggattcgaca aacttttgag ggaagaccaa   240
atcactttac ttaaggcatg ttcaagcgaa gtgatgatgt tgaggatggc tcggcggtac   300
gacgcacaga ccgactcgat cctcttcgcg aacaaccaac cctataccag agactcgtat   360
aatttagcag gcatgggaga aatagtcgag gatctgctca ggttttgccg gcaaatgtac   420
aatatgaaag tggacaacgc tgagtacgca cttctcaccg ccatcgttat attctcagag   480
agaccgtcac ttattgaagg gtggaaagtg gaaaaaatcc aggaaatcta tttggagggg   540
```

```
ctcaaatcct acgtggacaa caggtcgagg cctcgatccc ctacaatatt cgccaaactc    600
ctctcggtcc tgactgagct tcgaacactc ggaaatcaaa atacgagat gtgtttctca    660 ttaaaacttc aaaataagaa acttcctccg tttttgtcag aaatatggga cgta         714
```

<210> SEQ ID NO 26
<211> LENGTH: 100
<212> TYPE: DNA
<213> ORGANISM: Thaumastocoris peregrinus

<400> SEQUENCE: 26

```
acgaacatcc gtgtgaagag gacgtccgcc gaataaatgc tccaaacgac gacgatgagc    60
ccaactcaga ctacaggttc cgatacttgg ccgaaatctc                         100
```

<210> SEQ ID NO 27
<211> LENGTH: 1329
<212> TYPE: DNA
<213> ORGANISM: Thaumastocoris peregrinus

<400> SEQUENCE: 27

```
atcgtcgtca tcggccacgt cgactctggt aaatcgacga ccaccgggca tttgatctac    60
aaatgcggtg gtattgacaa acgtaccatt gagaagttcg agaaggaagc ccaagaaatg    120
ggaaaaggtt ccttcaagta cgcttgggtt ttggacaagc tgaaagccga acgtgagcgt    180
ggtatcacaa ttgacattgc gctctggaag ttcgaaactg ccaagtacta cgttaccatc    240
attgatgccc ccggtcacag ggatttcatc aagaacatga tcaccggaac gtctcaggct    300
gattgtgctg ttttgatcgt tgctgctggt actggtgaat cgaggcggg tatttccaag    360 aacggacaaa cccgtgagca cgctctcctc gctttcactc tcggtgtgaa acagctcatt    420
gtcggagtga acaaaatgga ctcgactgag cccccgtaca gcgagagccg ttacgaggaa    480
atcaagaaag aggtgtcttc gtacatcaag aaaatcgggt acaacccagc ggctgtcgct    540
ttcgttccca tctccggatg gcacggtgac aacatgttgg aggcgtccga caaaatgccc    600
tggttcaagg gatggaacgt tgagaggaaa gagggtaagg ccgacggaaa gtgccttatt    660
gaagccctcg acgccatcct cccccgtcc cgtcccaccg acaaggccct tcgacttccc    720
cttcaggacg tgtacaaaat cggtggtatc ggaacagtgc ccgtcggccg agtcgaaacc    780
ggtctactga aacctggtat gatcgttact tttgccctg tcaacctcac gactgaggtt    840
aaatccgtgg agatgcacca cgaagccctc caagaggctg tgcccggaga caacgtcgga    900
ttcaacgtta agaacgtctc cgttaaagag ttgcgtcgtg gtttcgtcgc cggcgactcc    960
aaaaacgctc ctcccaaggc cgcgagtgac ttcactgccc aagtcatcgt tctcaaccat    1020
cccggtcaaa tcgccaacgg gtacactccc gtcttggatt gtcacactgc ccacatcgcg    1080
tgtaaattca acgagatcaa agaaaaatgt gacagacgta ctggtaaaac cactgagcag    1140
aaccccaagt tcatcaagtc tggtgacgcc gctattgtca ccctcatccc gactaagccc    1200
atgtgcgtcg agtctttcca ggagttccct ccctgggac gtttcgccgt gcgtgacatg    1260
aggcaaaccg tcgctgtcgg cgtcattaaa agcgtcacta ataagacgt gacgactggt    1320 aaagtgacg                                                          1329
```

<210> SEQ ID NO 28
<211> LENGTH: 100
<212> TYPE: DNA
<213> ORGANISM: Thaumastocoris peregrinus

<400> SEQUENCE: 28
tcgtcgccgg cgactccaaa aacgctcctc ccaaggccgc gagtgacttc actgcccaag    60
tcatcgttct caaccatccc ggtcaaatcg ccaacgggta                          100

<210> SEQ ID NO 29
<211> LENGTH: 1266
<212> TYPE: DNA
<213> ORGANISM: Thaumastocoris peregrinus

<400> SEQUENCE: 29
atggcgtcag gaactttgta cacttactcg ggaaatttcc gcgcgtacaa agccctcatt    60
gcggccgaat acgggggcgg ttcggtcaaa gtggcaccgg attttgtctt cggcgaaacg   120
aacaggactc ctaattttct caagaaattc cccctgggaa aggtgcctgc tttcgaaagt   180
accgacggca catgtgtcac cgaaagcaac gccatagcct ggttcgttgc cagtccagaa   240
ttgagaggga agtctgacgc ggaaaaagct caaattgttc aatggttgag ctactcagac   300
tccgaagttc ttcaagccac ttgtacttgg gtcttcccct acctcggtat ccttcccttc   360
aacaaatccg aagttcaaaa aggcggcaaa gaagcccttc aagccattct gaaatgcctg   420
aattcgtatt tgctcacgag gacttatcta gtgggtgaag caattacttt ggccgacatc   480
gtactcacat gcacgcttct ccctgcctac cagactgtct tagaccctag cttcaggaag   540
gagttccaaa atgtcaaccg gtggttcaac actatcgtca atcagccaaa agtcaaaaaa   600
gtcttgggag atgtcaaact ctgtgacaaa gagcccgtca tccctgctcc tgatgggaag   660
aagaaagaga aggcagaaaa gccttcaggg gacgctcaac ccaaaaaaga gaaaaaagct   720
gcgaaacctg cggaggagga ggaaatggac gcggcggaag ctgccctggc cgctgagccc   780
aagtccaaag accccttga cgcactgccc aaagggacat cgtcatgga cgacttcaaa   840 cgagtttact ccaacgagga cgttgataag tccattccgt acttttggga gaaattcgac   900
aaagaaaact actcgatttg gttgggcgag tacttgtaca cgacgagct gcaaaaggtc   960 ttcatgagct gcaacctcat caccggcatg taccagagac tggacaaaat gaggaaaaac  1020
gctttcgcct ccgtcattct gttcggcaaa gacaacgaca gcaccatttc cggtgtttgg  1080
gtgtggcgag gccaagatct tgcttttcaaa atgagccctg actggcaagt ggactacgag  1140
tcgtacaaat ggtccaaact cgacccgact aatcaagaac acaaaaaaat ggtcgataat  1200
tatatggcgt ggacaggaac ggacaaacaa ggccgcccat tcaatcaagg gaaaatcttc  1260
aaatga                                                             1266

<210> SEQ ID NO 30
<211> LENGTH: 100
<212> TYPE: DNA
<213> ORGANISM: Thaumastocoris peregrinus

<400> SEQUENCE: 30
gcaaaaggtc ttcatgagct gcaacctcat caccggcatg taccagagac tggacaaaat    60
gaggaaaaac gctttcgcct ccgtcattct gttcggcaaa                         100

<210> SEQ ID NO 31
<211> LENGTH: 660
<212> TYPE: DNA
<213> ORGANISM: Thaumastocoris peregrinus

<400> SEQUENCE: 31
tacatcgatc tcagcaaaag aagagtttcg cctgaggacg ttgaaaaatg cactgagaga    60

| tttgccaagg ccaaagctgt caactcaatt ttgagacacg tcgctgagct cctccactac | 120 |
| gacgccgatg aacagctgga ggacctctac cagcgaacgg cgtggttttt cgaagagcga | 180 |
| accaagaaga agtcctctgc ctacgatttc ttcaaacaag ctgttcttga caactcaatt | 240 |
| ttggctgagt gcggacttga cgaagctact caggaagtcc ttttgaccaa tatcaagagg | 300 |
| aaattgacgt cgcaggccgt caaaatcaga gctgacatcg aagtagcttg ttacggctac | 360 |
| gaagggattg acgctgttaa aactgcactc aaggccggtt tagcactctc caccgaagaa | 420 |
| cttccaatca aaatcaatct tattgctcct ccactatatg tcatgacgac agccactcct | 480 |
| gaaaaagctg atgggctcaa agcccttcaa aatgcgatcg aagtcatcga aaggaaatc | 540 |
| accagtcttg gcggtgtctt tcaagtcgaa atgggcccca aagtcgttac agcgacggac | 600 |
| gaagcggaat tggctaaaca aatggaaaga gctgaggccg aaaatgccga agtggccggg | 660 |

<210> SEQ ID NO 32
<211> LENGTH: 100
<212> TYPE: DNA
<213> ORGANISM: Thaumastocoris peregrinus

<400> SEQUENCE: 32

| tttgagacac gtcgctgagc tcctccacta cgacgccgat gaacagctgg aggacctcta | 60 |
| ccagcgaacg gcgtggtttt tcgaagagcg aaccaagaag | 100 |

<210> SEQ ID NO 33
<211> LENGTH: 645
<212> TYPE: DNA
<213> ORGANISM: Thaumastocoris peregrinus

<400> SEQUENCE: 33

| gagcacttgt actacaaatt cgacccgact gtcattcaac agagaaaggg cgaattggaa | 60 |
| ccaggcaccc aaactagcat ccaagtgatg acaaattgt gcaagtacat ttacgacaag | 120 |
| gaccaaacag atcggctgag aacgagggcc attctggccc acgtgtacca tcacgcgttg | 180 |
| cacgacaatt ggttccaagc tcgggacctc atcctcatgt cacatcttca agaagccata | 240 |
| caacattccg atccatctac ccagatcctg tacaaccgta ctatggccca tttgggactt | 300 |
| tgcgccttcc gccacgcgaa catcaaagat gcccacaatt gcttagtgga cttgatgatg | 360 |
| actggaaaaa cgaaagaact tttggcccag ggactcatgc cgcagaggca gcacgaacga | 420 |
| agcaaagaac aagaaaaagt tgaaaaacag agacaaatgc cgttccacat gcacattaac | 480 |
| ttggagttga tcgagtgcgc ttatttagtg tcagctatgc tcattgaaat tccttacatg | 540 |
| gccgctcatg aattcgatgc acggagaagg atgatctcca aaacgttcta tcagcagttg | 600 |
| agaagcagcg aacgacagtc attggtcggt cctccagaaa gtatg | 645 |

<210> SEQ ID NO 34
<211> LENGTH: 100
<212> TYPE: DNA
<213> ORGANISM: Thaumastocoris peregrinus

<400> SEQUENCE: 34

| cgacccgact gtcattcaac agagaaaggg cgaattggaa ccaggcaccc aaactagcat | 60 |
| ccaagtgatg acaaattgt gcaagtacat ttacgacaag | 100 |

<210> SEQ ID NO 35
<211> LENGTH: 1176
<212> TYPE: DNA
<213> ORGANISM: Thaumastocoris peregrinus

<400> SEQUENCE: 35

```
atgggcagcg tcaacgtgaa ccggtccgtt tccgatgcct tctatcggta caagatgccg        60
cgcctcctcg ctaaggtcga gggcaaaggg aacggcataa aaacggtcat agtgaacatg       120
gcagacgtcg ctaaggctct cggtcggcca gccacctacc caaccaagta cttcggatgc       180
gaactcggag ctcagacttt ggtggatttc aagaacgaca gattcatcgt gaacgggtcc       240
catgacgcgg ccaaactgca ggacctcctc gacgggttca ttcggaaatt cgtgctctgc       300
cccgaatgcg acaaccctga aactgatctt ctcgtcaatt cgaagaaaga gacgatcagt       360
caagggtgca aggcctgcgg cttccacggc tcctccagt  tcaaccacaa actgaacatg       420
tacattatca aaatccacc  aaacatgaat ccggctacac agggcgcttc tctgaccgaa       480
gggaaaagag ctcgtcggtc caaagccaag caaaacggcg acgtcaccaa cggagaccgt       540
tccggttcac ccaagtcaga gacgagccc  gagctcatcg tcgctcctac aaagaacatc       600
gaaataaaa  acgacgacga cctccaatgg gccgtcgacg tctccgaaga agccgtccga       660
gctcgtcttc aagacctgac cgacggagct aaaaacctga ccttaactga tgatcttgag       720
aaaccagaaa acgagcggat ggacattttc tacgtgatgg tgaaacagag gcgggacaca       780
ggcgatttgt cgactccact cgccgccaag gagatcctcg ccgaagcgga gcgacttgaa       840
atcaaaacca agctccact  tgtcctcgct gagcttcttt ttgacgacaa aatccacgtt       900
cagatcaagc gctaccgttt tttgtttctt cgtttcactc atcaagatac taaagctcaa       960
aaagctctga ttggaggcat cgagcagatc attggtttgc acaaggcttc gctcctgcct      1020
aaagtacccg cgatcttgaa acttttgtat gacctggata tactggagga aggtgtgatt      1080
cttcaatggg gagaaaaagc gagtaaaaaa tacgtgtcca agagctgag  tcaagagata      1140
catagtaaag ccacgccttt cttaacttgg ttgaaa                                1176
```

<210> SEQ ID NO 36
<211> LENGTH: 100
<212> TYPE: DNA
<213> ORGANISM: Thaumastocoris peregrinus

<400> SEQUENCE: 36

```
ggacattttc tacgtgatgg tgaaacagag gcgggacaca ggcgatttgt cgactccact        60
cgccgccaag gagatcctcg ccgaagcgga gcgacttgaa                             100
```

<210> SEQ ID NO 37
<211> LENGTH: 399
<212> TYPE: DNA
<213> ORGANISM: Thaumastocoris peregrinus
<220> FEATURE:
<221> NAME/KEY: modified_base
<222> LOCATION: (192)..(192)
<223> OTHER INFORMATION: a, c, t, g, unknown or other
<220> FEATURE:
<221> NAME/KEY: modified_base
<222> LOCATION: (368)..(368)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other

<400> SEQUENCE: 37

```
tatatttacg gtccaacttc tcagaacgaa aggatccaaa ttctacaaaa tttcaaattc        60
aatcccaaag taaatacgat ttttgtgagt aaagttgccg atacgtcgtt tgatcttccc       120
```
gaggctaatg tactgattca aatatcctct catggaggct ctcgacgtca agaagctcag     180
agattgggta anaattctca gagccaaaaa aagggagcga tcgctgaaga gtataatgcg     240
tttttcccta cacactcgtt tcccaagaca cgatggaaat ggcgtattcg cggaagcgcc     300
aagcggttcc tcgtcaatca gggctacagt tacaaagtgg tgacgaaatt ggctggtatc     360
gaccaagntc ctgacataat gtacaaaacc cgngacgag                            399

<210> SEQ ID NO 38
<211> LENGTH: 100
<212> TYPE: DNA
<213> ORGANISM: Thaumastocoris peregrinus

<400> SEQUENCE: 38
caagcggttc ctcgtcaatc agggctacag ttacaaagtg gtgacgaaat tggctggtat     60
cgaccaagat cctgacataa tgtacaaaac ccgagacgag                           100

<210> SEQ ID NO 39
<211> LENGTH: 582
<212> TYPE: DNA
<213> ORGANISM: Thaumastocoris peregrinus

<400> SEQUENCE: 39
gttctcggca tggacatcct ttgccaggcc aaatcaggta tgggaaaaac ggccgtgttc     60
gtcctggcga ctctgcaaca atggaattg accgaaaacc aagtgacggt cttggtcatg    120
tgccacacga gggaacttgc tttccaaata tccaagagt acgagcgatt ctccaagtac    180
atgccgcaca ttaaggtggc cgtattcttc ggtggtttac ccattgcaaa agatgaggaa    240
actttgaaaa acaattgtcc tcacattgtg gtcgggactc cgggacggat ccttgctctt    300
gtccgcaata aaaaattgag tttgaagaat ttgaaacatt tcattttgga tgaatgcgac    360
aaaatgttgg agcaacttga tatgagacgc gacgtacagg agatatttcg acaaactcca    420
cacagtaaac aagtgatgat gttcagtgcc actttgagca aggacatacg tcccgtctgc    480
aagaagttca tgcaagaacc gatggaagtc tacgttgatg acgaggccaa actcacactt    540
cacggtctgc aacaacacta cgttaaatta aggaaaacg ag                        582

<210> SEQ ID NO 40
<211> LENGTH: 100
<212> TYPE: DNA
<213> ORGANISM: Thaumastocoris peregrinus

<400> SEQUENCE: 40
tgacatattg gagttcaacc aggtggtcat tttcgtcaag tctgttcaac ggtgtatggc     60
tcttgctcag ctcttatgcg accaaaactt cccggctgtc                           100

<210> SEQ ID NO 41
<211> LENGTH: 726
<212> TYPE: DNA
<213> ORGANISM: Thaumastocoris peregrinus

<400> SEQUENCE: 41
atcaagcccg tcagtcccga caagaagag ctcatacacc gtctcgtata tttccaaagc     60
gagtacgaac atccgtgtga agaggacgtc cgccgaataa atgctccaaa cgacgacgat    120
gagcccaact cagactacag gttccgatac ttggccgaaa tctccatact aactgttcaa    180
cttattgttg aatttgcaaa aagacttcct ggattcgaca aacttttgag ggaagaccaa    240
atcactttac ttaaggcatg ttcaagcgaa gtgatgatgt tgaggatggc tcggcggtac    300

```
gacgcacaga ccgactcgat cctcttcgcg aacaaccaac cctataccag agactcgtat    360
aatttagcag gcatgggaga atagtcgag gatctgctca ggttttgccg gcaaatgtac    420
aatatgaaag tggacaacgc tgagtacgca cttctcaccg ccatcgttat attctcagag    480
agaccgtcac ttattgaagg gtggaaagtg gaaaaaatcc aggaaatcta tttggagggg    540
ctcaaatcct acgtggacaa caggtcgagg cctcgatccc ctacaatatt cgccaaactc    600
ctctcggtcc tgactgagct tcgaacactc ggaaatcaaa atacggagat gtgtttctca    660
ttaaaacttc aaaataagaa acttcctccg tttttgtcag aaatatggga cgtaaacgta    720
ccttag                                                              726

<210> SEQ ID NO 42
<211> LENGTH: 100
<212> TYPE: DNA
<213> ORGANISM: Thaumastocoris peregrinus

<400> SEQUENCE: 42
aacaggtcga ggcctcgatc ccctacaata ttcgccaaac tcctctcggt cctgactgag     60
cttcgaacac tcggaaatca aaatacggag atgtgtttct                          100

<210> SEQ ID NO 43
<211> LENGTH: 618
<212> TYPE: DNA
<213> ORGANISM: Thaumastocoris peregrinus

<400> SEQUENCE: 43
gaagttgtga gtcttttact ggatcgtcga gccaatgtag aacatcgcgc caagactggt     60
ttgacgcctt tgatggaagc tgcaagtgga ggatatgttg aagttggacg agtcctgctt    120
gacaaaggag ctgacgtgaa cgcaccacct gttccttcgt cccgggacac ggctctcacc    180
atagccgctg acaaagggca ttgccgtttt gttgaacttc tcctcagcag aaatgctcaa    240
gttgaagtga aaacaaaaa aggaaactct cccttgtggc tcgcagcaaa tggaggtcac    300
ctaactgtgg tcgagtacct gtacaatgct ggttcggaca tcgattccca agataaccgc    360
aaggtctcat gtctgatggc cgcgttccga aagggccatg taaaagtggt caaatggatg    420
gtgaacgctg tcacccaatt cccaagtgac caagaaatga ctaggtacat tggcacggtc    480
aatgataaag aactacttga aaaatgtcaa gagtgcacga aaatcataag aaccgccaaa    540
gaccagcaag ctgccaaagc gaataaaaac gcgacgatcc tccttgaaga actttacatg    600
gagaaaacgc gagaagag                                                 618

<210> SEQ ID NO 44
<211> LENGTH: 100
<212> TYPE: DNA
<213> ORGANISM: Thaumastocoris peregrinus

<400> SEQUENCE: 44
tttgttgaac ttctcctcag cagaaatgct caagttgaag tgaaaaacaa aaaggaaac     60 tctcccttgt ggctcgcagc aaatggaggt caccctaactg                        100

<210> SEQ ID NO 45
<211> LENGTH: 543
<212> TYPE: DNA
<213> ORGANISM: Thaumastocoris peregrinus

<400> SEQUENCE: 45
```

```
gtgttcaagt ataaaacgga acaggggtgg aggaggttcg acttccagag ccccagccgt    60
atggacagaa acgtcgagat gttcatggcc attgaaaagg ccttaattca agccaaatgt   120
ttcactctgc cagtcgtcta cgtccggccc gaagttgaaa aagcgactgc agccaaagtc   180
aaagacataa tcaaacgcca ccagggaacg gtggtcgaaa acgaagaaca ggcgacccac   240
atcctttacc ctattgtgga tcctttggat gaggaattcg ctcgacctac cctgaaaagg   300
gatcgtatgg ctttgctcca ttggtactat ttcccggatt cgcatgattc ttgggttgct   360
tcagatctcc cggtcgatcc acctgattca cccgttcaac acactctgcc ttggagggtc   420
accgcgtctt gggccattga actcgaacag tacaacgaat ggatgaacga agaagattac   480
gaagtcgacg aaactggacg gaaaaaaatt cacagacttc gtttatccgt cgacgatctc   540
atg                                                                 543

<210> SEQ ID NO 46
<211> LENGTH: 100
<212> TYPE: DNA
<213> ORGANISM: Thaumastocoris peregrinus

<400> SEQUENCE: 46
aaaagcgact gcagccaaag tcaaagacat aatcaaacgc caccagggaa cggtggtcga    60
aaacgaagaa caggcgaccc acatccttta ccctattgtg                         100

<210> SEQ ID NO 47
<211> LENGTH: 672
<212> TYPE: DNA
<213> ORGANISM: Thaumastocoris peregrinus

<400> SEQUENCE: 47
aaggaaaccg agaagaatg gatgcctgtc accaaattgg ccgtttggt cagagatggc      60 aaaatcggta ctcttgagga gatctacctc tactcccttc ccatcaagga gtatgaaatc   120
atcgactttt tcattgggcc cagcctcaag gatgaagtgc tgaagatcat gccggttcag   180
aagcagactc gagccgggca aaggactcga ttcaaggcgt tgttgccat cggcgacagc    240 aacggtcata tcggtcttgg agtcaagtgt tccaaagaag tagcgaccgc catccgtggc   300
gctatcattc tagccaagtt gtccgttgtg cccgttcgtc gaggttactg gggaaacaaa   360
atcggaaaac cccacactgt tccgtgcaag gtgaccggta atgtggctc agtccaggtg    420 aggcttatcc cggccccaag aggaactggt attgtcggcg ctcctgttcc taagaagttg   480
ctccaaatgg caggaattga cgattgttac acttcatccc gtggctccac cggaactttg   540
ggcaattttg ctaaagcaac ttacgcggct attgcgaaga cctacgcgta tttgactccg   600
gatctgtgga aggatgagcc gctcggccga ccccatacag tgagtttgc ggaccatttg    660 gacaaaaatc ac                                                       672

<210> SEQ ID NO 48
<211> LENGTH: 100
<212> TYPE: DNA
<213> ORGANISM: Thaumastocoris peregrinus

<400> SEQUENCE: 48
tgcgaagacc tacgcgtatt tgactccgga tctgtggaag gatgagccgc tcggccgacc    60
cccatacagt gagtttgcgg accatttgga caaaaatcac                         100

<210> SEQ ID NO 49
<211> LENGTH: 654
```

<212> TYPE: DNA
<213> ORGANISM: Thaumastocoris peregrinus

<400> SEQUENCE: 49

```
atggacgagg acaattggga tgtgacccct gtcgagggtg gcggagtcga ggctttggtc      60
ccggccccat cagctgaact tcctgacatc aagttgttcg gcaggtggag ctgcgacgat     120
gtccaagtgg ccgatatgtc tctccaggat tacattgcgg taaaagagaa aaacgccaag     180
tatttgcctc attcggctgg tcggttcgcg gccaagaggt tccgcaaggc ccagtgcccc     240
atcgtcgagc ggttgaccaa ttcgttaatg atgcacggga aaacaacgc caagaaactg      300
atggctgttc gcatagtcaa acacgctttt gaaattattc atctgctgac tggcgaaaac     360
ccgctgcaaa cccttgtcaa cgccatcact cactctggcc cacgcgagga ctcaactcgt     420
atcggtcgtg ccggtacggt gaggcgacaa gcagttgacg tttcgcctct tcgacgagtc     480
aatcaggcga tttggctcct ctgtactggt gctcgtgaag cggctttccg aaacattaaa     540
accatcgctg agtgtttagc tgatgagctc atcaacgccg ctaagggatc gtcgaattcg     600
tacgctatca agaagaaaga cgaactggag cgcgttgcca atccaaccg ttaa            654
```

<210> SEQ ID NO 50
<211> LENGTH: 100
<212> TYPE: DNA
<213> ORGANISM: Thaumastocoris peregrinus

<400> SEQUENCE: 50

```
atggacgagg acaattggga tgtgacccct gtcgagggtg gcggagtcga ggctttggtc      60
ccggccccat cagctgaact tcctgacatc aagttgttcg                           100
```

<210> SEQ ID NO 51
<211> LENGTH: 423
<212> TYPE: DNA
<213> ORGANISM: Thaumastocoris peregrinus

<400> SEQUENCE: 51

```
gttgacgggc acaacgggtc aatcaacgac atgcagatgc actgggacgg caccatgttt      60
gtgacagctt cgagtgacca cacagcaaag ctattcgaca ccgagtccct cagccatttg     120
aaaacatacc agaccgaaag acctgttaac agcgcctcgc tttccctat tatggaccat      180
gttgtactcg gaggtggtca agaagcgtct gttgtcacga ctacatctac tcgcgtggga     240
aaattcgacg ctcggttcta ccacgttgtt tttgaagagg aattcggtcg ggttaaaggt     300
catttcgggc cgatcaacag tttggcgttt catccggatg aaagagctt tgcaagtgga      360
ggtgaagacg gttacgtccg tgttcagtca ttcgatcaat cgtactttga atttaatttc     420
gag                                                                   423
```

<210> SEQ ID NO 52
<211> LENGTH: 100
<212> TYPE: DNA
<213> ORGANISM: Thaumastocoris peregrinus

<400> SEQUENCE: 52

```
gttgacgggc acaacgggtc aatcaacgac atgcagatgc actgggacgg caccatgttt      60
gtgacagctt cgagtgacca cacagcaaag ctattcgaca                           100
```

<210> SEQ ID NO 53
<211> LENGTH: 873
<212> TYPE: DNA

<213> ORGANISM: Thaumastocoris peregrinus

<400> SEQUENCE: 53

```
ataaaaccga tggaattaat ggtcgaggca tcacctcgga gaatcttcgc caacgcccac      60
acgtaccaca ttaattcaat atctgtcaac tcggaccaag aaacgtatct gtccgctgat     120
gacctccgaa taaatctgtg gcatttggaa ataacggatc agtccttcaa tatagttgac     180
attaagccag ctaatatgga agagctcaca gaggtaatca ctgcggccga gtttcaccca     240
ttagagtgta atctattcgt gtattcatcg agtaagggaa cgatacggtt gtgcgacatg     300
aggcaggcgg cgctttgtga tcgacacacg aaaattttg aagaaccga agacccaacg       360
aacagatcgt ttttctctga ataaatttcc agcatttcgg acgtgaaact gtccaattcc     420
gggcggtaca tgatctctag ggattatctc tcggtgaaag tctgggacct tcacatggag     480
tcgaggccta ttgaaagtta tcctgttcac gagtatttga ggtctaaact ctgctctctg     540
tacgagaacg actgtatctt cgacaaattc gagtgctgtt gggccggcaa cgaccagtac     600
atcatgaccg gctcgtacaa taattcttc cgcatgtttg atcggacctc caaacgcgac      660
gtgaccctgg aggcgtcccg ggacatcgcc aaaccgaaaa cccttctgaa accccgaaaa     720
gtctgcactg gagggaaacg gaaaaaagat gagatttcgg tcgactgttt ggattttacg     780
aagaagatcc ttcacaccgc ttggcatcca accgagaaca ttattgcagt ggccgccacc     840
aacaatttat ttctatttca ggatcgattg tag                                  873
```

<210> SEQ ID NO 54
<211> LENGTH: 100
<212> TYPE: DNA
<213> ORGANISM: Thaumastocoris peregrinus

<400> SEQUENCE: 54

```
gatttcggtc gactgtttgg attttacgaa gaagatcctt cacaccgctt ggcatccaac      60
cgagaacatt attgcagtgg ccgccaccaa caatttattt                           100
```

<210> SEQ ID NO 55
<211> LENGTH: 399
<212> TYPE: DNA
<213> ORGANISM: Thaumastocoris peregrinus

<400> SEQUENCE: 55

```
aaagtgagag tccatcttcc agagcactat ccgttcaaaa tctccatcga taggattatg      60
aataaagttt atcatccaaa tattgatgag gtctcaggca ccgtgtgttt ggatgtcatc     120
aatcaggctt ggacagcctt atacgatctg tctaacattt ttgaatcttt tctgccgcag     180
ttattgactt atcctaatcc catagatcct ctgaacggcg atgccgcagc aatgtacctt     240
cataaacctg acgagtatcg gaaaaaagtt cacgaatatg ttcggaagta cgccaccgaa     300
gaagcactta gagaacaaga acaacaagca gtttcttcag acagcgaatc ctcaatgtca     360
gatttcagtg aagatgaggc gcaagatatg gagttataa                            399
```

<210> SEQ ID NO 56
<211> LENGTH: 100
<212> TYPE: DNA
<213> ORGANISM: Thaumastocoris peregrinus

<400> SEQUENCE: 56

```
agttcacgaa tatgttcgga agtacgccac cgaagaagca cttagagaac aagaacaaca      60
agcagtttct tcagacagcg aatcctcaat gtcagatttc                           100
```

<210> SEQ ID NO 57
<211> LENGTH: 450
<212> TYPE: DNA
<213> ORGANISM: Thaumastocoris peregrinus

<400> SEQUENCE: 57

| | | | | | | |
|---|---|---|---|---|---|---|
| atggccagtc | ctacaggacg | agtggtggtt | ccgaggaact | tccgcctcct | cgaggagctt | 60 |
| gaacagggac | agcgcggagt | gagcgacggc | actatatcat | ggggtctgga | aaccgtcgac | 120 |
| gatatgactc | tcacttattg | gaccggcgtc | attatcggcc | caccccgaac | cccatatgaa | 180 |
| aatcgcatgt | acagtttacg | aatagagtgt | ggtcagaagt | acccggaaga | cgctccctcg | 240 |
| gcccgattta | tatctagaat | taatatgacc | tgcgttaata | gtactacagg | acaggttgag | 300 |
| aataaaagtg | tacccttgtt | ggcaagatgg | caaagggact | acaccattaa | atcactcctt | 360 |
| caggagcttc | gtcgtctgat | gacgataaaa | gacaacatga | aactaacaca | gccaccagaa | 420 |
| ggaagcaatt | ttcccgagtg | gcaggttaaa | | | | 450 |

<210> SEQ ID NO 58
<211> LENGTH: 100
<212> TYPE: DNA
<213> ORGANISM: Thaumastocoris peregrinus

<400> SEQUENCE: 58

| | | | | | | |
|---|---|---|---|---|---|---|
| aatcgcatgt | acagtttacg | aatagagtgt | ggtcagaagt | acccggaaga | cgctccctcg | 60 |
| gcccgattta | tatctagaat | taatatgacc | tgcgttaata | | | 100 |

<210> SEQ ID NO 59
<211> LENGTH: 100
<212> TYPE: DNA
<213> ORGANISM: Thaumastocoris peregrinus

<400> SEQUENCE: 59

| | | | | | | |
|---|---|---|---|---|---|---|
| aatcgcatgt | acagtttacg | aatagagtgt | ggtcagaagt | acccggaaga | cgctccctcg | 60 |
| gcccgattta | tacctagaat | taatatgacc | tgcgttaata | | | 100 |

<210> SEQ ID NO 60
<211> LENGTH: 914
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 60

| | | | | | | |
|---|---|---|---|---|---|---|
| agattagcct | tttcaatttc | agaaagaatg | ctaacccaca | gatggttaga | gaggcttacg | 60 |
| cagcaggtct | catcaagacg | atctacccga | gcaataatct | ccaggaaatc | aaataccttc | 120 |
| ccaagaaggt | taaagatgca | gtcaaaagat | tcaggactaa | ctgcatcaag | aacacagaga | 180 |
| aagatatatt | tctcaagatc | agaagtacta | ttccagtatg | gacgattcaa | ggcttgcttc | 240 |
| acaaaccaag | gcaagtaata | gagattggag | tctctaaaaa | ggtagttccc | actgaatcaa | 300 |
| aggccatgga | gtcaaagatt | caaatagagg | acctaacaga | actcgccgta | aagactggcg | 360 |
| aacagttcat | acagagtctc | ttacgactca | atgacaagaa | gaaaatcttc | gtcaacatgg | 420 |
| tggagcacga | cacacttgtc | tactccaaaa | atatcaaaga | tacagtctca | gaagaccaaa | 480 |
| gggcaattga | gacttttcaa | caaagggtaa | tatccggaaa | cctcctcgga | ttccattgcc | 540 |
| cagctatctg | tcactttatt | gtgaagatag | tggaaaagga | aggtggctcc | tacaaatgcc | 600 |

```
atcattgcga taaaggaaag gccatcgttg aagatgcctc tgccgacagt ggtcccaaag    660
atggaccccc acccacgagg agcatcgtgg aaaagaaga cgttccaacc acgtcttcaa    720
agcaagtgga ttgatgtgat atctccactg acgtaaggga tgacgcacaa tcccactatc    780
cttcgcaaga cccttcctct atataaggaa gttcatttca tttggagaga cacgggggga    840
ctctagatat ttttacaaca attaccaaca acaacaaaca caaacaaca ttacaattac     900 tatttacaat taca                                                     914

<210> SEQ ID NO 61
<211> LENGTH: 301
<212> TYPE: DNA
<213> ORGANISM: Figwort mosaic virus

<400> SEQUENCE: 61
tttacagtaa gaactgataa caaaaatttt acttatttcc ttagaattaa tcttaaaggt     60
gatagtaaac aaggacgatt agtccgttgg caaaattggt tcagcaagta tcaatttgat    120
gtcgaacatc ttgaaggtgt aaaaaacgtt ttagcagatt gcctcacgag agattttaat    180
gcttaaaaac gtaagcgctg acgtatgatt tcaaaaaacg cagctataaa agaagccctc    240
cagcttcaaa gttttcatca acacaaattc taaaaacaaa attttttaga gaggggagt    300 g                                                                   301

<210> SEQ ID NO 62
<211> LENGTH: 921
<212> TYPE: DNA
<213> ORGANISM: Arabidopsis thaliana

<400> SEQUENCE: 62
gtgtgtcttg tcttatctgg ttcgtggtgg tgagtttgtt acaaaaaaat ctattttccc     60
tagttgagat gggaattgaa ctatctgttg ttatgtggat tttatttct ttttctctt     120 tagaaccttta tggttgtgtc aagaagtctt gtgtacttta gttttatatc tctgttttat    180
ctcttctatt tccttaggat gcttgtgat gatgctgttt tttttgtcc ctaagcaaaa      240 aaatatcata ttatatttgg tccttggttc atttttttgg tttttttttg tcttcacata    300
taaatattgt ttgaatgtct tcaatctttt atttgtatga acaattatt taagtatcgg     360 gtgacaatgc agctattatg tattgtcgat tgttatattg gcgcccaaaa tatatactta    420
gcctaagaat ttggtaagtg agtggcttat gttttactcc agcaaaaatt gtgtgtgtat    480
taccattctg atgcgaaaca agaaaagaat ttgatctaag aaaccaagtt tattcactag    540
ttaaaaaaca aatgacctaa tgtaatcgac tccacatatc aaaatacgta aaacaaacat    600
tgtatgttga caaagggaa aagaaatgat ttatttggtt aaaaagaaag ctggattcaa     660
ttgcaacagt ttagtcgaaa tcattttgaa aggcttacaa tggattgaat gtgaatattc    720
cattaagccg cttctgtcta cacagaatgt tacgcttgga gagcagcaat cattttcacg    780
tttttatctt tttaggtgga catgtatatt attggttacg cctttggagt ttttcgaaat    840
ttatttcttt caaatcacaa gatgactaaa catcacaatc tgtttatctt cctaactagt    900 taaattttg tccccaccat t                                              921

<210> SEQ ID NO 63
<211> LENGTH: 253
<212> TYPE: DNA
<213> ORGANISM: Artificial Sequence
<220> FEATURE:
```

<221> NAME/KEY: source
<223> OTHER INFORMATION: /note="Synthetic polynucleotide"

<400> SEQUENCE: 63

```
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg ggtttttatg attagagtcc cgcaattata catttaatac   180
gcgatagaaa acaaaatata gcgcgcaaac taggataaat tatcgcgcgc ggtgtcatct   240
atgttactag atc                                                      253
```

<210> SEQ ID NO 64
<211> LENGTH: 106
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 64

```
ggctcgaacg agccgactaa ttgtctttaa acgcgcgata taagcgcaca atgctcgaga    60
aacgataaac tctatcgctc tgtcgcgtgc gtggcatctt cgcgcg                  106
```

<210> SEQ ID NO 65
<211> LENGTH: 706
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 65

```
ctctgctcgg atgctctcct catcactttg atgaacattt tggaagggct cgtagtctac    60
ccgaaagtca ttgaaaagca catcggagaa gaacttcctt ccgattctca agggacaaca   120
gtcaaatcct caccgcctcg ttcgacacga caatcaaaat tcacgggttg aagtcaggta   180
aatcgttgaa ggaattccgc gcaaaaggtc ttcatgagct gcaacctcat caccggcatg   240
taccagagac tggacaaaat gaggaaaaac gctttcgcct ccgtcattct gttcggcaaa   300
ggctcgaacg agccgactaa ttgtctttaa acgcgcgata taagcgcaca atgctcgaga   360
aacgataaac tctatcgctc tgtcgcgtgc gtggcatctt cgcgcgtttg ccgaacagaa   420
tgacggaggc gaaagcgttt ttcctcattt tgtccagtct ctggtacatg ccggtgatga   480
ggttgcagct catgaagacc ttttgcgcgg aattccttca acgatttacc tgacttcaac   540
ccgtgaattt tgattgtcgt gtcgaacgag gcggtgagga tttgactgtt gtcccttgag   600
aatcggaagg aagttcttct ccgatgtgct tttcaatgac tttcgggtag actacgagcc   660
cttccaaaat gttcatcaaa gtgatgagga gagcatccga gcagag                 706
```

<210> SEQ ID NO 66
<211> LENGTH: 300
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 66

```
ctctgctcgg atgctctcct catcactttg atgaacattt tggaagggct cgtagtctac    60
ccgaaagtca ttgaaaagca catcggagaa gaacttcctt ccgattctca agggacaaca   120
```

```
gtcaaatcct caccgcctcg ttcgacacga caatcaaaat tcacgggttg aagtcaggta    180
aatcgttgaa ggaattccgc gcaaaaggtc ttcatgagct gcaacctcat caccggcatg    240
taccagagac tggacaaaat gaggaaaaac gctttcgcct ccgtcattct gttcggcaaa    300
```

<210> SEQ ID NO 67
<211> LENGTH: 706
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 67

```
cgacccgact gtcattcaac agagaaaggg cgaattggaa ccaggcaccc aaactagcat     60
ccaagtgatg gacaaattgt gcaagtacat ttacgacaag tgacatattg gagttcaacc    120
aggtggtcat tttcgtcaag tctgttcaac ggtgtatggc tcttgctcag ctcttatgcg    180
accaaaactt cccggctgtc aatcgcatgt acagtttacg aatagagtgt ggtcagaagt    240
acccggaaga cgctccctcg gcccgattta tacctagaat taatatgacc tgcgttaata    300
ggctcgaacg agccgactaa ttgtctttaa acgcgcgata taagcgcaca atgctcgaga    360
aacgataaac tctatcgctc tgtcgcgtgc gtggcatctt cgcgcgtatt aacgcaggtc    420
atattaattc taggtataaa tcgggccgag ggagcgtctt ccgggtactt ctgaccacac    480
tctattcgta aactgtacat gcgattgaca gccgggaagt tttggtcgca taagagctga    540
gcaagagcca tacccgttg aacagacttg acgaaaatga ccacctggtt gaactccaat    600
atgtcacttg tcgtaaatgt acttgcacaa tttgtccatc acttggatgc tagtttgggt    660
gcctggttcc aattcgccct ttctctgttg aatgacagtc gggtcg                   706
```

<210> SEQ ID NO 68
<211> LENGTH: 300
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 68

```
cgacccgact gtcattcaac agagaaaggg cgaattggaa ccaggcaccc aaactagcat     60
ccaagtgatg gacaaattgt gcaagtacat ttacgacaag tgacatattg gagttcaacc    120
aggtggtcat tttcgtcaag tctgttcaac ggtgtatggc tcttgctcag ctcttatgcg    180
accaaaactt cccggctgtc aatcgcatgt acagtttacg aatagagtgt ggtcagaagt    240
acccggaaga cgctccctcg gcccgattta tacctagaat taatatgacc tgcgttaata    300
```

<210> SEQ ID NO 69
<211> LENGTH: 706
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 69

```
aaaagcgact gcagccaaag tcaaagacat aatcaaacgc caccagggaa cggtggtcga     60
aaacgaagaa caggcgaccc acatccttta ccctattgtg gttgacgggc acaacgggtc    120
aatcaacgac atgcagatgc actgggacgg caccatgttt gtgacagctt cgagtgacca    180
```

```
cacagcaaag ctattcgaca gatttcggtc gactgtttgg attttacgaa gaagatcctt    240
cacaccgctt ggcatccaac cgagaacatt attgcagtgg ccgccaccaa caatttattt    300
ggctcgaacg agccgactaa ttgtctttaa acgcgcgata taagcgcaca atgctcgaga    360
aacgataaac tctatcgctc tgtcgcgtgc gtggcatctt cgcgcgaaat aaattgttgg    420
tggcggccac tgcaataatg ttctcggttg gatgccaagc ggtgtgaagg atcttcttcg    480
taaaatccaa acagtcgacc gaaatctgtc gaatagcttt gctgtgtggt cactcgaagc    540
tgtcacaaac atggtgccgt cccagtgcat ctgcatgtcg ttgattgacc cgttgtgccc    600
gtcaaccaca atagggtaaa ggatgtgggt cgcctgttct tcgttttcga ccaccgttcc    660
ctggtggcgt tgattatgt ctttgacttt ggctgcagtc gctttt                    706

<210> SEQ ID NO 70
<211> LENGTH: 300
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 70
aaaagcgact gcagccaaag tcaaagacat aatcaaacgc caccagggaa cggtggtcga     60
aaacgaagaa caggcgaccc acatccttta ccctattgtg gttgacgggc aacgggtc      120 aatcaacgac atgcagatgc actgggacgg caccatgttt gtgacagctt cgagtgacca    180
cacagcaaag ctattcgaca gatttcggtc gactgtttgg attttacgaa gaagatcctt    240
cacaccgctt ggcatccaac cgagaacatt attgcagtgg ccgccaccaa caatttattt    300

<210> SEQ ID NO 71
<211> LENGTH: 306
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 71
gatttcggtc gactgtttgg attttacgaa gaagatcctt cacaccgctt ggcatccaac     60
cgagaacatt attgcagtgg ccgccaccaa caatttattt ggctcgaacg agccgactaa    120
ttgtctttaa acgcgcgata taagcgcaca atgctcgaga acgataaac tctatcgctc     180 tgtcgcgtgc gtggcatctt cgcgcgaaat aaattgttgg tggcggccac tgcaataatg    240
ttctcggttg gatgccaagc ggtgtgaagg atcttcttcg taaaatccaa acagtcgacc    300
gaaatc                                                                306

<210> SEQ ID NO 72
<211> LENGTH: 506
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 72
gttgacgggc aacgggtc aatcaacgac atgcagatgc actgggacgg caccatgttt      60
gtgacagctt cgagtgacca cacagcaaag ctattcgaca gatttcggtc gactgtttgg    120
attttacgaa gaagatcctt cacaccgctt ggcatccaac cgagaacatt attgcagtgg    180
```

```
ccgccaccaa caatttattt ggctcgaacg agccgactaa ttgtctttaa acgcgcgata        240
taagcgcaca atgctcgaga aacgataaac tctatcgctc tgtcgcgtgc gtggcatctt        300
cgcgcgaaat aaattgttgg tggcggccac tgcaataatg ttctcggttg gatgccaagc        360
ggtgtgaagg atcttcttcg taaaatccaa acagtcgacc gaaatctgtc gaatagcttt        420
gctgtgtggt cactcgaagc tgtcacaaac atggtgccgt cccagtgcat ctgcatgtcg        480
ttgattgacc cgttgtgccc gtcaac                                            506
```

<210> SEQ ID NO 73
<211> LENGTH: 200
<212> TYPE: DNA
<213> ORGANISM: Artificial Sequence
<220> FEATURE:
<221> NAME/KEY: source
<223> OTHER INFORMATION: /note="Synthetic polynucleotide"

<400> SEQUENCE: 73

```
gttgacgggc acaacgggtc aatcaacgac atgcagatgc actgggacgg caccatgttt         60
gtgacagctt cgagtgacca cacagcaaag ctattcgaca gatttcggtc gactgtttgg        120
attttacgaa gaagatcctt cacaccgctt ggcatccaac cgagaacatt attgcagtgg        180
ccgccaccaa caatttattt                                                   200
```

<210> SEQ ID NO 74
<211> LENGTH: 531
<212> TYPE: DNA
<213> ORGANISM: Thaumastocoris peregrinus

<400> SEQUENCE: 74

```
gcccaagaca aaatcgaacc tgtaaagagg aaaccgtatt caccatttcc taagggtaac         60
aacgctgctg agttcgcaat ggctcgtctg acgatttaa tcaattgggc gagaaagggg        120
tcactatggc ctctgacatt cggactggct tgctgcgctg tagaaatgat gcacttcgct        180
gctccgcgct acgacatgga tcgttacgga gtagtattca gggcgtctcc acgacaggct        240
gatgtcatca tcgtcgctgg tactttgact aataaaatgg cccctgcctt gagaaaagtt        300
tatgatcaga tgccggagcc gaggtgggtt atatccatgg ggagctgtgc taacggaggt        360
ggatactacc attactccta ctccgtcgtc agaggctgtg atagaattgt acctgtggat        420
atatacgttc caggttgtcc acccaccgct gaggctctcc tctatggggt tcttcaactt        480
cagaagaaaa ttaaaagaag taaccagatg cagatgtggt acaggaagta a              531
```

<210> SEQ ID NO 75
<211> LENGTH: 100
<212> TYPE: DNA
<213> ORGANISM: Thaumastocoris peregrinus

<400> SEQUENCE: 75

```
cctgtaaaga ggaaaccgta ttcaccattt cctaagggta acaacgctgc tgagttcgca         60
atggctcgtc tggacgattt aatcaattgg gcgagaaagg                             100
```

<210> SEQ ID NO 76
<211> LENGTH: 612
<212> TYPE: DNA
<213> ORGANISM: Thaumastocoris peregrinus

<400> SEQUENCE: 76

```
ctcgttgatg aagtgaagct tttcagaaat gcaagggaaa gagaaaggta cgataacatg         60
```

```
gcagacttat tcgctgtcat aaatacgctt cagaacctgg aaaaagctta cattcgagac    120
tgcgtgacgg ctaaagagta cacagccgcc tgctccaaac tcctcgtcca gtacaaagcc    180
gcttttaagc aagttcaaaa tgacgagtac ccgaccatcg aagccttcgt cgctaaatac    240
aaattggact gtcctgcggc gatggagagg attaaagaag atcgacccat tactatcaaa    300
gatgacaaag ggaacacgag taaatgcatt gcggacatcg tttcgctgtt tatcacttta    360
atggataaac tcagactgga aatgaaagcg gttgatgaac tacatccaga tttgagggat    420
ttgaccgaca caatgaaccg actcagcatc cttccttcgg actttgaagg gaagaaaaaa    480
gtcactgaat ggcttggaac actcgactcg atgtcagcct ctgacgagct gactgagcaa    540
caagtccgtc aattaatatt tgatttggaa tcgtcataca acgctttcaa caagctcttg    600
cacaatacat aa                                                        612

<210> SEQ ID NO 77
<211> LENGTH: 100
<212> TYPE: DNA
<213> ORGANISM: Thaumastocoris peregrinus

<400> SEQUENCE: 77
ctcctcgtcc agtacaaagc cgcttttaag caagttcaaa atgacgagta cccgaccatc     60
gaagccttcg tcgctaaata caaattggac tgtcctgcgg                          100

<210> SEQ ID NO 78
<211> LENGTH: 192
<212> TYPE: DNA
<213> ORGANISM: Thaumastocoris peregrinus

<400> SEQUENCE: 78
ggcgacttct actttgaact gagcatacaa attgttgaag tttgtctggc gacgaacgag     60
aaaaacggag gtatcatcgg gttgaacgag ctccgtttga aactactaaa gtcgaggggt    120
cgccacgccc aagaggtgac ccaggaggac atcctttgcg ccgccaagaa actcagtgtg    180
tttggaaatg ga                                                        192

<210> SEQ ID NO 79
<211> LENGTH: 100
<212> TYPE: DNA
<213> ORGANISM: Thaumastocoris peregrinus

<400> SEQUENCE: 79
ctggcgacga acgagaaaaa cggaggtatc atcgggttga acgagctccg tttgaaacta     60
ctaaagtcga ggggtcgcca cgcccaagag gtgacccagg                          100

<210> SEQ ID NO 80
<211> LENGTH: 516
<212> TYPE: DNA
<213> ORGANISM: Thaumastocoris peregrinus

<400> SEQUENCE: 80
aaacgggtca cccctgagga acagctgagg aagaatcaaa gagccctgaa cagagcgacg     60
agagaacttg acagggaaaa agcgcgcatg gaagcgcaag agaagaaaac gatcgcagac    120
attaagaaaa tggctaaaca tggtcaaatg gattctgtca cagtaatggc ccaagatctt    180
gtccggacga gaaggtacct aaaaaaaattc atgttgatga agccaacat ccaagcggtt    240 tcactcaaga ttcaaagtct gcgttcgcaa aacgcgatgg gagaagcgat gaggggtgtg    300
```

| | |
|---|---|
| tgcatagcca tacgaaacat gaacagacaa ctaaacatac ctcgactcca aaggatactc | 360 |
| cgggagtttg aaaaacagtc ggatataatg gatatgaaag aggcaatatc aaatgatgca | 420 |
| attgatgggg cgatggaaga tgacggggat gaagaggaaa gtgatgctgt agtttcgcaa | 480 |
| gtgttggacg agctgggtct ccaattggct gaccaa | 516 |

<210> SEQ ID NO 81
<211> LENGTH: 100
<212> TYPE: DNA
<213> ORGANISM: Thaumastocoris peregrinus

<400> SEQUENCE: 81

| | |
|---|---|
| tgaaagccaa catccaagcg gtttcactca agattcaaag tctgcgttcg caaaacgcga | 60 |
| tgggagaagc gatgaggggt gtgtgcatag ccatacgaaa | 100 |

<210> SEQ ID NO 82
<211> LENGTH: 402
<212> TYPE: DNA
<213> ORGANISM: Thaumastocoris peregrinus

<400> SEQUENCE: 82

| | |
|---|---|
| atacagaaac tgagggagat cgaggacatg ctcatcaaaa aacaagaaca cttagaaagg | 60 |
| caaatcgagc gagaattaga agtggctaaa aaaaatggaa tggccaacaa gcgggtttcc | 120 |
| cttcaagcgt tgaagaaaaa acggcggtat gagaaacaat gcagcaaat tgacgggact | 180 |
| cttagcacga ttgaaatgca aagggaggct ttggagtcgg ccagcacaaa caccgctgtc | 240 |
| ttccaaacca tgaaaatggc agcgaactct ttgaaaacag cacatttaaa catggacgtc | 300 |
| gaccatgttc acgacatcat ggatgacatc gctgaacagc aagaactggc caaggaaata | 360 |
| gccgacgcta taacccaacc tttaggtttc agcgcagacg tg | 402 |

<210> SEQ ID NO 83
<211> LENGTH: 100
<212> TYPE: DNA
<213> ORGANISM: Thaumastocoris peregrinus

<400> SEQUENCE: 83

| | |
|---|---|
| tttggagtcg gccagcacaa acaccgctgt cttccaaacc atgaaaatgg cagcgaactc | 60 |
| tttgaaaaca gcacatttaa acatggacgt cgaccatgtt | 100 |

<210> SEQ ID NO 84
<211> LENGTH: 963
<212> TYPE: DNA
<213> ORGANISM: Thaumastocoris peregrinus

<400> SEQUENCE: 84

| | |
|---|---|
| gatgcggaag acgaaaagaa gaagttgtac tgtatctacg ttgctattgg acagaaaaga | 60 |
| tccactgtcg cgcaaattgt gaaaagattg accgacaccg gggccatgaa atacaccatc | 120 |
| attgtcgctg cgactgcatc tgacgccgca cctctccaat acttggctcc ctattccggt | 180 |
| tgcgccatgg gagaatttt cagggacagc ggaaaacacg cccttatcat tttcgacgat | 240 |
| ttgtccaaac aggccgtcgc ttaccgtcaa atgtctcttc tgttgagacg tccacctggt | 300 |
| cgtgaggcct accctggaga cgttttctac cttcactctc gtctattgga acgagctgct | 360 |
| aaaatgaacg aaacgcaagg aggtggttcg ctcaccgctt tgcctgttat cgaaactcag | 420 |
| gccggtgacg tgtctgccta cattccgacc aatgttattt ccattacgga tggacaaatt | 480 |
| ttccttgaaa ctgagttgtt ctacaaaggt atccgacccg ccattaacgt cggattgtct | 540 |

```
gtgtcccgtg taggttctgc cgcccaaacc aaggccatga aacaggtggc cggttccatg    600
aaattggagc ttgctcagta tcgtgaggtc gctgctttcg cgcagttcgg ttccgacttg    660
gacgctgcca cccaacaact gctgaaccgt ggtgttcgtc ttacggaact tctcaaacaa    720
ggacaatacg ttcccatggc cattgaagaa caggtcgctg tcatctactg cggtgtccga    780
ggtttcttgg acaaattgga cccggccaag atcacccaat cgagaaggag gttccttcaa    840
cacatcaaga cttctcacaa agacctgttg gcctccatcg ccaaagaggg aaagatcagt    900
gacgaaaatg atgccaagat gaagggcatt gttacttctt tcctcagtgg cttctccggc    960
tag                                                                  963
```

\<210\> SEQ ID NO 85
\<211\> LENGTH: 468
\<212\> TYPE: DNA
\<213\> ORGANISM: Thaumastocoris peregrinus

\<400\> SEQUENCE: 85

```
ggaaatctgt tggcgtcctg ctctgacgat atgactctta aaatttggtc gatgaaacaa     60
gacacgtgtg tgtacgactt gcaagctcac aataaggaaa tttacactat caagtgggagc   120 ccaactggac cgggcacact gaacccaaat atgaatctta ttttagccag tgcctcattc   180
gattctactg ttcgtctctg ggaagtggat cggggagctt gtattcacac tttaactaaa    240
cacactgagc ccgtgtacag cgtcgccttt tcccccgacg gtaaattctt ggcttctgga    300
agcttcgaca atgcgttcca tatatggtca actcagtcgg ggcacttagt tcacagttac    360
aaaggaacgg gtgggatatt cgaagtatgt tggaactctc ggggcgataa agtcggagct    420
agtgcatcgg acggaagcgt atttgttttg gacctccgca agctgtga                 468
```

\<210\> SEQ ID NO 86
\<211\> LENGTH: 450
\<212\> TYPE: DNA
\<213\> ORGANISM: Thaumastocoris peregrinus

\<400\> SEQUENCE: 86

```
cttttttgatt tacttgacat attggagttc aaccaggtgg tcattttcgt caagtctgtt     60
caacggtgta tggctcttgc tcagctctta tgcgaccaaa acttcccggc tgtcgcgatc    120
cacagagcca tgaatcaaga ggagcggctc tcgaaatatc aagaatttaa agacttccaa    180
aagaggattc ttgtggcgac caatctcttt ggccgaggaa tggacataga gagagtgaac    240
attgttttca actacgacat gcccgaagac tcagacactt atttacatcg tgtggctcgg    300
gctggtcgtt ttggaactaa gggtttggcc atcacgtttg ccagtgacga aaacgacgcc    360
aaagttctca atcaagtaca ggaccgattt gatgtcaaca ttactgagtt acctgacgag    420
attgatctgt catcttacat tgacggccgg                                    450
```

\<210\> SEQ ID NO 87
\<211\> LENGTH: 399
\<212\> TYPE: DNA
\<213\> ORGANISM: Thaumastocoris peregrinus

\<400\> SEQUENCE: 87

```
tatatttacg gtccaacttc tcagaacgaa aggatccaaa ttctacaaaa tttcaaattc     60
aatcccaaag taaatacgat ttttgtgagt aaagttgccg atacgtcgtt tgatcttccc    120
gaggctaatg tactgattca aatatcctct catggaggct ctcgacgtca agaagctcag    180
```

```
agattgggta aaaattctca gagccaaaaa aagggagcga tcgctgaaga gtataatgcg      240 tttttttccta cacactcgtt tcccaagaca cgatggaaat ggcgtattcg cggaagcgcc     300
aagcggttcc tcgtcaatca gggctacagt tacaaagtgg tgacgaaatt ggctggtatc     360
gaccaagatc ctgacataat gtacaaaacc cgagacgag                            399
```